(12) United States Patent
Karafin et al.

(10) Patent No.: US 11,579,465 B2
(45) Date of Patent: Feb. 14, 2023

(54) FOUR DIMENSIONAL ENERGY-FIELD PACKAGE ASSEMBLY

(71) Applicant: Light Field Lab, Inc., San Jose, CA (US)

(72) Inventors: Jonathan Sean Karafin, San Jose, CA (US); Brendan Elwood Bevensee, San Jose, CA (US)

(73) Assignee: Light Field Lab, Inc., San Jose, CA (US)

( * ) Notice: Subject to any disclaimer, the term of this patent is extended or adjusted under 35 U.S.C. 154(b) by 197 days.

(21) Appl. No.: 16/962,188

(22) PCT Filed: Jan. 13, 2019

(86) PCT No.: PCT/US2019/013408
§ 371 (c)(1),
(2) Date: Jul. 14, 2020

(87) PCT Pub. No.: WO2019/140346
PCT Pub. Date: Jul. 18, 2019

(65) Prior Publication Data
US 2021/0063965 A1 Mar. 4, 2021

Related U.S. Application Data

(60) Provisional application No. 62/617,293, filed on Jan. 14, 2018.

(51) Int. Cl.
*G03H 1/26* (2006.01)
*G02B 30/10* (2020.01)
(Continued)

(52) U.S. Cl.
CPC ............. *G02B 30/10* (2020.01); *A61B 3/032* (2013.01); *A61B 3/036* (2013.01); *A61M 21/00* (2013.01);
(Continued)

(58) Field of Classification Search
CPC ...... G02B 30/10; G02B 6/0005; G02B 30/26; G02B 30/27; A61B 3/032; A61B 3/036;
(Continued)

(56) References Cited

U.S. PATENT DOCUMENTS 5,004,335 A 4/1991 Montes
5,187,360 A 2/1993 Pasco
(Continued)

FOREIGN PATENT DOCUMENTS

CN 101674512 A 3/2010
CN 104837003 A 8/2015
(Continued)

OTHER PUBLICATIONS

CN201980018318.3 First Office Action of the Chinese Patent Office dated Dec. 20, 2021.
(Continued)

*Primary Examiner* — Thai Q Tran
*Assistant Examiner* — Stephen R Smith
(74) *Attorney, Agent, or Firm* — Charles C. Yang

(57) ABSTRACT

Four dimensional (4D) energy-field package assembly for projecting energy fields according to a 4D coordinate function. The 4D energy-field package assembly includes an energy-source system having energy sources capable of providing energy to energy locations, and energy waveguides for directing energy from the energy locations from one side of the energy waveguide to another side of the energy waveguide along energy propagation paths.

43 Claims, 28 Drawing Sheets

(51) Int. Cl.

| | |
|---|---|
| *G02B 30/26* | (2020.01) |
| *A61B 3/032* | (2006.01) |
| *A61B 3/036* | (2006.01) |
| *G03H 1/00* | (2006.01) |
| *H04N 13/344* | (2018.01) |
| *G02B 30/27* | (2020.01) |
| *F21V 8/00* | (2006.01) |
| *B33Y 30/00* | (2015.01) |
| *B33Y 50/02* | (2015.01) |
| *B29C 64/282* | (2017.01) |
| *B29C 64/232* | (2017.01) |
| *B29C 64/255* | (2017.01) |
| *B29C 64/393* | (2017.01) |
| *B29C 64/236* | (2017.01) |
| *B29C 64/241* | (2017.01) |
| *B29C 64/135* | (2017.01) |
| *A61M 21/00* | (2006.01) |
| *G06F 3/01* | (2006.01) |
| *G06F 3/03* | (2006.01) |
| *G06F 3/04815* | (2022.01) |
| *G06T 19/00* | (2011.01) |

(52) U.S. Cl.
CPC .......... *B29C 64/135* (2017.08); *B29C 64/232* (2017.08); *B29C 64/236* (2017.08); *B29C 64/241* (2017.08); *B29C 64/255* (2017.08); *B29C 64/282* (2017.08); *B29C 64/393* (2017.08); *B33Y 30/00* (2014.12); *B33Y 50/02* (2014.12); *G02B 6/0005* (2013.01); *G02B 30/26* (2020.01); *G02B 30/27* (2020.01); *G03H 1/0005* (2013.01); *G03H 1/268* (2013.01); *G06F 3/011* (2013.01); *G06F 3/0325* (2013.01); *G06F 3/04815* (2013.01); *G06T 19/006* (2013.01); *H04N 13/344* (2018.05); *A61B 2503/12* (2013.01); *A61M 2021/005* (2013.01); *G03H 2222/34* (2013.01); *G03H 2223/16* (2013.01)

(58) Field of Classification Search
CPC .............. A61B 2503/12; A61M 21/00; A61M 2021/005; B29C 64/135; B29C 64/232; B29C 64/236; B29C 64/241; B29C 64/255; B29C 64/282; B29C 64/393; B33Y 30/00; B33Y 50/02; G03H 1/0005; G03H 1/268; G03H 2222/34; G03H 2223/16; G06T 19/006; H04N 13/344; A61N 2005/063; A61N 2005/0642; A61N 2005/0652
USPC ............................................................. 348/40
See application file for complete search history.

(56) References Cited

U.S. PATENT DOCUMENTS

| | | |
|---|---|---|
| 5,374,976 A | 12/1994 | Spannenburg |
| 5,396,350 A | 3/1995 | Beeson et al. |
| 5,822,125 A | 10/1998 | Meyers |
| 6,169,594 B1 | 1/2001 | Aye et al. |
| 6,326,939 B1 | 12/2001 | Smith |
| 6,418,254 B1 | 7/2002 | Shikata et al. |
| 6,556,280 B1 | 4/2003 | Kelsey et al. |
| 6,680,761 B1 | 1/2004 | Greene et al. |
| 7,050,020 B2 | 5/2006 | Uehara et al. |
| 7,203,005 B2 | 4/2007 | Jiang et al. |
| 7,986,374 B2 | 7/2011 | Ijzerman et al. |
| 8,149,265 B2 | 4/2012 | Smalley et al. |
| 8,308,329 B1 | 11/2012 | Sethna |
| 8,345,144 B1 | 1/2013 | Georgiev et al. |
| 8,369,546 B2 | 2/2013 | Pompei |
| 8,442,397 B2 | 5/2013 | Kang et al. |
| 8,736,675 B1 | 5/2014 | Holzbach et al. |
| 8,783,675 B2 | 7/2014 | Buck et al. |
| 8,879,766 B1 | 11/2014 | Zhang |
| 8,953,012 B2 | 2/2015 | Williams et al. |
| 8,977,090 B2 | 3/2015 | Lambert et al. |
| 9,143,678 B2 | 9/2015 | Park et al. |
| 9,179,134 B2 | 11/2015 | Ranieri et al. |
| 9,188,737 B2 | 11/2015 | Joseph et al. |
| 9,256,060 B2 | 2/2016 | Kobori et al. |
| 9,343,020 B2 | 5/2016 | Heide et al. |
| 9,405,124 B2 | 8/2016 | Hirsch et al. |
| 9,411,511 B1 | 8/2016 | Sivertsen |
| 9,817,626 B2 | 11/2017 | Ur et al. |
| 9,874,761 B2 | 1/2018 | Putten et al. |
| 9,904,065 B2 | 2/2018 | Jin et al. |
| 9,945,988 B2 | 4/2018 | Powell |
| 10,009,597 B2 | 6/2018 | Karafin et al. |
| 10,298,915 B2 | 5/2019 | Huh et al. |
| 10,363,818 B2 | 7/2019 | Coser et al. |
| 10,488,584 B2 | 11/2019 | Karafin et al. |
| 10,551,628 B2 | 2/2020 | Karafin et al. |
| 2001/0028485 A1 | 10/2001 | Kremen |
| 2002/0028045 A1 | 3/2002 | Yoshimura et al. |
| 2002/0122113 A1 | 9/2002 | Foote |
| 2003/0030912 A1 | 2/2003 | Gleckman et al. |
| 2003/0137730 A1 | 7/2003 | Fridman et al. |
| 2004/0080938 A1 | 4/2004 | Holman et al. |
| 2004/0135100 A1 | 7/2004 | Menon et al. |
| 2004/0240777 A1 | 12/2004 | Woodgate et al. |
| 2005/0093713 A1 | 5/2005 | Orme |
| 2005/0119575 A1 | 6/2005 | Ladabaum et al. |
| 2005/0243275 A1 | 11/2005 | Curatu |
| 2005/0260677 A1 | 11/2005 | Saaski |
| 2006/0028400 A1 | 2/2006 | Lapstun et al. |
| 2006/0077319 A1 | 4/2006 | Kitamura |
| 2006/0171007 A1 | 8/2006 | Chen et al. |
| 2006/0191566 A1 | 8/2006 | Schaafsma |
| 2007/0091638 A1 | 4/2007 | Ijzerman et al. |
| 2007/0097321 A1 | 5/2007 | Whitehead et al. |
| 2008/0035834 A1 | 2/2008 | Gleckler |
| 2008/0144174 A1* | 6/2008 | Lucente .............. H04N 13/307 348/E13.028 |
| 2008/0170293 A1 | 7/2008 | Lucente et al. |
| 2008/0174670 A1 | 7/2008 | Olsen et al. |
| 2008/0192313 A1 | 8/2008 | Matsumura et al. |
| 2009/0040294 A1 | 2/2009 | Smalley et al. |
| 2009/0235750 A1 | 9/2009 | Chang et al. |
| 2009/0247305 A1 | 10/2009 | Kanekal |
| 2009/0273575 A1 | 11/2009 | Pryor |
| 2010/0125356 A1 | 5/2010 | Shkolnik et al. |
| 2010/0245824 A1 | 9/2010 | Schwarz et al. |
| 2010/0277779 A1 | 11/2010 | Futterer et al. |
| 2010/0289870 A1 | 11/2010 | Leister |
| 2011/0069189 A1 | 3/2011 | Venkataraman et al. |
| 2011/0134040 A1 | 6/2011 | Duparre et al. |
| 2011/0157180 A1 | 6/2011 | Burger et al. |
| 2011/0242461 A1 | 10/2011 | Escuti et al. |
| 2011/0254916 A1 | 10/2011 | Fan et al. |
| 2011/0254980 A1 | 10/2011 | Perchant et al. |
| 2012/0050833 A1 | 3/2012 | Bove, Jr. et al. |
| 2012/0147205 A1 | 6/2012 | Lelescu et al. |
| 2012/0206390 A1 | 8/2012 | Ueno et al. |
| 2012/0300044 A1 | 11/2012 | Thomas et al. |
| 2013/0127832 A1 | 5/2013 | Lee et al. |
| 2013/0163089 A1 | 6/2013 | Bohn |
| 2013/0170004 A1 | 7/2013 | Futterer |
| 2013/0216123 A1 | 8/2013 | Shroff et al. |
| 2013/0250150 A1 | 9/2013 | Malone et al. |
| 2013/0265485 A1 | 10/2013 | Kang |
| 2014/0043370 A1 | 2/2014 | Payne et al. |
| 2014/0072141 A1 | 3/2014 | Cohen |
| 2014/0078333 A1 | 3/2014 | Miao |
| 2014/0104665 A1 | 4/2014 | Popovich et al. |
| 2014/0132694 A1 | 5/2014 | Shacham et al. |
| 2014/0253613 A1 | 9/2014 | Gilbert |
| 2014/0300694 A1 | 10/2014 | Smalley et al. |
| 2014/0300695 A1 | 10/2014 | Smalley et al. |

(56) References Cited

U.S. PATENT DOCUMENTS

| | | | |
|---|---|---|---|
| 2014/0320530 | A1 | 10/2014 | Gruber et al. |
| 2014/0358002 | A1 | 12/2014 | Daoura |
| 2015/0007025 | A1 | 1/2015 | Sassi et al. |
| 2015/0016777 | A1 | 1/2015 | Abovitz et al. |
| 2015/0022754 | A1 | 1/2015 | Jepsen et al. |
| 2015/0092071 | A1 | 4/2015 | Meng et al. |
| 2015/0146029 | A1 | 5/2015 | Venkataraman et al. |
| 2015/0146030 | A1 | 5/2015 | Venkataraman et al. |
| 2015/0178939 | A1 | 6/2015 | Bradski et al. |
| 2015/0185841 | A1 | 7/2015 | Levesque et al. |
| 2015/0192995 | A1 | 7/2015 | Subramanian et al. |
| 2015/0197062 | A1 | 7/2015 | Shinar et al. |
| 2015/0241608 | A1 | 8/2015 | Shian et al. |
| 2015/0277378 | A1 | 10/2015 | Smithwick et al. |
| 2015/0285682 | A1 | 10/2015 | Popovich et al. |
| 2015/0288063 | A1 | 10/2015 | Johnson et al. |
| 2015/0294472 | A1 | 10/2015 | Putraya et al. |
| 2015/0331241 | A1 | 11/2015 | Haddick |
| 2015/0378183 | A1 | 12/2015 | Pernice et al. |
| 2016/0014529 | A1 | 1/2016 | Hecht et al. |
| 2016/0041386 | A1 | 2/2016 | Moreno |
| 2016/0042501 | A1 | 2/2016 | Huang et al. |
| 2016/0091786 | A1 | 3/2016 | Kazmierski et al. |
| 2016/0103419 | A1 | 4/2016 | Callagy et al. |
| 2016/0105660 | A1 | 4/2016 | Ito et al. |
| 2016/0139402 | A1 | 5/2016 | Lapstun |
| 2016/0180511 | A1 | 6/2016 | Zhou et al. |
| 2016/0209657 | A1 | 7/2016 | Popovich et al. |
| 2016/0223988 | A1 | 8/2016 | Bove et al. |
| 2016/0282808 | A1* | 9/2016 | Smalley ............... G03H 1/0005 |
| 2016/0301430 | A1 | 10/2016 | Mohamadi |
| 2016/0309065 | A1 | 10/2016 | Karafin et al. |
| 2017/0139213 | A1 | 5/2017 | Schmidtlin |
| 2017/0214907 | A1 | 7/2017 | Lapstun |
| 2017/0261729 | A1 | 9/2017 | Powell |
| 2017/0347874 | A1 | 12/2017 | Novik |
| 2018/0131926 | A1 | 5/2018 | Shanks et al. |
| 2018/0309981 | A1* | 10/2018 | Meacham ............... G02B 30/27 |
| 2018/0361680 | A1 | 12/2018 | Bharti et al. |
| 2019/0064435 | A1 | 2/2019 | Karafin et al. |
| 2019/0364263 | A1 | 11/2019 | Jannard et al. |

FOREIGN PATENT DOCUMENTS

| | | |
|---|---|---|
| CN | 205185315 U | 4/2016 |
| CN | 105637415 A | 6/2016 |
| CN | 113504657 A | 10/2021 |
| EP | 0973152 A2 | 1/2000 |
| JP | 2009053263 A | 3/2009 |
| TW | 200700695 A | 1/2007 |
| WO | 0154106 A2 | 7/2001 |
| WO | 2005057670 A2 | 6/2005 |
| WO | 2008048360 A2 | 4/2008 |
| WO | 2014188149 A1 | 11/2014 |
| WO | 2015071903 A1 | 5/2015 |
| WO | 2015148334 A1 | 10/2015 |
| WO | 2016007920 A1 | 1/2016 |
| WO | 2017127897 A1 | 8/2017 |

OTHER PUBLICATIONS

EP-19738937.2 European Extended Search Report of European Patent Office dated Oct. 20, 2021.
Kim et al., "Recent researches based on integral imaging display method", 3D Research, vol. 1, No. 1, Mar. 1, 2010 (Mar. 1, 2010), pp. 17-27.
AU-2017296074 Notice of Acceptance dated Mar. 12, 2020.
AU-2017296234 Examination Report No. 1 dated Jul. 19, 2018.
AU-2017296238 Examination Report No. 1 dated Aug. 2, 2018.
AU-2017297625 Examination Report No. 2 dated Sep. 24, 2018.
AU-2017297627 Examination Report No. 1 dated Aug. 21, 2018.
AU-2019200180 Notice of Acceptance dated Nov. 26, 2020.
CA-3006518 Office action dated Sep. 28, 2018.
CA-3006523 Office action dated Sep. 4, 2018.
CA-3006528 Office action dated Aug. 30, 2018.
EA-201892633 Office Action of the Eurasian Patent Office dated Aug. 10, 2020.
EA-201892634 Office Action of the Eurasian Patent Office dated Mar. 25, 2020.
Energy_ In illustrated Dictionary of Science, Andromeda, edited by Michael Allaby. Windmill Books {Andromeda International), 1988. https://search.credoredererence.com/contenl/entry/andidsci/energy/0?institutionId= 7 43 {Year: 1988).
EP-17828597.9—European Search Report of the European Patent Office dated Jul. 20, 2020.
EP-17828622.5 European Extended Search Report of European Patent Office dated Mar. 6, 2020.
EP-17828628.2 European Extended Search Report of European Patent Office dated Mar. 6, 2020.
EP-17828632.4 European Search Report of European Patent Office dated Jun. 29, 2020.
EP-17828633.2 European Search Report of European Patent Office dated Oct. 23, 2020.
Fifty years of Anderson localization, Ad Lagendijk, Bart van Tiggelen, and Diederik S. Wiersma, Phsyics Today 62(8), 24 (2009). {Year: 2009).
Gerald, "Size of Letters Required for Visibility as a Function of Viewing Distance and Observer Visual Acuity", U.S. Department of Commerce/National Bureau of Statistics, Jul. 1983.
Hoshi, et al., "Noncontact tactile display based on radiation pressure of airborne ultrasound." IEEE Transactions on Haptics, vol. 3, No. 3 (2010): pp. 155-165.
International Search Report and Written Opinion of PCT/US2017/042276 dated Nov. 24, 2017.
International Search Report and Written Opinion of PCT/US2019/013408 dated Apr. 23, 2019.
International Search Report and Written Opinion of PCT/US2019/013554 dated Mar. 28, 2019.
International Search Report and Written Opinion dated Dec. 27, 2017 in International Patent Application No. PCT/US17/42467.
International Search Report and Written Opinion dated Dec. 28, 2017 in International Patent Application No. PCT/US2017/042470.
International Search Report and Written Opinion dated Nov. 17, 2017 in International Patent Application No. PCT/US17/42452.
International Search Report and Written Opinion dated Nov. 28, 2017 in International Patent Application No. PCT/US17/42466.
International Search Report and Written Opinion dated Nov. 9, 2017 in International Patent Application No. PCT/US17/42679.
International Search Report and Written Opinion of PCT/US2016/023756 dated Jul. 15, 2016.
International Search Report and Written Opinion of PCT/US2017/042462 dated Oct. 30, 2017.
International Search Report and Written Opinion of PCT/US2017/042468 dated Nov. 27, 2017.
International Search Report and Written Opinion of PCT/US2019/013409 dated Apr. 24, 2019.
International Search Report and Written Opinion of PCT/US2019/013410 dated Apr. 1, 2019.
International Search Report and Written Opinion of PCT/US2019/013523 dated Jun. 18, 2019.
International Search Report and Written Opinion of PCT/US2019/013539 dated Mar. 22, 2019.
NZ-743820 First Examination Report dated Aug. 30, 2018.
NZ-743822 First Examination Report dated Aug. 28, 2018.
NZ-743822 Further Examination Report dated Jan. 29, 2019.
NZ-743823 First Examination Report dated Sep. 14, 2018.
Plesniak, Coincident Display Using Haptics and Holographic Video, Spatial Imaging Group, pp. 18-23 (Year: 1998).
TW-106123879 Office Action of the Taiwan Patent Office dated Nov. 2, 2020.
Watanabe, et al., "A Method for controlling tactile sensation of surfaces roughness using ultrasonic vibration." Robotics and Automation, 1995 Proceedings., 1995 IEEE International Conference on vol. 1. IEEE, 1995.

(56) References Cited

OTHER PUBLICATIONS

Wetzstein et al., "On Plenoptic Multiplexing and Reconstruction." International Journal on Computer Vision {IJVC), Springer, 2013, 101(2), pp. 384-400 [online][retrieved on Sep. 26, 2017].
TW-108101417 Office Action of the Taiwan patent office dated Nov. 30, 2022.

* cited by examiner

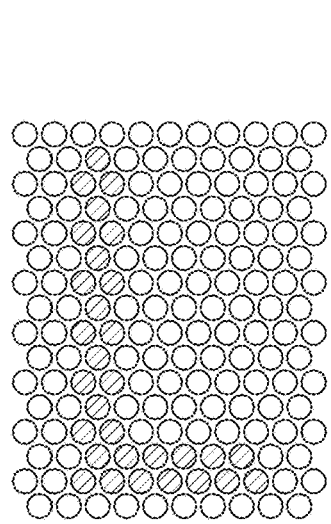 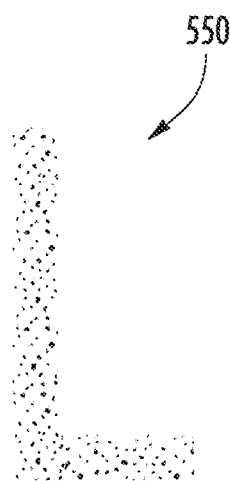
FIG. 5A          FIG. 5B
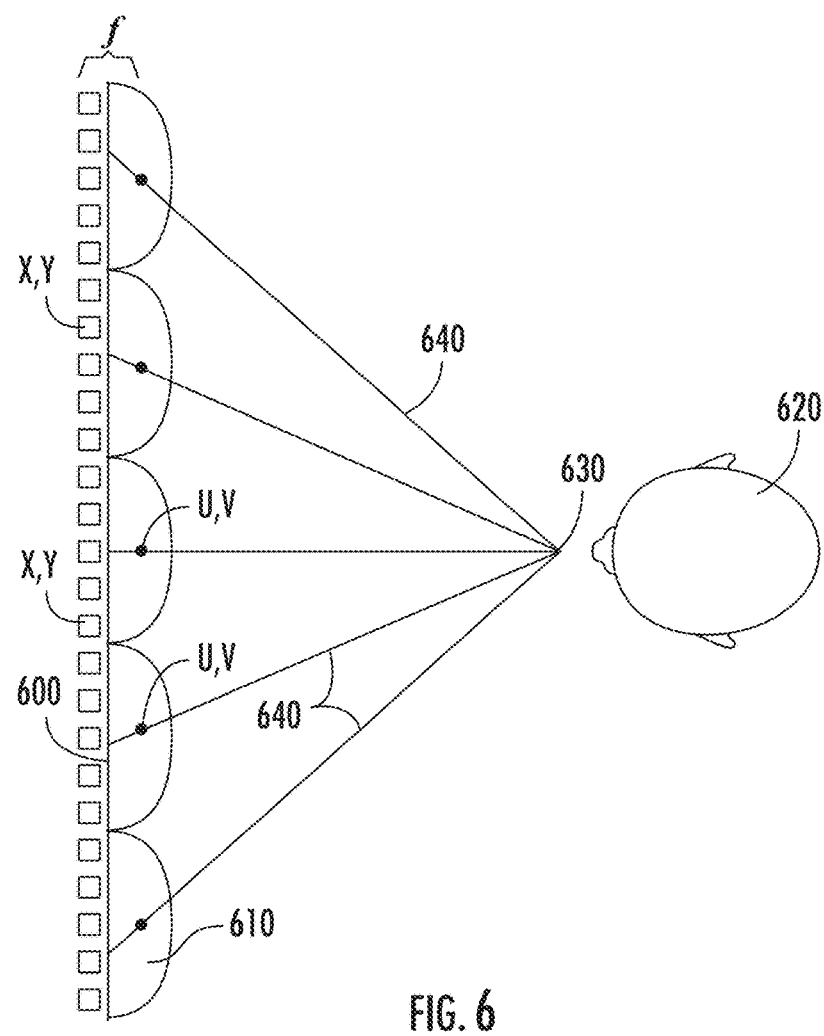
FIG. 6

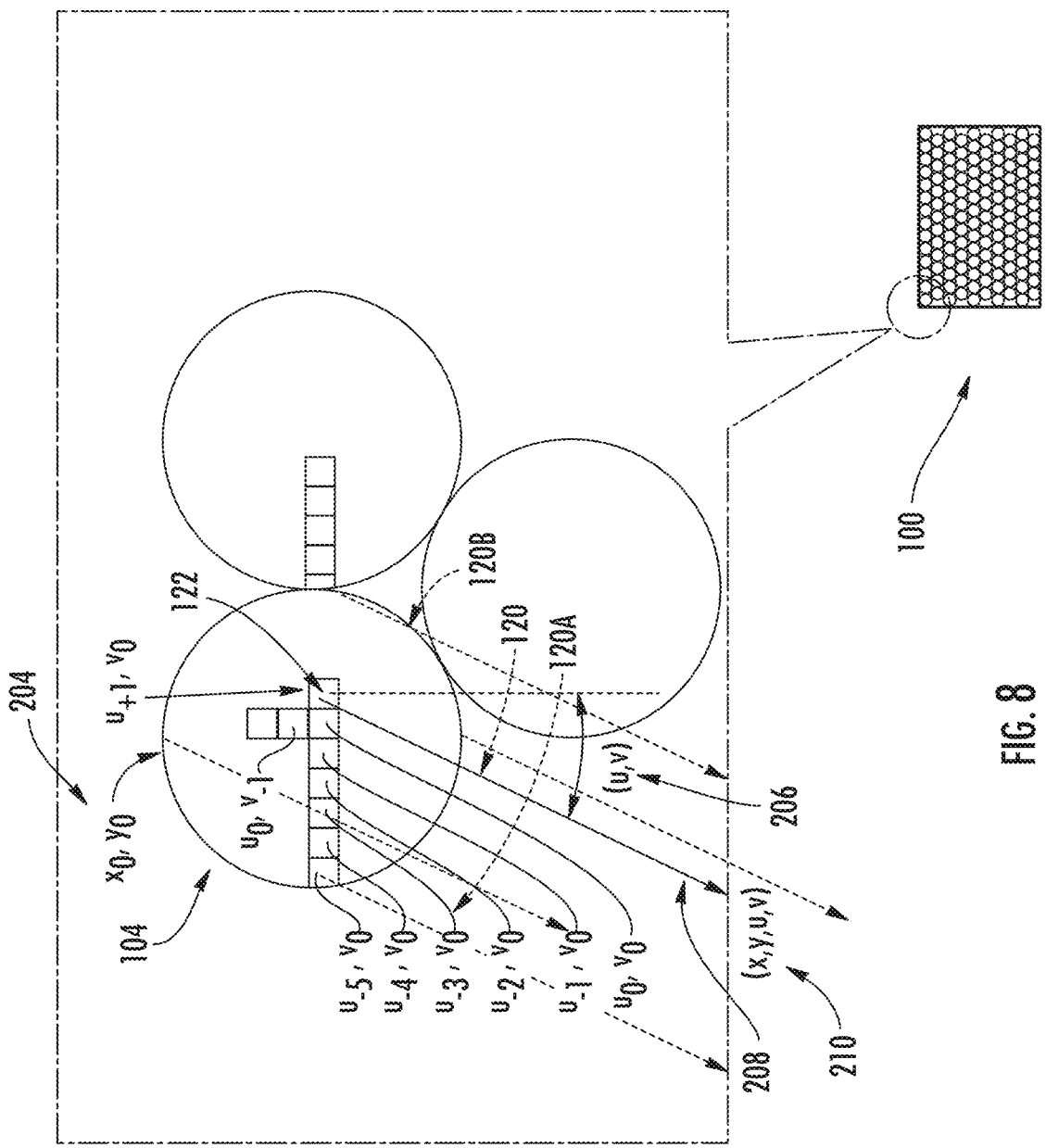

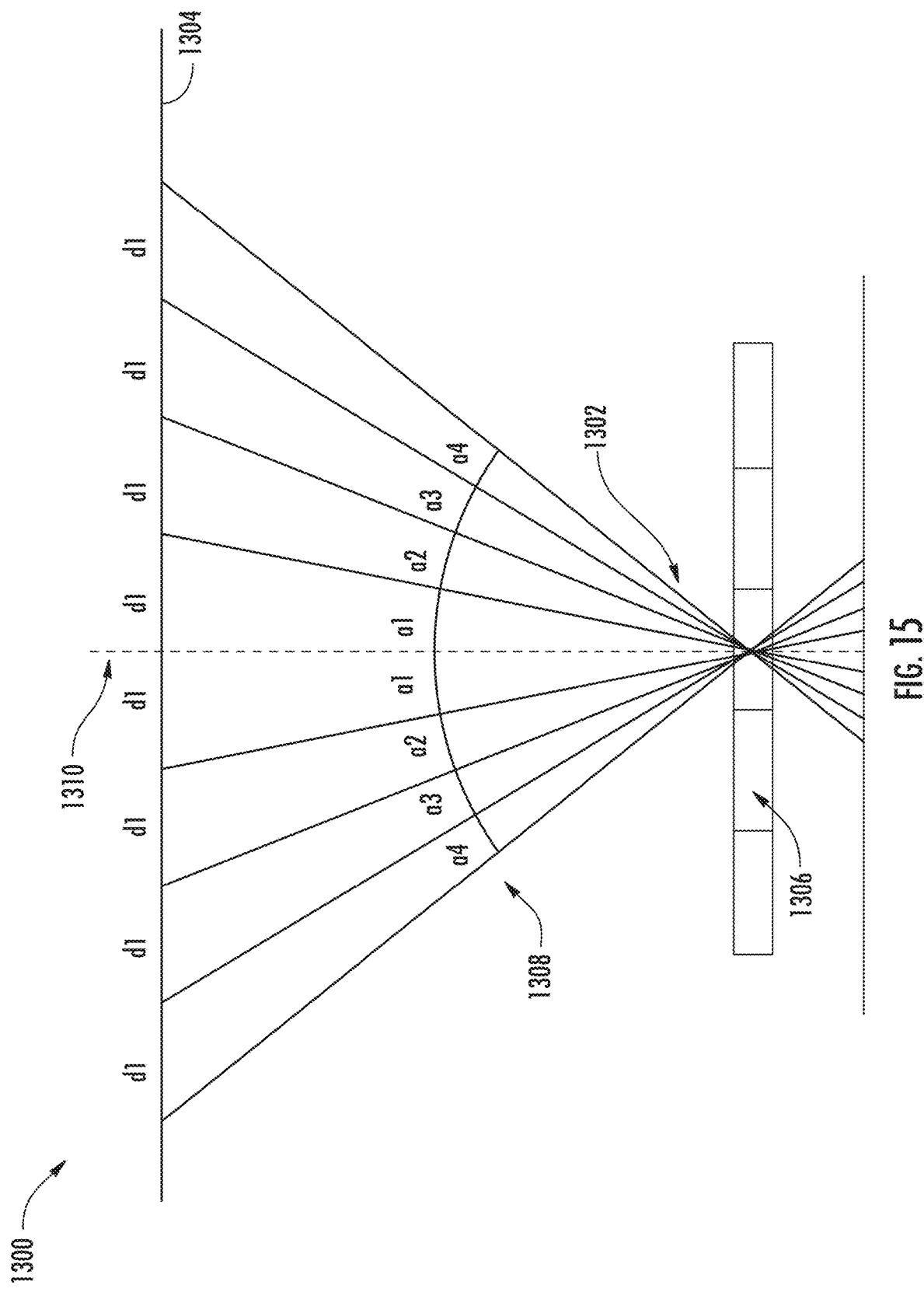

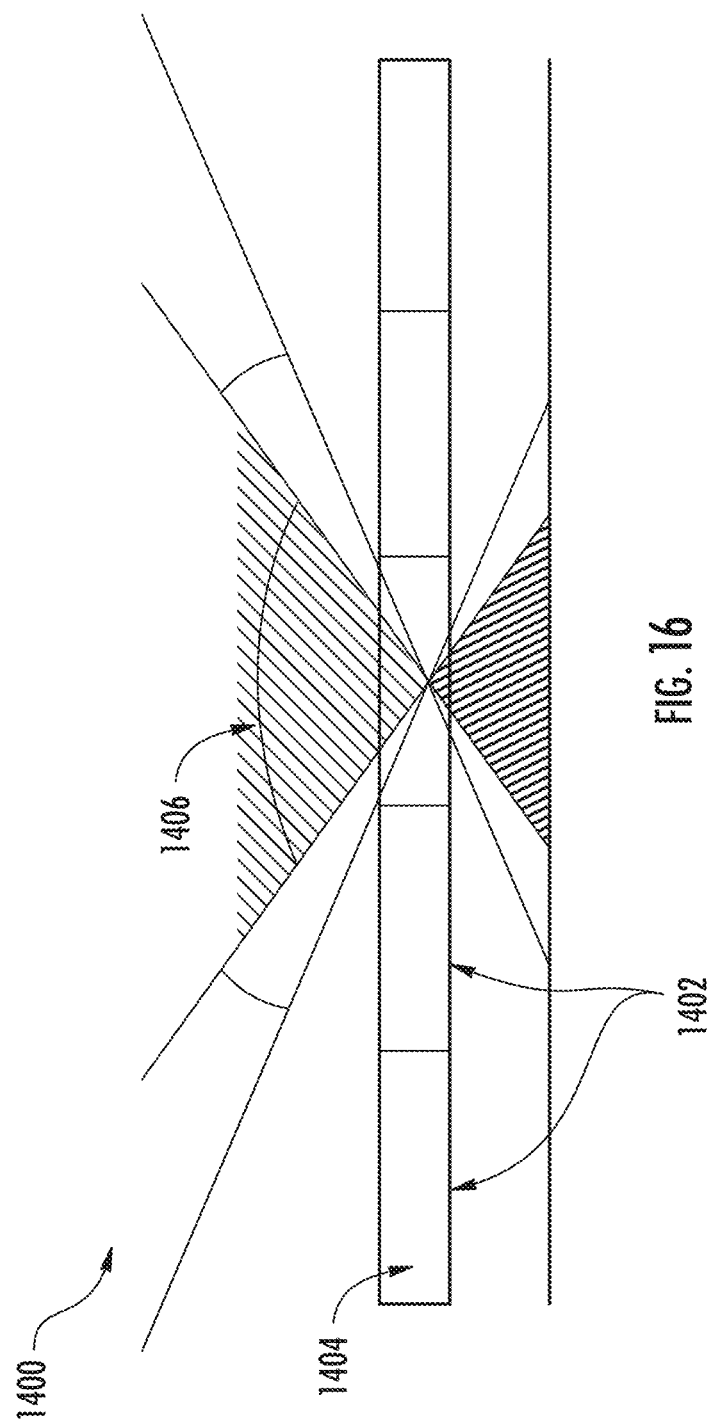

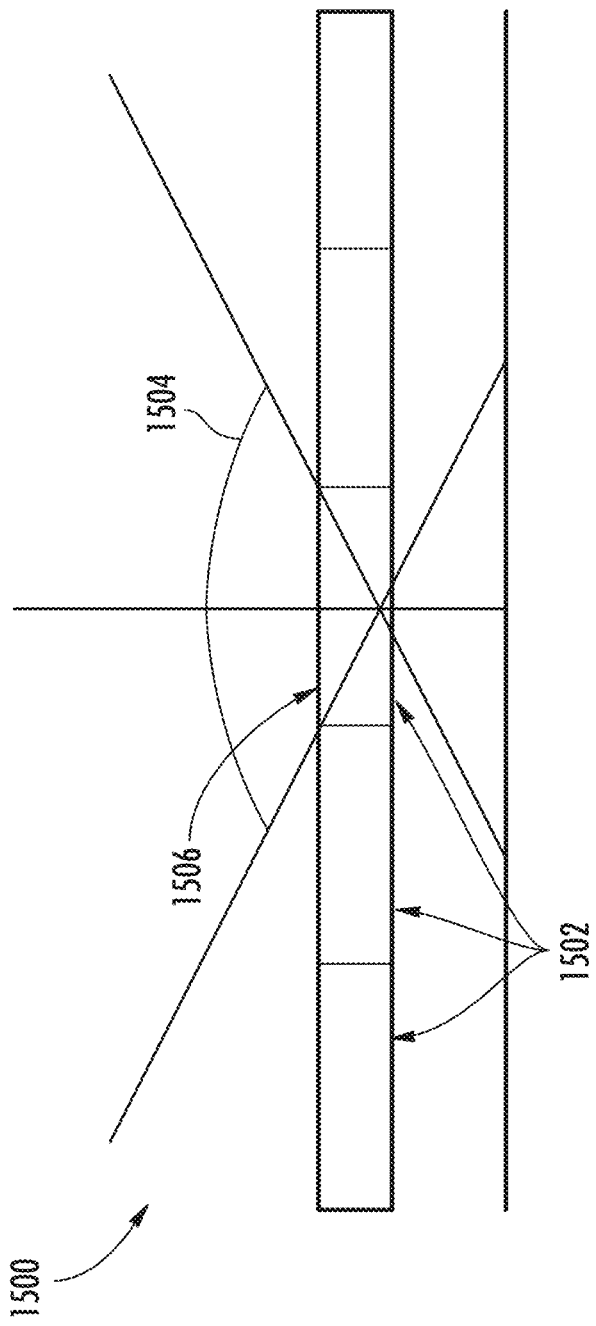

FOUR DIMENSIONAL ENERGY-FIELD PACKAGE ASSEMBLY

CROSS-REFERENCE TO RELATED APPLICATIONS

This application claims the benefit of priority to U.S. Provisional Patent U.S. Provisional Patent Application No. 62/617,293, entitled "Novel Application of Holographic and Light Field Technology," filed Jan. 14, 2018, which are both herein incorporated by reference in their entirety.

TECHNICAL FIELD

This disclosure is related to energy directing devices, and specifically to an assembly for energy-field packages configured to direct energy in accordance with a four-dimensional energy-field system.

BACKGROUND

The dram of an interactive virtual world within a "holo-deck" chamber as popularized by Gene Roddenberry's Star Trek and originally envisioned by author Alexander Moszkowski in the early 1900s has been the inspiration for science fiction and technological innovation for nearly a century. However, no compelling implementation of this experience exists outside of literature, media, and the collective imagination of children and adults alike.

SUMMARY

Disclosed are energy-field package assemblies in accordance with a four-dimensional energy-field system. In one embodiment, a four-dimensional (4D) energy-field package assembly includes a plurality of modular 4D energy-field packages with each modular 4D energy-field package having an energy-source system able to provide energy to a plurality of energy locations and having a plurality of energy sources. The 4D energy-field package may also include at least one energy waveguide where each energy waveguide is able to direct energy from the plurality of energy locations from a first side of the energy waveguide to a second side of the energy waveguide along a plurality of energy propagation paths extending through the plurality of energy locations. Each energy propagation path can be defined by a chief ray formed between one energy location of the plurality of energy locations and the energy waveguide where each energy propagation path extends from the energy waveguide in a unique direction determined at least by the one energy location. In one embodiment, the location of each energy waveguide includes a two-dimensional (2D) spatial coordinate, and where the unique direction of each energy propagation path includes a 2D angular coordinate, whereby the 2D spatial coordinate and the 2D angular coordinate form a four-dimensional (4D) coordinate set. In another embodiment, the assembly includes a mount to which the plurality of modular 4D energy-field packages are attached to form an energy-projection surface.

In one embodiment, the assembly includes the at least one of the plurality of modular 4D energy-field packages being integrated onto a chip. In another embodiment, the chip of the at least one of the plurality of modular 4D energy-field packages is a silicon chip. In one embodiment, the at least one modular 4D energy-field package further includes a border surrounding the at least one energy waveguide of the at least one modular 4D energy-field package. In one embodiment, the border of the at least one modular 4D energy-field package surrounds each energy waveguide of the at least one modular 4D energy-field package. In another embodiment, the at least one border includes a black region. In yet another embodiment, the border is able to separate the at least one energy waveguide of the plurality of modular 4D energy-field packages when attached to the mount.

In one embodiment, the distance between the distance between the at least one energy waveguide of the plurality of modular 4D energy-field packages prevents seams in the 4D energy field. In another embodiment, the plurality of 4D energy-field packages are attached to the mount to form a grid of modular 4D energy field-packages where each modular 4D energy-field package attached to the mount further includes a border that evenly separates all of the at least one energy waveguide of the plurality of 4D energy-field packages attached to the mount. In one embodiment, the border of each modular 4D energy-field package attached to the mount evenly separates each energy waveguide of the at least one energy waveguide of each modular 4D energy-field package attached to the mount.

In one embodiment, each energy waveguide of the at least one energy waveguide of at least one modular 4D energy-field package further includes an aperture where a first energy propagation path of the plurality of energy propagation paths substantially fills the aperture. In some embodiments, the at least one modular 4D energy-field package limits propagation of energy along energy propagation paths that do not extend through the aperture of any waveguide. In other embodiments, the mechanical encasement limits propagation of energy along energy propagation paths that do not extend through the aperture of any waveguide.

In one embodiment, the four-dimensional (4D) energy-field package assembly further includes a control system in communication with the plurality of modular 4D energy-field packages, where the control system is able to operate the energy-source system of the plurality of modular 4D energy-field packages to project a 4D energy field from the energy-projection surface.

In one embodiment, energy directed along at least one energy propagation path of at least one modular 4D energy-field package converges with energy directed along at least one other energy propagation path of at least one other 4D energy-field package. In another embodiment, at least one energy propagation path and the at least one other energy propagation path converge at a location on the second side of the at least one energy waveguide of the at least one modular 4D energy-field package. In yet another embodiment, at least one energy propagation path and the at least one other energy propagation path converge at a location on the first side of the at least one energy waveguide of the at least one modular 4D energy-field package.

In one embodiment, the at least one energy waveguide of at least one modular 4D energy-field package of the plurality of modular 4D energy-field packages includes a structure for directing energy, the structure being one of: (a) a structure configured to alter an angular direction of energy passing therethrough; (b) a structure having at least one numerical aperture; (c) a structure able to redirect energy off at least one internal surface; or (d) an energy relay.

In one instance, the energy-projection surface includes a planar surface. In another instance, the energy-projection surface includes a curved surface. In one embodiment, at least one modular 4D energy-field package includes a magnifying waveguide disposed on the second side of each energy waveguide of the at least one energy waveguide. In another embodiment, the energy sources of the pluralities of energy sources include one or more emissive displays. In some embodiments, the one or more emissive displays are one of LED, OLED, AMOLED, and TOLED.

In one embodiment, the 4D energy-field package assembly further includes at least one second mount to which the plurality of modular 4D energy-field packages are attached to form at least one second energy-projection surface. In one embodiment, the mount includes a printed circuit board. In some embodiments, energy directed along the pluralities of energy propagation paths of the plurality of modular 4D energy-field packages may be electromagnetic energy defined by a wavelength, the wavelength being one of: visible light, ultraviolet, infrared or x-ray. In other embodiments, energy directed along the pluralities of energy propagation paths of the plurality of modular 4D energy-field packages may be mechanical energy defined by pressure waves, the waves being one of: tactile pressure waves, acoustic sound vibrations or ultrasound waves.

In one embodiment, the 4D coordinate set of each energy propagation path uniquely identifies each energy propagation path. In another embodiment, the at least one energy waveguide of at least one modular 4D energy-field package includes a lenslet. In one embodiment, the lenslet includes a Fresnel lens. In another embodiment, a shape of the lenslet is configured to additionally alter the unique direction of each energy propagation path.

In one embodiment, the at least one energy waveguide of at least one modular 4D energy-field package includes a reflector element having a first reflector located on the first side of the energy waveguide, the first reflector having one or more aperture stops formed therethrough, and a second reflector located on the second side of the energy waveguide, the second reflector having one or more aperture stops formed therethrough.

In one embodiment, a size of the one or more aperture stops of the first and second reflectors is constant. In another embodiment, a size of the one or more aperture stops of the first and second reflectors varies. In one embodiment, the first and second reflectors include one or more parabolic surfaces, such that a first parabolic surface of the first reflector and a first parabolic surface of the second reflector are configured to reflect energy along each energy propagation path of the at least one energy waveguide.

In one embodiment, a focal length of the first parabolic surface of the first reflector is the same as a focal length of the first parabolic surface of the second reflector. In another embodiment, a focal length of the first parabolic surface of the first reflector is different than a focal length of the first parabolic surface of the second reflector.

In one embodiment, the at least one energy waveguide of each modular 4D energy-field package includes a plurality of energy waveguides. In another embodiment, light directed along a first energy propagation path of the plurality of energy propagation paths through a first energy waveguide of the plurality of energy waveguides of each modular 4D package assembly substantially fills an aperture of the first energy waveguide. In yet another embodiment, each modular 4D energy-field package further includes an energy-inhibiting element positioned to limit propagation of light along a portion of energy propagation paths of the plurality of energy propagation paths that do not extend through the aperture of the first energy waveguide. In some examples, the energy-inhibiting element is a baffle structure.

In one embodiment, the 4D energy-field package assembly further includes a mechanical encasement that surrounds each energy waveguide of the plurality of energy waveguides and the energy-source system of each modular 4D energy-field package. In some instances, the mechanical encasement limits propagation of energy along energy propagation paths that do not extend through the aperture of the first energy waveguide.

In one embodiment, each energy waveguide of the at least one energy waveguide of at least one modular 4D energy-field package includes a structure for attenuating or modifying at least one energy propagation path of each energy waveguide. In this embodiment, the structure can be selected from a group consisting of: (a) an energy blocking structure; (b) an element able to alter the at least one energy propagation path of each energy waveguide to alter a fill factor of an aperture of each energy waveguide; or (c) a structure able to limit an angular extent of energy proximate an energy location of each modular 4D energy-field package.

BRIEF DESCRIPTION OF THE DRAWINGS

FIG. 5A is a schematic diagram illustrating an example of a relayed image through multi-core optical fibers;

FIG. 5B is a schematic diagram illustrating an example of a relayed image through an optical relay that exhibits the properties of the Transverse Anderson Localization principle;

FIG. 6 is a schematic diagram showing rays propagated from an energy surface to a viewer;

FIG. 8 illustrates a front perspective view of the embodiment shown in FIG. 7;

FIG. 15 illustrates an additional embodiment which further highlights how a waveguide element may affect a spatial distribution of energy passing therethrough;

FIG. 16 illustrates an embodiment wherein the plurality of energy waveguides comprise diffractive waveguide elements;

FIG. 17 illustrates a lenslet configuration used to provide full density of ray illumination for the desired angle of view;

DETAILED DESCRIPTION

Figure 1:
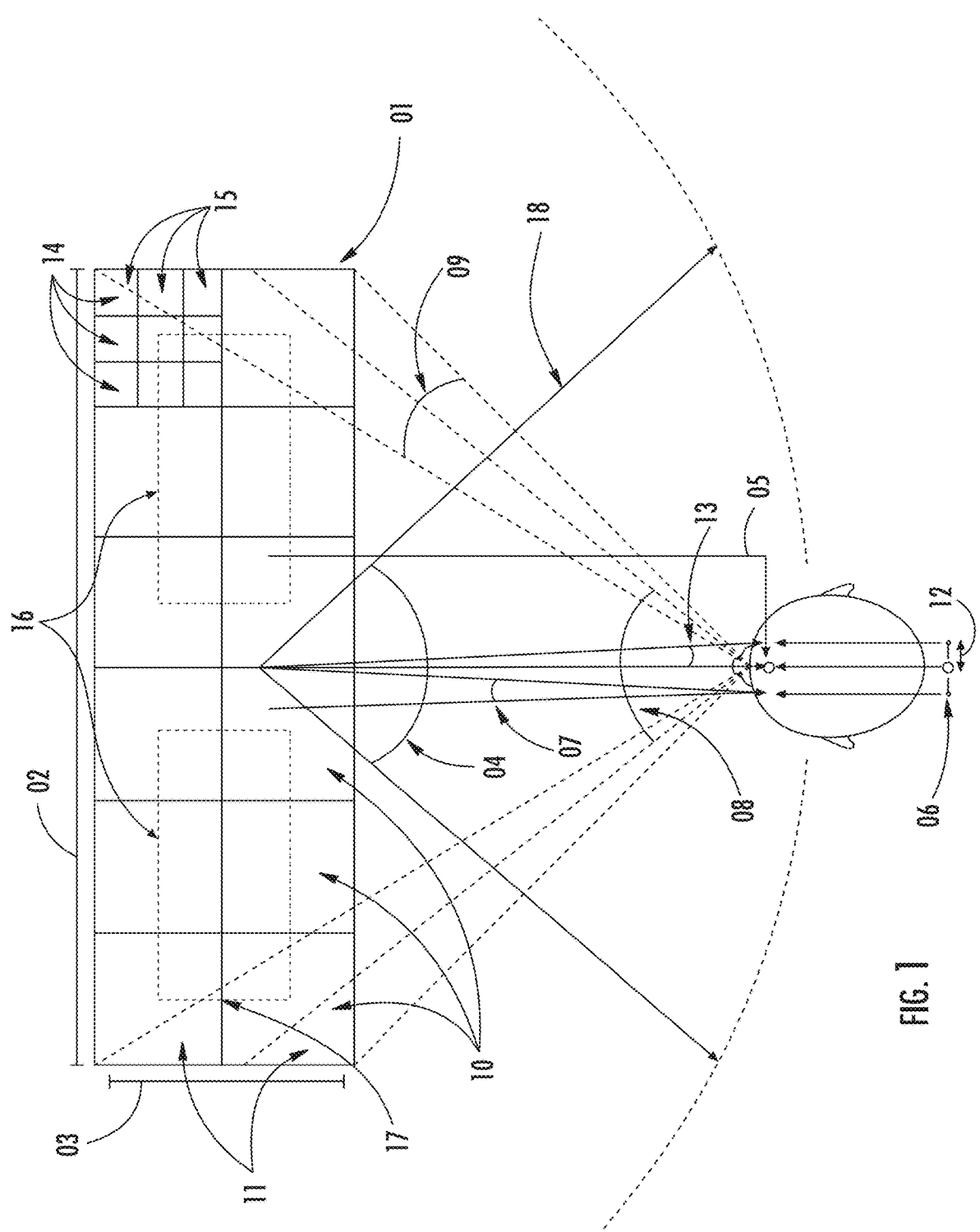
FIG. 1 is a schematic diagram illustrating design parameters for an energy directing system.

An embodiment of a Holodeck (collectively called "Holodeck Design Parameters") provide sufficient energy stimulus to fool the human sensory receptors into believing that received energy impulses within a virtual, social and interactive environment are real, providing: 1) binocular disparity without external accessories, head-mounted eyewear, or other peripherals; 2) accurate motion parallax, occlusion and opacity throughout a viewing volume simultaneously for any number of viewers; 3) visual focus through synchronous convergence, accommodation and miosis of the eye for all perceived rays of light; and 4) converging energy wave propagation of sufficient density and resolution to exceed the human sensory "resolution" for vision, hearing, touch, taste, smell, and/or balance.

Based upon conventional technology to date, we are decades, if not centuries away from a technology capable of providing for all receptive fields in a compelling way as suggested by the Holodeck Design Parameters including the visual, auditory, somatosensory, gustatory, olfactory, and vestibular systems.

In this disclosure, the terms light field and holographic may be used interchangeably to define the energy propagation for stimulation of any sensory receptor response. While initial disclosures may refer to examples of electromagnetic and mechanical energy propagation through energy surfaces for holographic imagery and volumetric haptics, all forms of sensory receptors are envisioned in this disclosure. Furthermore, the principles disclosed herein for energy propagation along propagation paths may be applicable to both energy emission and energy capture.

Many technologies exist today that are often unfortunately confused with holograms including lenticular printing, Pepper's Ghost, glasses-free stereoscopic displays, horizontal parallax displays, head-mounted VR and AR displays (HMD), and other such illusions generalized as "fauxlography." These technologies may exhibit some of the desired properties of a true holographic display; however, lack the ability to stimulate the human visual sensory response in any way sufficient to address at least two of the four identified Holodeck Design Parameters.

These challenges have not been successfully implemented by conventional technology to produce a seamless energy surface sufficient for holographic energy propagation. There are various approaches to implementing volumetric and direction multiplexed light field displays including parallax barriers, hogels, voxels, diffractive optics, multi-view projection, holographic diffusers, rotational mirrors, multilayered displays, time sequential displays, head mounted display, etc., however, conventional approaches may involve a compromise on image quality, resolution, angular sampling density, size, cost, safety, frame rate, etc., ultimately resulting in an unviable technology.

To achieve the Holodeck Design Parameters for the visual, auditory, somatosensory systems, the human acuity of each of the respective systems is studied and understood to propagate energy waves to sufficiently fool the human sensory receptors. The visual system is capable of resolving to approximately 1 arc min, the auditory system may distinguish the difference in placement as little as three degrees, and the somatosensory system at the hands are capable of discerning points separated by 2-12 mm. While there are various and conflicting ways to measure these acuities, these values are sufficient to understand the systems and methods to stimulate perception of energy propagation.

Of the noted sensory receptors, the human visual system is by far the most sensitive given that even a single photon can induce sensation. For this reason, much of this introduction will focus on visual energy wave propagation, and vastly lower resolution energy systems coupled within a disclosed energy waveguide surface may converge appropriate signals to induce holographic sensory perception. Unless otherwise noted, all disclosures apply to all energy and sensory domains.

When calculating for effective design parameters of the energy propagation for the visual system given a viewing volume and viewing distance, a desired energy surface may be designed to include many gigapixels of effective energy location density. For wide viewing volumes, or near field viewing, the design parameters of a desired energy surface may include hundreds of gigapixels or more of effective energy location density. By comparison, a desired energy source may be designed to have 1 to 250 effective megapixels of energy location density for ultrasonic propagation of volumetric haptics or an array of 36 to 3,600 effective energy locations for acoustic propagation of holographic sound depending on input environmental variables. What is important to note is that with a disclosed bidirectional energy surface architecture, all components may be configured to form the appropriate structures for any energy domain to enable holographic propagation.

However, the main challenge to enable the Holodeck today involves available visual technologies and electromagnetic device limitations. Acoustic and ultrasonic devices are less challenging given the orders of magnitude difference in desired density based upon sensory acuity in the respective receptive field, although the complexity should not be underestimated. While holographic emulsion exists with resolutions exceeding the desired density to encode interference patterns in static imagery, state-of-the-art display devices are limited by resolution, data throughput and manufacturing feasibility. To date, no singular display device has been able to meaningfully produce a light field having near holographic resolution for visual acuity.

Production of a single silicon-based device capable of meeting the desired resolution for a compelling light field display may not practical and may involve extremely complex fabrication processes beyond the current manufacturing capabilities. The limitation to tiling multiple existing display devices together involves the seams and gap formed by the physical size of packaging, electronics, enclosure, optics and a number of other challenges that inevitably result in an unviable technology from an imaging, cost and/or a size standpoint.

The embodiments disclosed herein may provide a real-world path to building the Holodeck.

Example embodiments will now be described hereinafter with reference to the accompanying drawings, which form a part hereof, and which illustrate example embodiments which may be practiced. As used in the disclosures and the appended claims, the terms "embodiment", "example embodiment", and "exemplary embodiment" do not necessarily refer to a single embodiment, although they may, and various example embodiments may be readily combined and interchanged, without departing from the scope or spirit of example embodiments. Furthermore, the terminology as used herein is for the purpose of describing example embodiments only and is not intended to be limitations. In this respect, as used herein, the term "in" may include "in" and "on", and the terms "a," "an" and "the" may include singular and plural references. Furthermore, as used herein, the term "by" may also mean "from", depending on the context. Furthermore, as used herein, the term "if" may also mean "when" or "upon," depending on the context. Furthermore, as used herein, the words "and/or" may refer to and encompass any and all possible combinations of one or more of the associated listed items.

Holographic System Considerations: Overview of Light Field Energy Propagation Resolution Light field and holographic display is the result of a plurality of projections where energy surface locations provide angular, color and intensity information propagated within a viewing volume. The disclosed energy surface provides opportunities for additional information to coexist and propagate through the same surface to induce other sensory system responses. Unlike a stereoscopic display, the viewed position of the converged energy propagation paths in space do not vary as the viewer moves around the viewing volume and any number of viewers may simultaneously see propagated objects in real-world space as if it was truly there. In some embodiments, the propagation of energy may be located in the same energy propagation path but in opposite directions. For example, energy emission and energy capture along an energy propagation path are both possible in some embodiments of the present disclosed.

FIG. 1 is a schematic diagram illustrating variables relevant for stimulation of sensory receptor response. These variables may include surface diagonal 01, surface width 02, surface height 03, a determined target seating distance 18, the target seating field of view field from the center of the display 04, the number of intermediate samples demonstrated here as samples between the eyes 05, the average adult inter-ocular separation 06, the average resolution of the human eye in arcmin 07, the horizontal field of view formed between the target viewer location and the surface width 08, the vertical field of view formed between the target viewer location and the surface height 09, the resultant horizontal waveguide element resolution, or total number of elements, across the surface 10, the resultant vertical waveguide element resolution, or total number of elements, across the surface 11, the sample distance based upon the inter-ocular spacing between the eyes and the number of intermediate samples for angular projection between the eyes 12. The angular sampling may be based upon the sample distance and the target seating distance 13, the total resolution Horizontal per waveguide element derived from the angular sampling desired 14, the total resolution Vertical per waveguide element derived from the angular sampling desired 15. Device Horizontal is the count of the determined number of discreet energy sources desired 16, and device Vertical is the count of the determined number of discreet energy sources desired 17.

A method to understand the desired minimum resolution may be based upon the following criteria to ensure sufficient stimulation of visual (or other) sensory receptor response: surface size (e.g., 84" diagonal), surface aspect ratio (e.g., 16:9), seating distance (e.g., 128" from the display), seating field of view (e.g., 120 degrees or +/−60 degrees about the center of the display), desired intermediate samples at a distance (e.g., one additional propagation path between the eyes), the average inter-ocular separation of an adult (approximately 65 mm), and the average resolution of the human eye (approximately 1 arcmin). These example values should be considered placeholders depending on the specific application design parameters.

Further, each of the values attributed to the visual sensory receptors may be replaced with other systems to determine desired propagation path parameters. For other energy propagation embodiments, one may consider the auditory system's angular sensitivity as low as three degrees and the somatosensory system's spatial resolution of the hands as small as 2-12 mm.

While there are various and conflicting ways to measure these sensory acuities, these values are sufficient to understand the systems and methods to stimulate perception of virtual energy propagation. There are many ways to consider the design resolution, and the below proposed methodology combines pragmatic product considerations with the biological resolving limits of the sensory systems. As will be appreciated by one of ordinary skill in the art, the following overview is a simplification of any such system design, and should be considered for exemplary purposes only.

With the resolution limit of the sensory system understood, the total energy waveguide element density may be calculated such that the receiving sensory system cannot discern a single energy waveguide element from an adjacent element, given:

$$\text{Surface Aspect Ratio} = \frac{\text{Width }(W)}{\text{Height }(H)}$$

$$\text{Surface Horizontal Size} = \text{Surface Diagonal} * \left(\frac{1}{\sqrt{\left(1 + \left(\frac{H}{W}\right)^2\right)}}\right)$$

$$\text{Surface Vertical Size} = \text{Surface Diagonal} * \left(\frac{1}{\sqrt{1 + \left(\frac{W}{H}\right)^2}}\right)$$

$$\text{Horizontal Field of View} = 2 * \text{atan}\left(\frac{\text{Surface Horizontal Size}}{2 * \text{Seating Distance}}\right)$$

$$\text{Vertical Field of View} = 2 * \text{atan}\left(\frac{\text{Surface Verticle Size}}{2 * \text{Seating Distance}}\right)$$

$$\text{Horizontal Element Resolution} = \text{Horizontal } FoV * \frac{60}{\text{Eye Resolution}}$$

$$\text{Vertical Element Resolution} = \text{Vertical } FoV * \frac{60}{\text{Eye Resolution}}$$

The above calculations result in approximately a 32×18° field of view resulting in approximately 1920×1080 (rounded to nearest format) energy waveguide elements being desired. One may also constrain the variables such that the field of view is consistent for both (u, v) to provide a more regular spatial sampling of energy locations (e.g. pixel aspect ratio). The angular sampling of the system assumes a defined target viewing volume location and additional propagated energy paths between two points at the optimized distance, given:

$$\text{Sample Distance} = \frac{\text{Inter-Ocular Distance}}{(\text{Number of Desired Intermediate Samples} + 1)}$$

$$\text{Angular Sampling} = \text{atan}\left(\frac{\text{Sample Distance}}{\text{Seating Distance}}\right)$$

In this case, the inter-ocular distance is leveraged to calculate the sample distance although any metric may be leveraged to account for appropriate number of samples as a given distance. With the above variables considered, approximately one ray per 0.57° may be desired and the total system resolution per independent sensory system may be determined, given:

$$\text{Locations Per Element}(N) = \frac{\text{Seating } FoV}{\text{Angular Sampling}}$$

$$\text{Total Resolution } H = N * \text{Horizontal Element Resolution}$$

$$\text{Total Resolution } V = N * \text{Vertical Element Resolution}$$

With the above scenario given the size of energy surface and the angular resolution addressed for the visual acuity system, the resultant energy surface may desirably include approximately 400 k×225 k pixels of energy resolution locations, or 90 gigapixels holographic propagation density. These variables provided are for exemplary purposes only and many other sensory and energy metrology considerations should be considered for the optimization of holographic propagation of energy. In an additional embodiment, 1 gigapixel of energy resolution locations may be desired based upon the input variables. In an additional embodiment, 1,000 gigapixels of energy resolution locations may be desired based upon the input variables.

Figure 2:
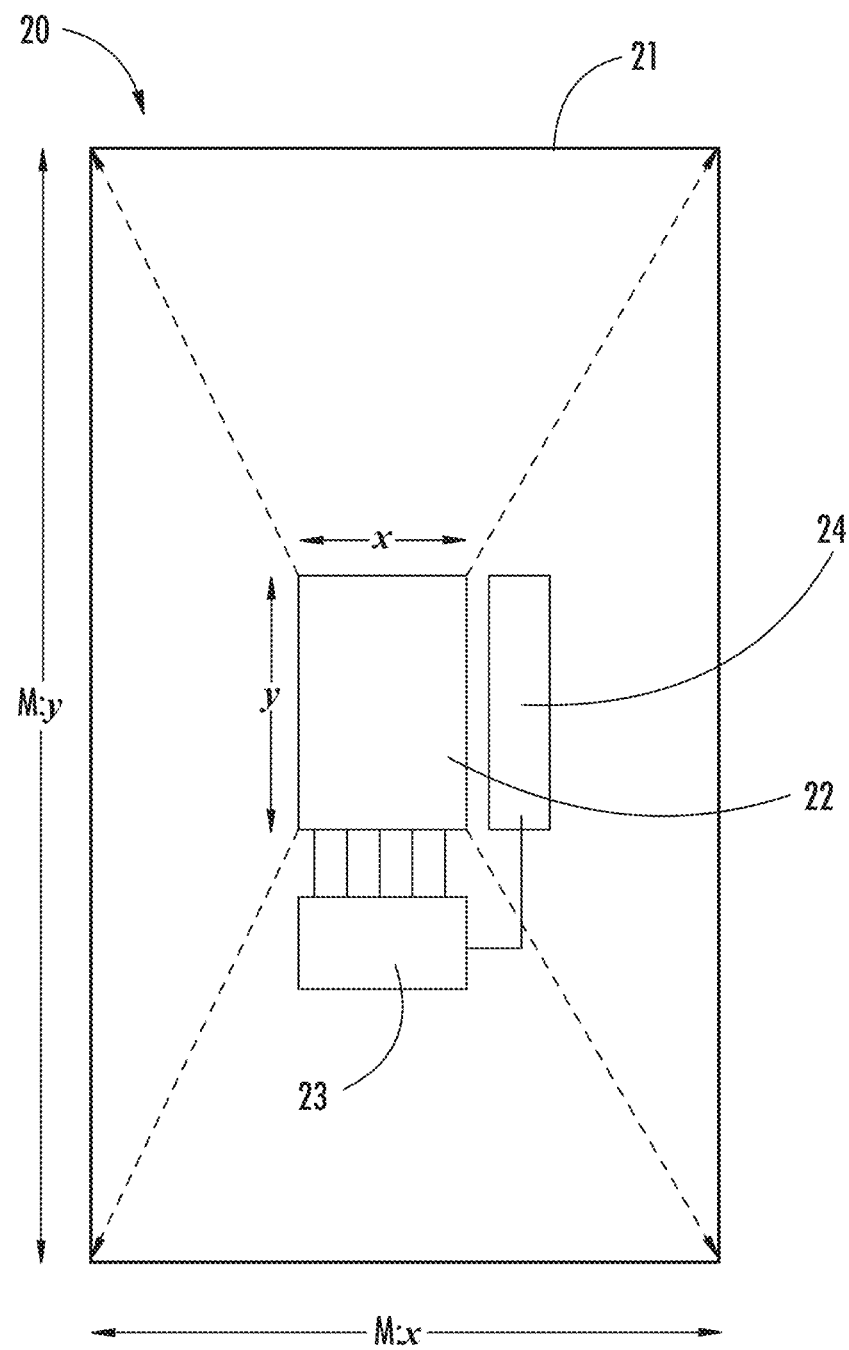
FIG. 2 is a schematic diagram illustrating an energy system having an active device area with a mechanical envelope.

Current Technology Limitations: Active Area, Device Electronics, Packaging, and the Mechanical Envelope FIG. 2 illustrates a device 20 having an active area 22 with a certain mechanical form factor. The device 20 may include drivers 23 and electronics 24 for powering and interface to the active area 22, the active area having a dimension as shown by the x and y arrows. This device 20 does not take into account the cabling and mechanical structures to drive, power and cool components, and the mechanical footprint may be further minimized by introducing a flex cable into the device 20. The minimum footprint for such a device 20 may also be referred to as a mechanical envelope 21 having a dimension as shown by the M:x and M:y arrows. This device 20 is for illustration purposes only and custom electronics designs may further decrease the mechanical envelope overhead, but in almost all cases may not be the exact size of the active area of the device. In an embodiment, this device 20 illustrates the dependency of electronics as it relates to active image area 22 for a micro OLED, DLP chip or LCD panel, or any other technology with the purpose of image illumination.

In some embodiments, it may also be possible to consider other projection technologies to aggregate multiple images onto a larger overall display. However, this may come at the cost of greater complexity for throw distance, minimum focus, optical quality, uniform field resolution, chromatic aberration, thermal properties, calibration, alignment, additional size or form factor. For most practical applications, hosting tens or hundreds of these projection sources 20 may result in a design that is much larger with less reliability.

For exemplary purposes only, assuming energy devices with an energy location density of 3840×2160 sites, one may determine the number of individual energy devices (e.g., device 10) desired for an energy surface, given:

$$\text{Devices } H = \frac{\text{Total Resolution } H}{\text{Device Resolution } H}$$

$$\text{Devices } V = \frac{\text{Total Resolution } V}{\text{Device Resolution } V}$$

Given the above resolution considerations, approximately 105×105 devices similar to those shown in FIG. 2 may be desired. It should be noted that many devices consist of various pixel structures that may or may not map to a regular grid. In the event that there are additional sub-pixels or locations within each full pixel, these may be exploited to generate additional resolution or angular density. Additional signal processing may be used to determine how to convert the light field into the correct (u, v) coordinates depending on the specified location of the pixel structure(s) and can be an explicit characteristic of each device that is known and calibrated. Further, other energy domains may involve a different handling of these ratios and device structures, and those skilled in the art will understand the direct intrinsic relationship between each of the desired frequency domains. This will be shown and discussed in more detail in subsequent disclosure.

The resulting calculation may be used to understand how many of these individual devices may be desired to produce a full resolution energy surface. In this case, approximately 105×105 or approximately 11,080 devices may be desired to achieve the visual acuity threshold. The challenge and novelty exists within the fabrication of a seamless energy surface from these available energy locations for sufficient sensory holographic propagation.

Summary of Seamless Energy Surfaces: Configurations and Designs for Arrays of Energy Relays In some embodiments, approaches are disclosed to address the challenge of generating high energy location density from an array of individual devices without seams due to the limitation of mechanical structure for the devices. In an embodiment, an energy propagating relay system may allow for an increase the effective size of the active device area to meet or exceed the mechanical dimensions to configure an array of relays and form a singular seamless energy surface.

Figure 3:
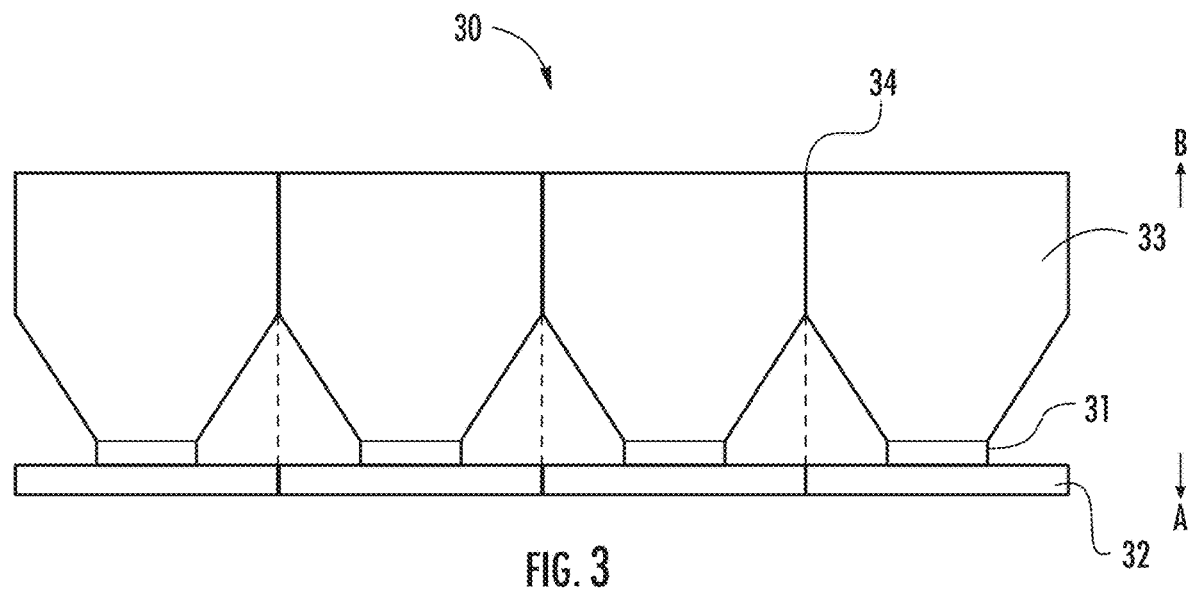
FIG. 3 is a schematic diagram illustrating an energy relay system.

FIG. 3 illustrates an embodiment of such an energy relay system 30. As shown, the relay system 30 may include a device 31 mounted to a mechanical envelope 32, with an energy relay element 33 propagating energy from the device 31. The relay element 33 may be configured to provide the ability to mitigate any gaps 34 that may be produced when multiple mechanical envelopes 32 of the device are placed into an array of multiple devices 31.

For example, if a device's active area 310 is 20 mm×10 mm and the mechanical envelope 32 is 40 mm×20 mm, an energy relay element 33 may be designed with a magnification of 2:1 to produce a tapered form that is approximately 20 mm×10 mm on a minified end (arrow A) and 40 mm×20 mm on a magnified end (arrow B), providing the ability to align an array of these elements 33 together seamlessly without altering or colliding with the mechanical envelope 32 of each device 31. Mechanically, the relay elements 33 may be bonded or fused together to align and polish ensuring minimal seam gap 34 between devices 31. In one such embodiment, it is possible to achieve a seam gap 34 smaller than the visual acuity limit of the eye.

Figure 4:
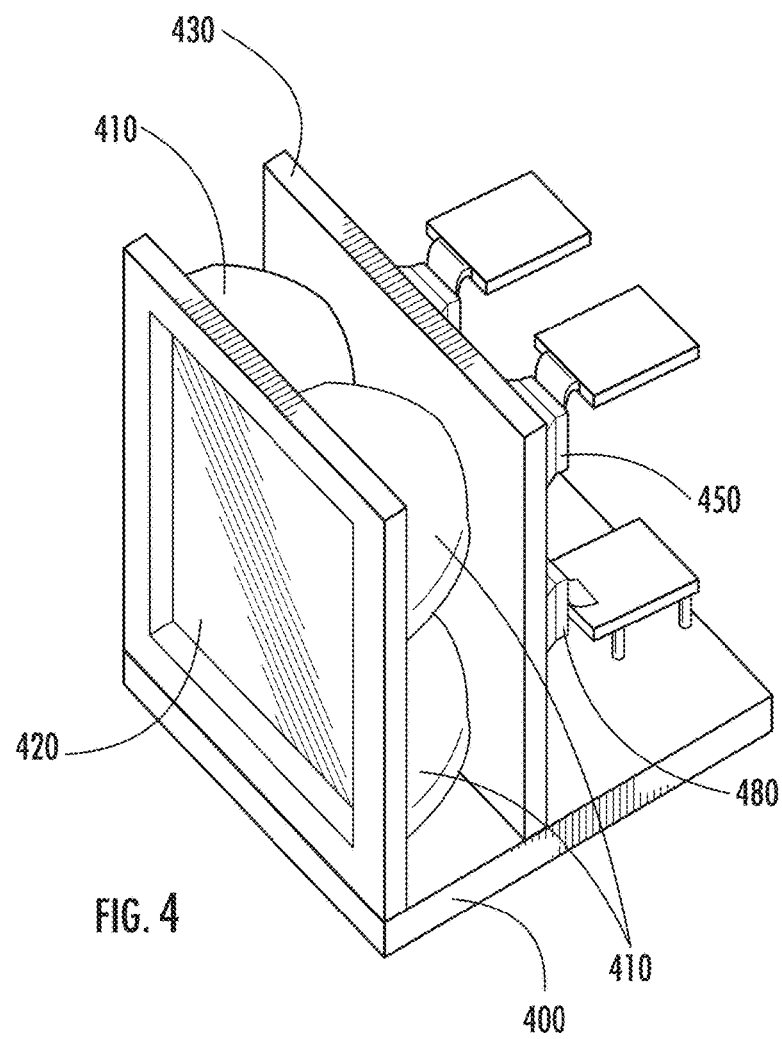
FIG. 4 is a schematic diagram illustrating an embodiment of energy relay elements adhered together and fastened to a base structure.

FIG. 4 illustrates an example of a base structure 400 having energy relay elements 410 formed together and securely fastened to an additional mechanical structure 430. The mechanical structure of the seamless energy surface 420 provides the ability to couple multiple energy relay elements 410, 450 in series to the same base structure through bonding or other mechanical processes to mount relay elements 410, 450. In some embodiments, each relay element 410 may be fused, bonded, adhered, pressure fit, aligned or otherwise attached together to form the resultant seamless energy surface 420. In some embodiments, a device 480 may be mounted to the rear of the relay element 410 and aligned passively or actively to ensure appropriate energy location alignment within the determined tolerance is maintained.

In an embodiment, the seamless energy surface comprises one or more energy locations and one or more energy relay element stacks comprise a first and second side and each energy relay element stack is arranged to form a singular seamless display surface directing energy along propagation paths extending between one or more energy locations and the seamless display surface, and where the separation between the edges of any two adjacent second sides of the terminal energy relay elements is less than the minimum perceptible contour as defined by the visual acuity of a human eye having better than 20/40 vision at a distance greater than the width of the singular seamless display surface.

In an embodiment, each of the seamless energy surfaces comprise one or more energy relay elements each with one or more structures forming a first and second surface with a transverse and longitudinal orientation. The first relay surface has an area different than the second resulting in positive or negative magnification and configured with explicit surface contours for both the first and second surfaces passing energy through the second relay surface to substantially fill a +/−10 degree angle with respect to the normal of the surface contour across the entire second relay surface.

In an embodiment, multiple energy domains may be configured within a single, or between multiple energy relays to direct one or more sensory holographic energy propagation paths including visual, acoustic, tactile or other energy domains.

In an embodiment, the seamless energy surface is configured with energy relays that comprise two or more first sides for each second side to both receive and emit one or more energy domains simultaneously to provide bidirectional energy propagation throughout the system.

In an embodiment, the energy relays are provided as loose coherent elements.

Introduction to Component Engineered Structures: Disclosed Advances in Transverse Anderson Localization Energy Relays The properties of energy relays may be significantly optimized according to the principles disclosed herein for energy relay elements that induce Transverse Anderson Localization. Transverse Anderson Localization is the propagation of a ray transported through a transversely disordered but longitudinally consistent material.

This implies that the effect of the materials that produce the Anderson Localization phenomena may be less impacted by total internal reflection than by the randomization between multiple-scattering paths where wave interference can completely limit the propagation in the transverse orientation while continuing in the longitudinal orientation.

Of significant additional benefit is the elimination of the cladding of traditional multi-core optical fiber materials. The cladding is to functionally eliminate the scatter of energy between fibers, but simultaneously act as a barrier to rays of energy thereby reducing transmission by at least the core to clad ratio (e.g., a core to clad ratio of 70:30 will transmit at best 70% of received energy transmission) and additionally forms a strong pixelated patterning in the propagated energy.

FIG. 5A illustrates an end view of an example of one such non-Anderson Localization energy relay 500, wherein an image is relayed through multi-core optical fibers where pixilation and fiber noise may be exhibited due to the intrinsic properties of the optical fibers. With traditional multi-mode and multi-core optical fibers, relayed images may be intrinsically pixelated due to the properties of total internal reflection of the discrete array of cores where any cross-talk between cores will reduce the modulation transfer function and increase blurring. The resulting imagery produced with traditional multi-core optical fiber tends to have a residual fixed noise fiber pattern similar to those shown in FIG. 3.

FIG. 5B, illustrates an example of the same relayed image 550 through an energy relay comprising materials that exhibit the properties of Transverse Anderson Localization, where the relayed pattern has a greater density grain structures as compared to the fixed fiber pattern from FIG. 5A. In an embodiment, relays comprising randomized microscopic component engineered structures induce Transverse Anderson Localization and transport light more efficiently with higher propagation of resolvable resolution than commercially available multi-mode glass optical fibers.

There is significant advantage to the Transverse Anderson Localization material properties in terms of both cost and weight, where a similar optical grade glass material, may cost and weigh upwards of 10 to 100-fold more than the cost for the same material generated within an embodiment, wherein disclosed systems and methods comprise randomized microscopic component engineered structures demonstrating significant opportunities to improve both cost and quality over other technologies known in the art.

In an embodiment, a relay element exhibiting Transverse Anderson Localization may comprise a plurality of at least two different component engineered structures in each of three orthogonal planes arranged in a dimensional lattice and the plurality of structures form randomized distributions of material wave propagation properties in a transverse plane within the dimensional lattice and channels of similar values of material wave propagation properties in a longitudinal plane within the dimensional lattice, wherein localized energy waves propagating through the energy relay have higher transport efficiency in the longitudinal orientation versus the transverse orientation.

In an embodiment, multiple energy domains may be configured within a single, or between multiple Transverse Anderson Localization energy relays to direct one or more sensory holographic energy propagation paths including visual, acoustic, tactile or other energy domains.

In an embodiment, the seamless energy surface is configured with Transverse Anderson Localization energy relays that comprise two or more first sides for each second side to both receive and emit one or more energy domains simultaneously to provide bidirectional energy propagation throughout the system.

In an embodiment, the Transverse Anderson Localization energy relays are configured as loose coherent or flexible energy relay elements.

Considerations for 4D Plenoptic Functions:
Selective Propagation of Energy Through
Holographic Waveguide Arrays As discussed above and herein throughout, a light field display system generally includes an energy source (e.g., illumination source) and a seamless energy surface configured with sufficient energy location density as articulated in the above discussion. A plurality of relay elements may be used to relay energy from the energy devices to the seamless energy surface. Once energy has been delivered to the seamless energy surface with the requisite energy location density, the energy can be propagated in accordance with a 4D plenoptic function through a disclosed energy waveguide system. As will be appreciated by one of ordinary skill in the art, a 4D plenoptic function is well known in the art and will not be elaborated further herein.

The energy waveguide system selectively propagates energy through a plurality of energy locations along the seamless energy surface representing the spatial coordinate of the 4D plenoptic function with a structure configured to alter an angular direction of the energy waves passing through representing the angular component of the 4D plenoptic function, wherein the energy waves propagated may converge in space in accordance with a plurality of propagation paths directed by the 4D plenoptic function.

Reference is now made to FIG. 6 illustrating an example of light field energy surface in 4D image space in accordance with a 4D plenoptic function. The figure shows ray traces of an energy surface 600 to a viewer 620 in describing how the rays of energy converge in space 630 from various positions within the viewing volume. As shown, each waveguide element 610 defines four dimensions of information describing energy propagation 640 through the energy surface 600. Two spatial dimensions (herein referred to as x and y) are the physical plurality of energy locations that can be viewed in image space, and the angular components theta and phi (herein referred to as u and v), which is viewed in virtual space when projected through the energy waveguide array. In general, and in accordance with a 4D plenoptic function, the plurality of waveguides (e.g., lenslets) are able to direct an energy location from the x, y dimension to a unique location in virtual space, along a direction defined by the u, v angular component, in forming the holographic or light field system described herein.

However, one skilled in the art will understand that a significant challenge to light field and holographic display technologies arises from uncontrolled propagation of energy due designs that have not accurately accounted for any of diffraction, scatter, diffusion, angular direction, calibration, focus, collimation, curvature, uniformity, element crosstalk, as well as a multitude of other parameters that contribute to decreased effective resolution as well as an inability to accurately converge energy with sufficient fidelity.

In an embodiment, an approach to selective energy propagation for addressing challenges associated with holographic display may include energy-inhibiting elements and substantially filling waveguide apertures with near-collimated energy into an environment defined by a 4D plenoptic function.

In an embodiment, an array of energy waveguides may define a plurality of energy propagation paths for each waveguide element configured to extend through and substantially fill the waveguide element's effective aperture in unique directions defined by a prescribed 4D function to a plurality of energy locations along a seamless energy surface inhibited by one or more elements positioned to limit propagation of each energy location to only pass through a single waveguide element.

In an embodiment, multiple energy domains may be configured within a single, or between multiple energy waveguides to direct one or more sensory holographic energy propagations including visual, acoustic, tactile or other energy domains.

In an embodiment, the energy waveguides and seamless energy surface are configured to both receive and emit one or more energy domains to provide bidirectional energy propagation throughout the system.

In an embodiment, the energy waveguides are configured to propagate non-linear or non-regular distributions of energy, including non-transmitting void regions, leveraging digitally encoded, diffractive, refractive, reflective, grin, holographic, Fresnel, or the like waveguide configurations for any seamless energy surface orientation including wall, table, floor, ceiling, room, or other geometry based environments. In an additional embodiment, an energy waveguide element may be configured to produce various geometries that provide any surface profile and/or tabletop viewing allowing users to view holographic imagery from all around the energy surface in a 360-degree configuration.

In an embodiment, the energy waveguide array elements may be reflective surfaces and the arrangement of the elements may be hexagonal, square, irregular, semi-regular, curved, non-planar, spherical, cylindrical, tilted regular, tilted irregular, spatially varying and/or multi-layered.

For any component within the seamless energy surface, waveguide, or relay components may include, but not limited to, optical fiber, silicon, glass, polymer, optical relays, diffractive, holographic, refractive, or reflective elements, optical face plates, energy combiners, beam splitters, prisms, polarization elements, spatial light modulators, active pixels, liquid crystal cells, transparent displays, or any similar materials exhibiting Anderson localization or total internal reflection.

Realizing the Holodeck: Aggregation of Bidirectional Seamless Energy Surface Systems to Stimulate Human Sensory Receptors within Holographic Environments It is possible to construct large-scale environments of seamless energy surface systems by tiling, fusing, bonding, attaching, and/or stitching multiple seamless energy surfaces together forming arbitrary sizes, shapes, contours or form-factors including entire rooms. Each energy surface system may comprise an assembly having a base structure, energy surface, relays, waveguide, devices, and electronics, collectively configured for bidirectional holographic energy propagation, emission, reflection, or sensing.

In an embodiment, an environment of tiled seamless energy systems are aggregated to form large seamless planar or curved walls including installations comprising up to all surfaces in a given environment, and configured as any combination of seamless, discontinuous planar, faceted, curved, cylindrical, spherical, geometric, or non-regular geometries.

In an embodiment, aggregated tiles of planar surfaces form wall-sized systems for theatrical or venue-based holographic entertainment. In an embodiment, aggregated tiles of planar surfaces cover a room with four to six walls including both ceiling and floor for cave-based holographic installations. In an embodiment, aggregated tiles of curved surfaces produce a cylindrical seamless environment for immersive holographic installations. In an embodiment, aggregated tiles of seamless spherical surfaces form a holographic dome for immersive Holodeck-based experiences.

In an embodiment, aggregates tiles of seamless curved energy waveguides provide mechanical edges following the precise pattern along the boundary of energy-inhibiting elements within the energy waveguide structure to bond, align, or fuse the adjacent tiled mechanical edges of the adjacent waveguide surfaces, resulting in a modular and seamless energy waveguide system.

In a further embodiment of an aggregated tiled environment, energy is propagated bidirectionally for multiple simultaneous energy domains. In an additional embodiment, the energy surface provides the ability to both display and capture simultaneously from the same energy surface with waveguides designed such that light field data may be projected by an illumination source through the waveguide and simultaneously received through the same energy surface. In an additional embodiment, additional depth sensing and active scanning technologies may be leveraged to allow for the interaction between the energy propagation and the viewer in correct world coordinates. In an additional embodiment, the energy surface and waveguide are operable to emit, reflect or converge frequencies to induce tactile sensation or volumetric haptic feedback. In some embodiments, any combination of bidirectional energy propagation and aggregated surfaces are possible.

In an embodiment, the system comprises an energy waveguide capable of bidirectional emission and sensing of energy through the energy surface with one or more energy devices independently paired with two-or-more-path energy combiners to pair at least two energy devices to the same portion of the seamless energy surface, or one or more energy devices are secured behind the energy surface, proximate to an additional component secured to the base structure, or to a location in front and outside of the FOV of the waveguide for off-axis direct or reflective projection or sensing, and the resulting energy surface provides for bidirectional transmission of energy allowing the waveguide to converge energy, a first device to emit energy and a second device to sense energy, and where the information is processed to perform computer vision related tasks including, but not limited to, 4D plenoptic eye and retinal tracking or sensing of interference within propagated energy patterns, depth estimation, proximity, motion tracking, image, color, or sound formation, or other energy frequency analysis. In an additional embodiment, the tracked positions actively calculate and modify positions of energy based upon the interference between the bidirectional captured data and projection information.

In some embodiments, a plurality of combinations of three energy devices comprising an ultrasonic sensor, a visible electromagnetic display, and an ultrasonic emitting device are configured together for each of three first relay surfaces propagating energy combined into a single second energy relay surface with each of the three first surfaces comprising engineered properties specific to each device's energy domain, and two engineered waveguide elements configured for ultrasonic and electromagnetic energy respectively to provide the ability to direct and converge each device's energy independently and substantially unaffected by the other waveguide elements that are configured for a separate energy domain.

In some embodiments, disclosed is a calibration procedure to enable efficient manufacturing to remove system artifacts and produce a geometric mapping of the resultant energy surface for use with encoding/decoding technologies as well as dedicated integrated systems for the conversion of data into calibrated information appropriate for energy propagation based upon the calibrated configuration files.

In some embodiments, additional energy waveguides in series and one or more energy devices may be integrated into a system to produce opaque holographic pixels.

In some embodiments, additional waveguide elements may be integrated comprising energy-inhibiting elements, beam-splitters, prisms, active parallax barriers or polarization technologies in order to provide spatial and/or angular resolutions greater than the diameter of the waveguide or for other super-resolution purposes.

In some embodiments, the disclosed energy system may also be configured as a wearable bidirectional device, such as virtual reality (VR) or augmented reality (AR). In other embodiments, the energy system may include adjustment optical element(s) that cause the displayed or received energy to be focused proximate to a determined plane in space for a viewer. In some embodiments, the waveguide array may be incorporated to holographic head-mounted-display. In other embodiments, the system may include multiple optical paths to allow for the viewer to see both the energy system and a real-world environment (e.g., transparent holographic display). In these instances, the system may be presented as near field in addition to other methods.

In some embodiments, the transmission of data comprises encoding processes with selectable or variable compression ratios that receive an arbitrary dataset of information and metadata; analyze said dataset and receive or assign material properties, vectors, surface IDs, new pixel data forming a more sparse dataset, and wherein the received data may comprise: 2D, stereoscopic, multi-view, metadata, light field, holographic, geometry, vectors or vectorized metadata, and an encoder/decoder may provide the ability to convert the data in real-time or off-line comprising image processing for: 2D; 2D plus depth, metadata or other vectorized information; stereoscopic, stereoscopic plus depth, metadata or other vectorized information; multi-view; multi-view plus depth, metadata or other vectorized information; holographic; or light field content; through depth estimation algorithms, with or without depth metadata; and an inverse ray tracing methodology appropriately maps the resulting converted data produced by inverse ray tracing from the various 2D, stereoscopic, multi-view, volumetric, light field or holographic data into real world coordinates through a characterized 4D plenoptic function. In these embodiments, the total data transmission desired may be multiple orders of magnitudes less transmitted information than the raw light field dataset.

Selective Propagation of Energy in Light Field and Holographic Waveguide Arrays

Figure 7:
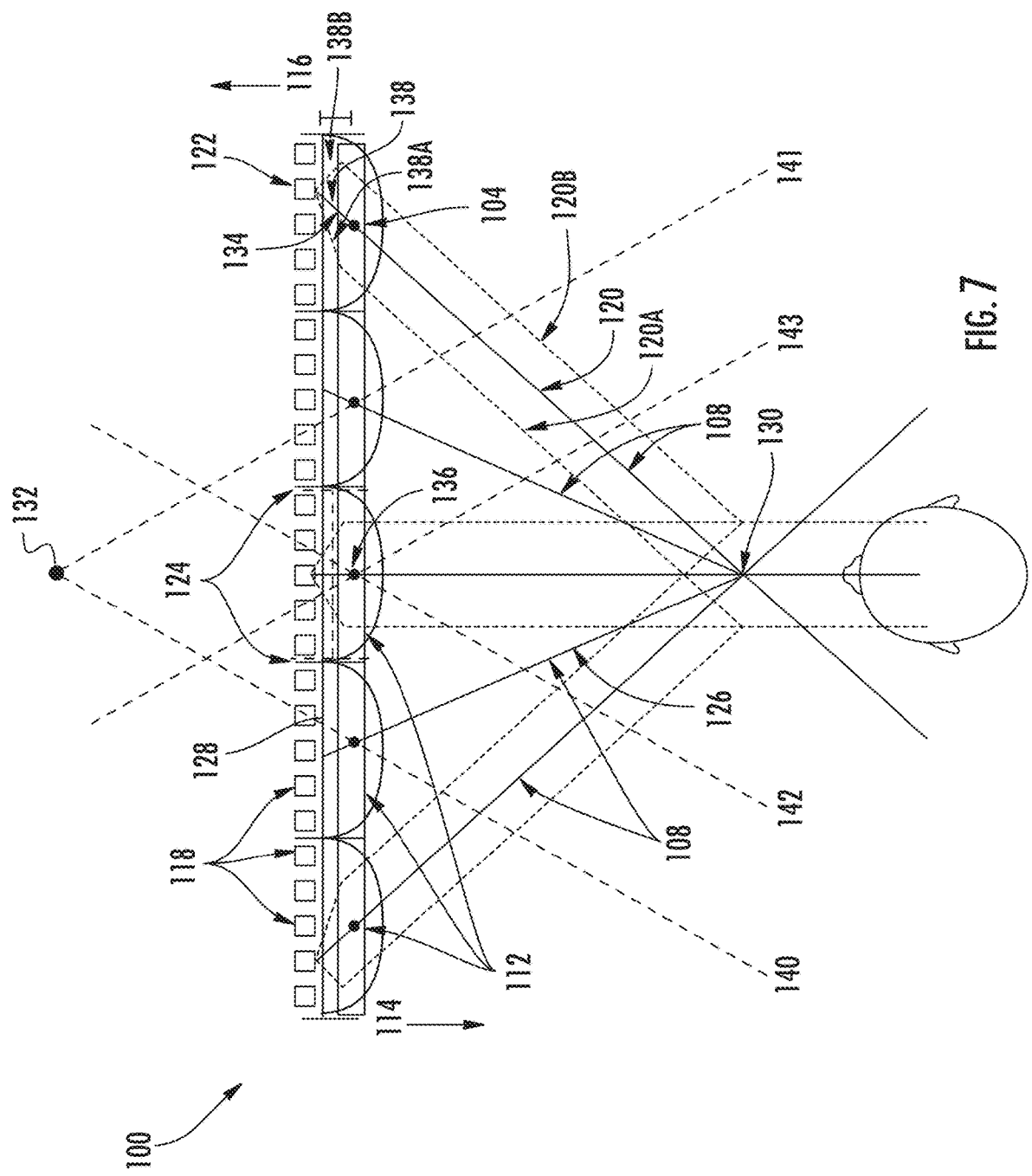
FIG. 7 illustrates a top-down perspective view of an embodiment of an energy waveguide system operable to define a plurality of energy propagation paths.

FIG. 7 illustrates a top-down perspective view of an embodiment of an energy waveguide system 100 operable to define a plurality of energy propagation paths 108. Energy waveguide system 100 comprises an array of energy waveguides 112 configured to direct energy therethrough along the plurality of energy propagation paths 108. In an embodiment, the plurality of energy propagation paths 108 extend through a plurality of locations 118 on a first side of the array 116 to a second side of the array 114.

Figure 9A:
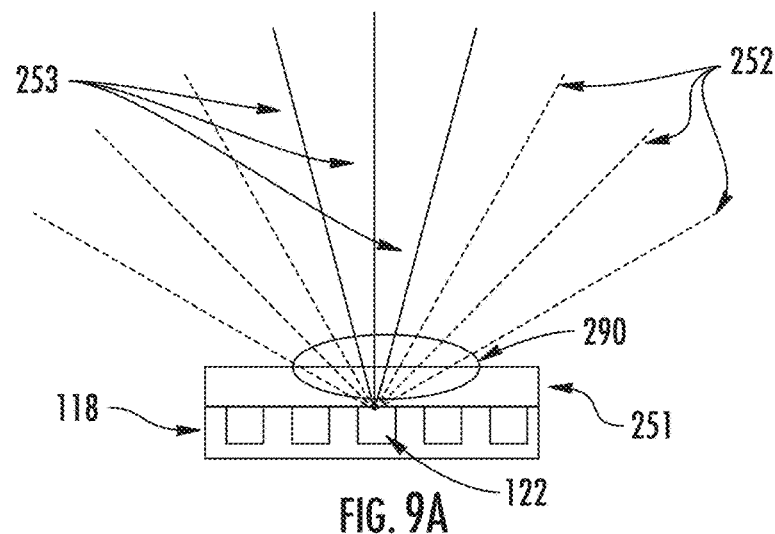
FIGS. 9A-H illustrate various embodiments of an energy-inhibiting element.
Figure 9B:
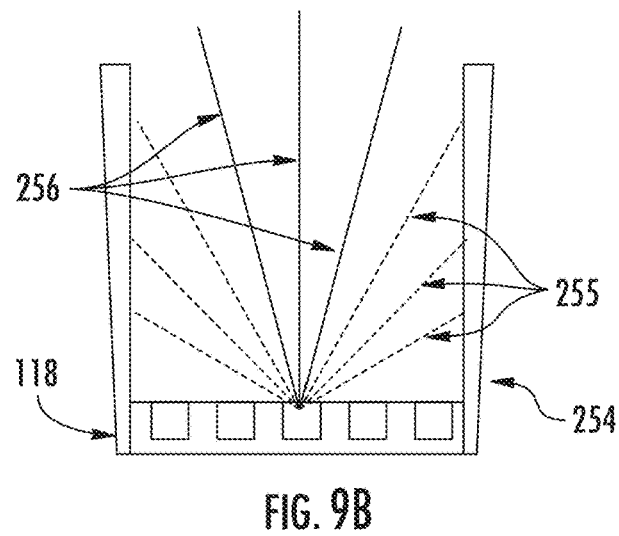
Figure 9C:
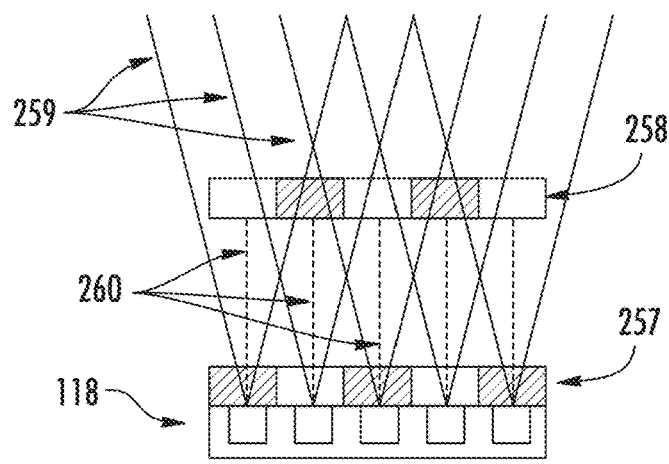
Figure 9D:
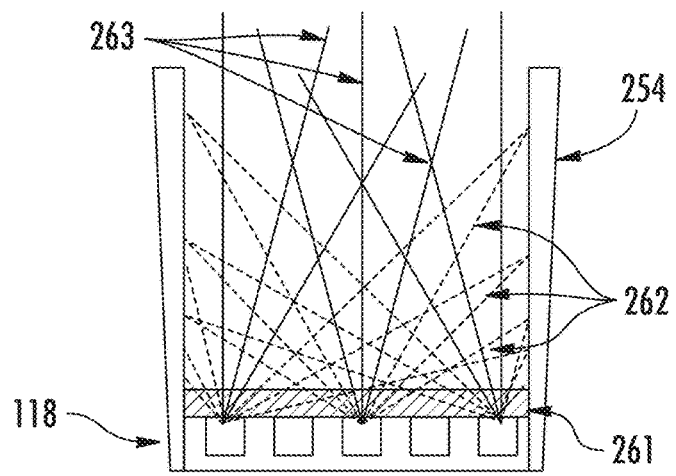
Figure 9E:
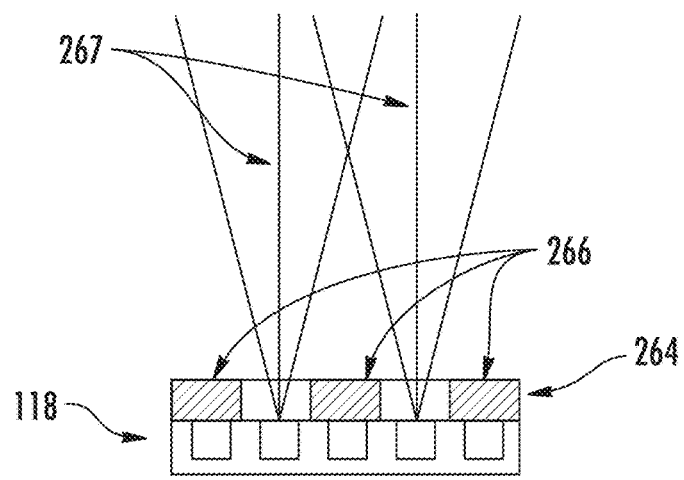
Figure 9F:
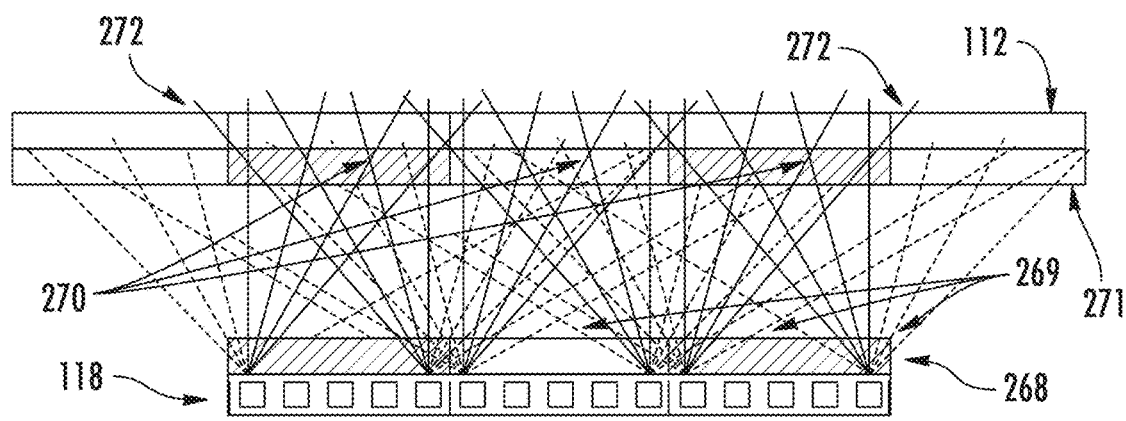
Figure 9G:
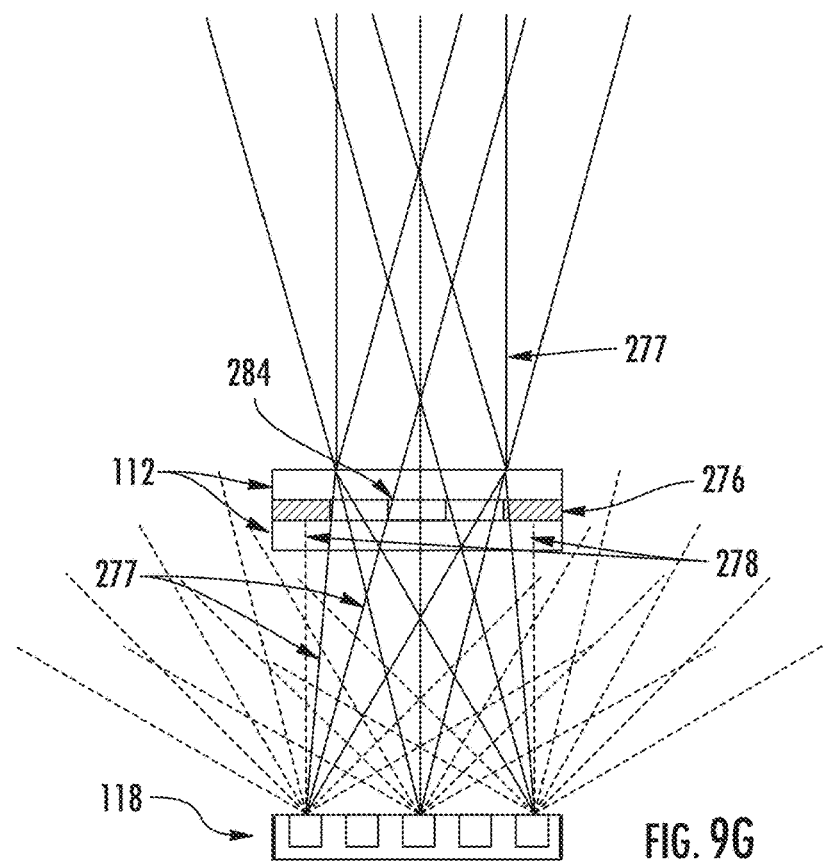
Figure 9H:
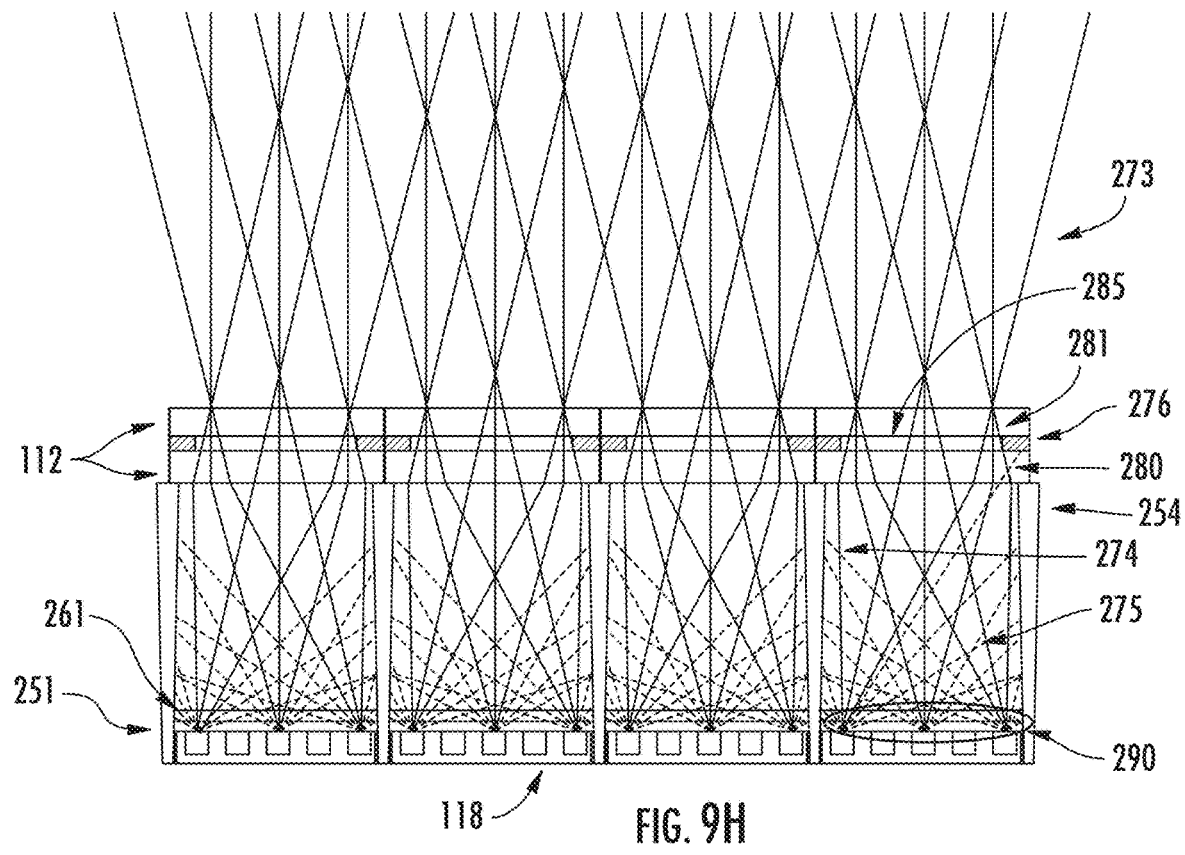

Referring to FIG. 7 and FIG. 9H, in an embodiment, a first subset 290 of the plurality of energy propagation paths 108 extend through a first energy location 122. The first energy waveguide 104 is configured to direct energy along a first energy propagation path 120 of the first subset 290 of the plurality of energy propagation paths 108. The first energy propagation path 120 may be defined by a first chief ray 138 formed between the first energy location 122 and the first energy waveguide 104. The first energy propagation path 120 may comprise rays 138A and 138B, formed between the first energy location 122 and the first energy waveguide 104, which are directed by first energy waveguide 104 along energy propagation paths 120A and 120B, respectively. The first energy propagation path 120 may extend from the first energy waveguide 104 towards the second side of the array 114. In an embodiment, energy directed along the first energy propagation path 120 comprises one or more energy propagation paths between or including energy propagation paths 120A and 120B, which are directed through the first energy waveguide 104 in a direction that is substantially parallel to the angle propagated through the second side 114 by the first chief ray 138.

Embodiments may be configured such that energy directed along the first energy propagation path 120 may exit the first energy waveguide 104 in a direction that is substantially parallel to energy propagation paths 120A and 120B and to the first chief ray 138. It may be assumed that an energy propagation path extending through an energy waveguide element 112 on the second side 114 comprises a plurality of energy propagation paths of a substantially similar propagation direction.

FIG. 8 is a front view illustration of an embodiment of energy waveguide system 100. The first energy propagation path 120 may extend towards the second side of the array 114 in a unique direction 208 extending from the first energy waveguide 104, which is determined at least by the first energy location 122. The first energy waveguide 104 may be defined by a spatial coordinate 204, and the unique direction 208 which is determined at least by first energy location 122 may be defined by an angular coordinate 206 defining the directions of the first energy propagation path 120. The spatial coordinate 204 and the angular coordinate 206 may form a four-dimensional plenoptic coordinate set 210 which defines the unique direction 208 of the first energy propagation path 120.

In an embodiment, energy directed along the first energy propagation path 120 through the first energy waveguide 104 substantially fills a first aperture 134 of the first energy waveguide 104, and propagates along one or more energy propagation paths which lie between energy propagation paths 120A and 120B and are parallel to the direction of the first energy propagation path 120. In an embodiment, the one or more energy propagation paths that substantially fill the first aperture 134 may comprise greater than 50% of the first aperture 134 diameter.

In a preferred embodiment, energy directed along the first energy propagation path 120 through the first energy waveguide 104 which substantially fills the first aperture 134 may comprise between 50% to 80% of the first aperture 134 diameter.

Turning back to FIGS. 7 and 9A-H, in an embodiment, the energy waveguide system 100 may further comprise an energy-inhibiting element 124 positioned to limit propagation of energy between the first side 116 and the second side 114 and to inhibit energy propagation between adjacent waveguides 112. In an embodiment, the energy-inhibiting element is configured to inhibit energy propagation along a portion of the first subset 290 of the plurality of energy propagation paths 108 that do not extend through the first aperture 134. In an embodiment, the energy-inhibiting element 124 may be located on the first side 116 between the array of energy waveguides 112 and the plurality of energy locations 118. In an embodiment, the energy-inhibiting element 124 may be located on the second side 114 between the plurality of energy locations 118 and the energy propagation paths 108. In an embodiment, the energy-inhibiting element 124 may be located on the first side 116 or the second side 114 orthogonal to the array of energy waveguides 112 or the plurality of energy locations 118.

In an embodiment, energy directed along the first energy propagation path 120 may converge with energy directed along a second energy propagation path 126 through a second energy waveguide 128. The first and second energy propagation paths may converge at a location 130 on the second side 114 of the array 112. In an embodiment, a third and fourth energy propagation paths 140, 141 may also converge at a location 132 on the first side 116 of the array 112. In an embodiment, a fifth and sixth energy propagation paths 142, 143 may also converge at a location 136 between the first and second sides 116, 114 of the array 112.

In an embodiment, the energy waveguide system 100 may comprise structures for directing energy such as: a structure configured to alter an angular direction of energy passing therethrough, for example a refractive, diffractive, reflective, gradient index, holographic, or other optical element; a structure comprising at least one numerical aperture; a structure configured to redirect energy off at least one internal surface; an optical relay; etc. It is to be appreciated that the waveguides 112 may include any one or combination of bidirectional energy directing structure or material, such as:

a) refraction, diffraction, or reflection;
b) single or compound multilayered elements;
c) holographic optical elements and digitally encoded optics;
d) 3D printed elements or lithographic masters or replicas;
e) Fresnel lenses, gratings, zone plates, binary optical elements;
f) retro reflective elements;

g) fiber optics, total internal reflection or Anderson Localization;
h) gradient index optics or various refractive index matching materials;
i) glass, polymer, gas, solids, liquids;
j) acoustic waveguides;
k) micro & nano scale elements; or
l) polarization, prisms or beam splitters.

In an embodiment, the energy waveguide systems propagate energy bidirectionally. In an embodiment, the energy waveguides are configured for propagation of mechanical energy. In an embodiment, the energy waveguides are configured for propagation of electromagnetic energy. In an embodiment, by interlacing, layering, reflecting, combining, or otherwise provisioning the appropriate material properties within one or more structures within an energy waveguide element, and within one or more layers comprising an energy waveguide system, the energy waveguides are configured for simultaneous propagation of mechanical, electromagnetic and/or other forms of energy.

In an embodiment, the energy waveguides propagate energy with differing ratios for u and v respectively within a 4D coordinate system. In an embodiment, the energy waveguides propagate energy with an anamorphic function. In an embodiment, the energy waveguides comprise multiple elements along the energy propagation path. In an embodiment, the energy waveguides are directly formed from optical fiber relay polished surfaces.

In an embodiment, the energy waveguide system comprises materials exhibiting Transverse Anderson Localization. In an embodiment, the energy waveguide system propagates hypersonic frequencies to converge tactile sensation in a volumetric space.

FIGS. 9A-H are illustrations of various embodiments of energy-inhibiting element 124. For the avoidance of doubt, these embodiments are provided for exemplary purposes and in no way limiting to the scope of the combinations or implementations provided within the scope of this disclosure.

FIG. 9A illustrates an embodiment of the plurality of energy locations 118 wherein an energy-inhibiting element 251 is placed adjacent to the surface of the energy locations 118 and comprises a specified refractive, diffractive, reflective, or other energy altering property. The energy-inhibiting element 251 may be configured to limit the first subset of energy propagation paths 290 to a smaller range of propagation paths 253 by inhibiting propagation of energy along energy propagation paths 252. In an embodiment, the energy-inhibiting element is an energy relay with a numerical aperture less than 1.

FIG. 9B illustrates an embodiment of the plurality of energy locations 118 wherein an energy-inhibiting structure 254 is placed orthogonal between regions of energy locations 118, and wherein the energy-inhibiting structure 254 exhibits an absorptive property, and wherein the inhibiting energy structure 254 has a defined height along an energy propagation path 256 such that certain energy propagation paths 255 are inhibited. In an embodiment, the energy-inhibiting structure 254 is hexagonal in shape. In an embodiment, the energy-inhibiting structure 254 is round in shape. In an embodiment, the energy-inhibiting structure 254 is non-uniform in shape or size along any orientation of the propagation path. In an embodiment, the energy-inhibiting structure 254 is embedded within another structure with additional properties.

FIG. 9C illustrates the plurality of energy locations 118, wherein a first energy-inhibiting structure 257 is configured to substantially orient energy 259 propagating therethrough into a first state. A second energy-inhibiting structure 258 is configured to allow energy 259, which is substantially oriented in the first state, to propagate therethrough, and to limit propagation of energy 260 oriented substantially dissimilarly to the first state. In an embodiment, the energy-inhibiting element 257, 258 is an energy polarizing element pair. In an embodiment, the energy-inhibiting element 257, 258 is an energy wave band pass element pair. In an embodiment, the energy-inhibiting element 257, 258 is a diffractive waveguide pair.

FIG. 9D illustrates an embodiment of the plurality of energy locations 118, wherein an energy-inhibiting element 261 is structured to alter energy propagation paths 263 to a certain extent depending upon which of the plurality of energy locations 118 the energy propagation paths 263 extends through. Energy-inhibiting element 261 may alter energy propagation paths 263 in a uniform or non-uniform way along energy propagation paths 263 such that certain energy propagation paths 262 are inhibited. An energy-inhibiting structure 254 is placed orthogonal between regions of energy locations 118, and wherein the energy-inhibiting structure 254 exhibits an absorptive property, and wherein the inhibiting energy structure 254 has a defined height along an energy propagation path 263 such that certain energy propagation paths 262 are inhibited. In an embodiment, an inhibiting element 261 is a field lens. In an embodiment, an inhibiting element 261 is a diffractive waveguide. In an embodiment, an inhibiting element 261 is a curved waveguide surface.

FIG. 9E illustrates an embodiment of the plurality of energy locations 118, wherein an energy-inhibiting element 264 provides an absorptive property to limit the propagation of energy 266 while allowing other propagation paths 267 to pass.

FIG. 9F illustrates an embodiment of the plurality of energy locations 118, and the plurality of energy waveguides 112, wherein a first energy-inhibiting structure 268 is configured to substantially orient energy 270 propagating therethrough into a first state. A second energy-inhibiting structure 271 is configured to allow energy 270, which is substantially oriented in the first state, to propagate therethrough, and to limit propagation of energy 269 oriented substantially dissimilarly to the first state. In order to further control energy propagation through a system, exemplified by the stray energy propagation 272, energy-inhibiting structures 268, 271 may require a compound energy-inhibiting element to ensure energy propagation maintains accurate propagation paths.

FIG. 9G illustrates an embodiment of the plurality of energy locations 118, and wherein an energy-inhibiting element 276 provides an absorptive property to limit the propagation of energy along energy propagation path 278 while allowing other energy along energy propagation path 277 to pass through a pair of energy waveguides 112 for an effective aperture 284 within the array of waveguides 112. In an embodiment, energy-inhibiting element 276 comprises black chrome. In an embodiment, energy-inhibiting element 276 comprises an absorptive material. In an embodiment, energy-inhibiting element 276 comprises a transparent pixel array. In an embodiment, energy-inhibiting element 276 comprises an anodized material.

FIG. 9H illustrates an embodiment comprising a plurality of energy locations 118, and a plurality of energy waveguides 112, wherein a first energy-inhibiting structure 251 is placed adjacent to the surface of the energy locations 118 and comprises a specified refractive, diffractive, reflective, or other energy altering property. The energy-inhibiting structure 251 may be configured to limit the first subset of energy propagation paths 290 to a smaller range of propagation paths 275 by inhibiting propagation of energy along energy propagation paths 274. A second energy-inhibiting structure 261 is structured to alter energy propagation paths 275 to a certain extent depending upon which of the plurality of energy locations 118 the energy propagation paths 275 extends through. Energy-inhibiting structure 261 may alter energy propagation paths 275 in a uniform or non-uniform way such that certain energy propagation paths 274 are inhibited. A third energy-inhibiting structure 254 is placed orthogonal between regions of energy locations 118. The energy-inhibiting structure 254 exhibits an absorptive property, and has a defined height along an energy propagation path 275 such that certain energy propagation paths 274 are inhibited. An energy-inhibiting element 276 provides an absorptive property to limit the propagation of energy 280 while allowing energy 281 to pass through. A compound system of similar or dissimilar waveguide elements 112 are positioned to substantially fill an effective waveguide element aperture 285 with energy from the plurality of energy locations 118 and to alter the propagation path 273 of energy as defined by a particular system.

In an embodiment, the energy-inhibiting element 124 may comprise a structure for attenuating or modifying energy propagation paths. In an embodiment, the energy-inhibiting element 124 may include one or more energy absorbing elements or walls positioned within the system to limit propagation of energy to or from the waveguides 112. In an embodiment, the energy-inhibiting element 124 may include a specified numerical aperture, positioned within the system 100 to limit the angular distribution of energy to and from waveguide 112.

In an embodiment, the energy-inhibiting element 124 may include one or more energy blocking walls, structures, metal, plastic, glass, epoxy, pigment, liquid, display technologies or other absorptive or structural material, with a determined thickness between a plane of energy locations 122 and a waveguide array plane with voids or structures that are up to the pitch of a waveguide aperture diameter.

In an embodiment, the energy-inhibiting structure 124 is located proximate the first energy location 122 and comprises an optical relay faceplate adjacent to the first energy location 122. In an embodiment, the energy-inhibiting element 124 may include an optical relay faceplate comprising one or more spatially consistent or variable numerical apertures, wherein the numerical aperture value meaningfully limits the angular distribution of energy to and from the waveguide 112. For example, an embodiment of the numerical aperture may be designed to provide an angular distribution that is at or near two times the field of view formed between the energy location and perpendicular to the center of the effective waveguide element size, entrance pupil, aperture, or other physical parameter for energy propagation, to provide off-axis fill factor for the specified waveguide aperture 134.

In an embodiment, the energy-inhibiting element 124 may include a binary, gradient index, Fresnel, holographic optical element, zone plate or other diffractive optical element that alters the path of energy waves through the system to decrease scatter, diffusion, stray light, or chromatic aberration. In an embodiment, the energy-inhibiting element 124 may include a positive or negative optical element at or around the location wherein the energy propagation path is altered to further increase the fill factor of the waveguide aperture 134 or decrease stray light. In an embodiment, the energy-inhibiting element 124 may include an active or passive polarized element combined with a second active or passive polarized element designed to provide spatial or time multiplexed attenuation of defined regions of the energy location 122, waveguide aperture 134, or other regions. In an embodiment, the energy-inhibiting element 124 may include an active or passive aperture stop barrier designed to provide spatial or time multiplexed attenuation of defined regions of the energy location 122, waveguide aperture 134, or other regions. In an embodiment, the energy-inhibiting element 124 many include any one the following or any combination thereof:

a) physical energy baffle structures;
    b) volumetric, tapered or faceted mechanical structures;
    c) aperture stops or masks;
    d) optical relays and controlled numerical apertures;
    e) refraction, diffraction, or reflection;
    f) retro reflective elements;
    g) single or compound multilayered elements;
    h) holographic optical elements and digitally encoded optics;
    i) 3D printed elements or lithographic masters or replicas;
    j) Fresnel lenses, gratings, zone plates, binary optical elements;
    k) fiber optics, total internal reflection or Anderson localization;
    l) gradient index optics or various refractive index matching materials;
    m) glass, polymer, gas, solids, liquids;
    n) milli, micro & nano scale elements; and
    o) polarization, prisms or beam splitters In an embodiment, the energy-inhibiting structure 124 may be constructed to include hexagonally packed energy blocking baffles constructed to form voids that are tapered along the Z axis, decreasing in void size as the aperture stop location for the waveguide system is reached. In another embodiment, the energy-inhibiting structure 124 may be constructed to include hexagonally packed energy blocking baffles bonded to an optical relay face plate. In another embodiment, the energy-inhibiting structure 124 may be constructed to include hexagonally packed energy blocking baffles filled with a prescribed refractive index to further alter the path of energy wave projection to and from the energy waveguide array. In another embodiment, a diffractive or refractive element may be placed, attached or bonded to the energy blocking baffle with a defined waveguide prescription to further alter the path of energy projection to and from the waveguide elements 112. In another example, the energy-inhibiting structure 124 may be formed into a single mechanical assembly, and the energy waveguide array 112 may be placed, attached or bonded to the assembled energy-inhibiting element 124. It is to be appreciated that other implementations may be leveraged to enable other energy waveguide configurations or super-resolution considerations.

In an embodiment, the energy-inhibiting structure 124 may be located proximate the first energy location 122 and generally extend towards the first energy waveguide 104. In an embodiment, the energy-inhibiting structure 124 may be located proximate the first energy waveguide 104 and generally extend towards the first energy location 122.

In an embodiment, the energy-inhibiting elements are configured for inhibiting electromagnetic energy. In some embodiments, the electromagnetic energy may be defined by a wavelength, the wavelength belonging to a regime selected from a group consisting of visible light, ultraviolet, infrared, or x-ray.

In an embodiment, the energy-inhibiting elements are configured for inhibiting mechanical energy. In some embodiments, the mechanical energy may be defined by pressure waves, the waves being one of: tactile pressure waves, acoustic sound vibrations or ultrasound waves.

In an embodiment, by interlacing, layering, reflecting, combining, or otherwise provisioning the appropriate material properties within one or more structures within an energy-inhibiting element, and within one or more layers comprising an energy waveguide system, the energy-inhibiting elements are configured for simultaneous attenuation of mechanical, electromagnetic and/or other forms of energy.

Figure 13:
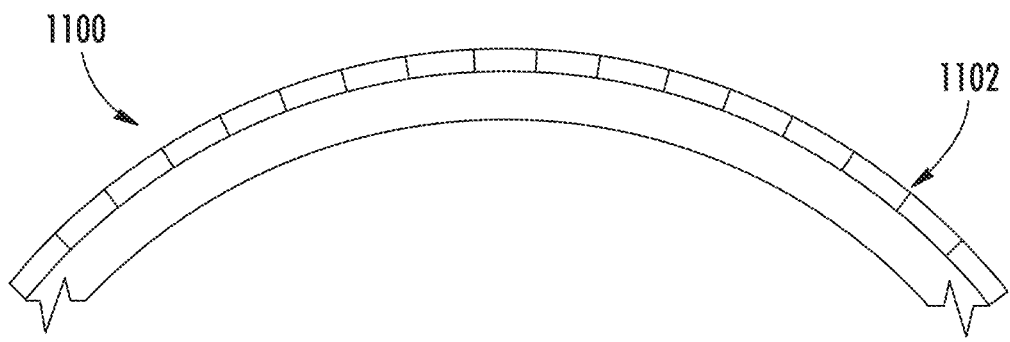
FIG. 13 illustrates an embodiment featuring an array of energy waveguides arranged in a curved configuration.

In an embodiment, an array of energy waveguides may be arranged to form a planar surface, or a curved surface of a desirable shape. FIG. 13 is an illustration of an embodiment 1100 featuring an array of energy waveguides 1102 arranged in a curved configuration.

Embodiments of the present disclosure may be configured to direct energy of any wavelength belonging to the electromagnetic spectrum, including visible light, ultraviolet, infrared, x-ray, etc. The present disclosure may also be configured to direct other forms of energy such as acoustic sound vibrations and tactile pressure waves.

Figure 10:
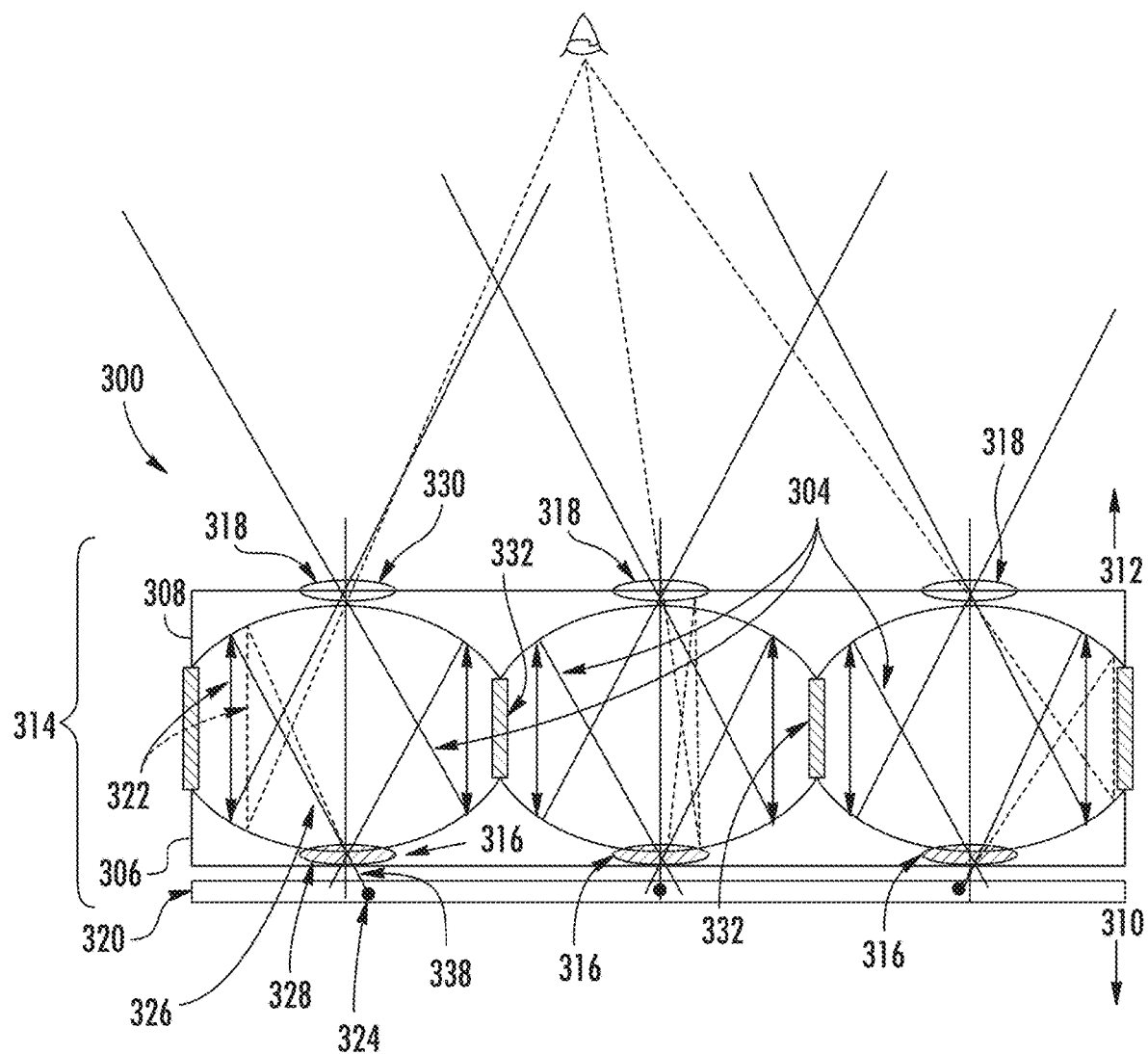
FIG. 10 illustrates an additional embodiment of an energy waveguide system.

FIG. 10 is an illustration of an additional embodiment of an energy waveguide system 300. The energy waveguide system 300 may define a plurality of energy propagation paths 304, and may comprise a reflector element 314 comprising a first reflector 306 located on a first side 310 of the reflector element 314, the first reflector 306 comprising one or more aperture stops 316 formed therethrough, and a second reflector 308 located on a second side 312 of the reflector element 314, the second reflector 308 comprising one or more aperture stops 318 formed therethrough. The first and second reflectors 306, 308 are configured to direct energy along a plurality of energy propagation paths 304 extending through the aperture stops of the first and second reflectors 316, 318 and a plurality of energy locations 320 on the first side 310 of the reflector element 314. A first subset 322 of the plurality of energy propagation paths 304 extend through a first energy location 324. The reflector element 314 is configured to direct energy along a first energy propagation path 326 of the first subset 322 of the plurality of energy propagation paths 304.

In an embodiment, the first energy propagation path 326 may be defined by a first chief ray 338 formed between the first energy location 324 and a first aperture stop 328 of the first reflector 306. The first energy propagation path 326 may extend from a first aperture stop 330 of the second reflector 308 towards the second side 312 of the reflector element 314 in a unique direction extending from the first aperture stop 330 of the second reflector 308, which is determined at least by the first energy location 324.

In an embodiment, energy directed along the first energy propagation path 326 substantially fills the first aperture stop 328 of the first reflector 306 and the first aperture stop 330 of the second reflector 308.

In an embodiment, an energy-inhibiting element 332 may be positioned to limit propagation of energy along a portion 350 of the first subset 322 of the plurality of energy propagation paths 304 that do not extend through the first aperture stop 328 of the first reflector 306.

In an embodiment in which the energy is light and the energy waveguide is operable to direct said light, with a perfect parabolic structure, any ray that passes through, or from, the focus of the first reflector will reflect parallel to the optical axis, reflect off of the second reflector, and then relay at the same angle in the inverse orientation.

In an embodiment, the first reflector and second reflector have differing focal lengths, in order to produce varied magnification of the energy information and/or to alter angular field of view coverage as a viewer from above the surface of the second reflector would view the reflected information. The aperture stops may be of differing sizes for varied design purposes in collaboration with the varied focal lengths.

An additional embodiment is provided where both reflective surfaces are conical, faceted, curved in a non-linear shape or otherwise. The design of this curvature is critical to ensuring that the display information and the viewed information may have a non-linear relationship to change or simplify signal processing.

In an embodiment, the energy waveguides comprise flexible reflective surfaces capable of altering the reflective surface profile dynamically to change the propagation path of energy through the energy waveguide system.

Figure 11:
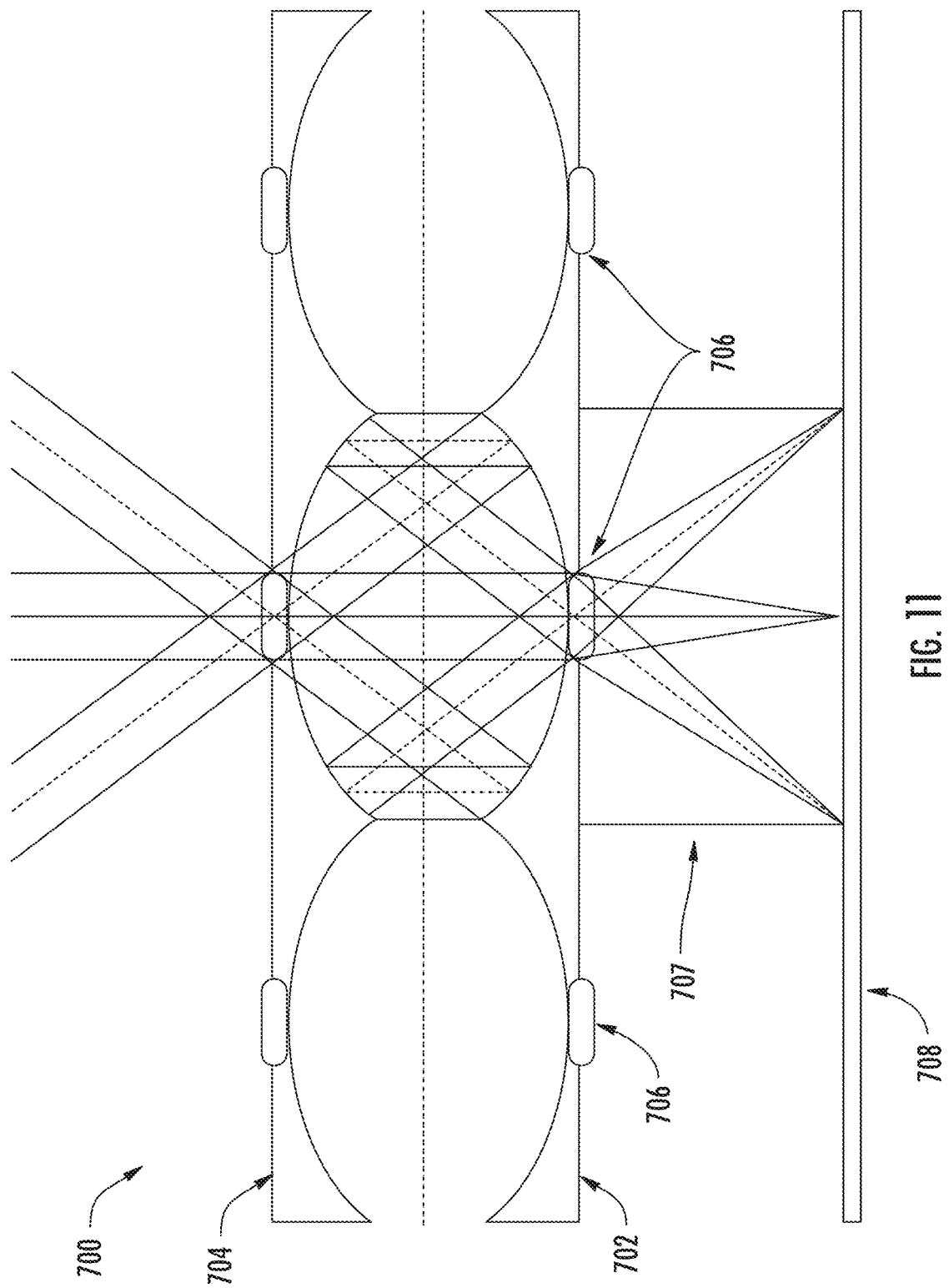
FIG. 11 illustrates an additional embodiment of an energy waveguide system.

In an embodiment, additional waveguides, including but not limited to reflective or optical elements, birefringent materials, liquid lenses, refractive, diffractive, holographic, or the like, may be located anywhere within the energy propagation path. With this approach, one such embodiment provides a design such that when viewed, the view angles are at significantly different position than the aperture stop and focal length would have provided otherwise. FIG. 11 demonstrates one such application of this approach.

FIG. 11 is an illustration of an embodiment of an energy waveguide system 700. Energy waveguide system 700 comprises first and second reflectors 702 and 704, respectively. Positioned at the focus of the second reflector 702 are additional optical elements 706 and an energy inhibitor 707 perpendicular to the energy location 708. The additional optical elements are designed to affect energy propagation paths of energy propagating through energy waveguide system 700. Additional waveguide elements may be included within the energy waveguide system 700, or additional energy waveguide systems may be placed into the energy propagation path.

Figure 12:
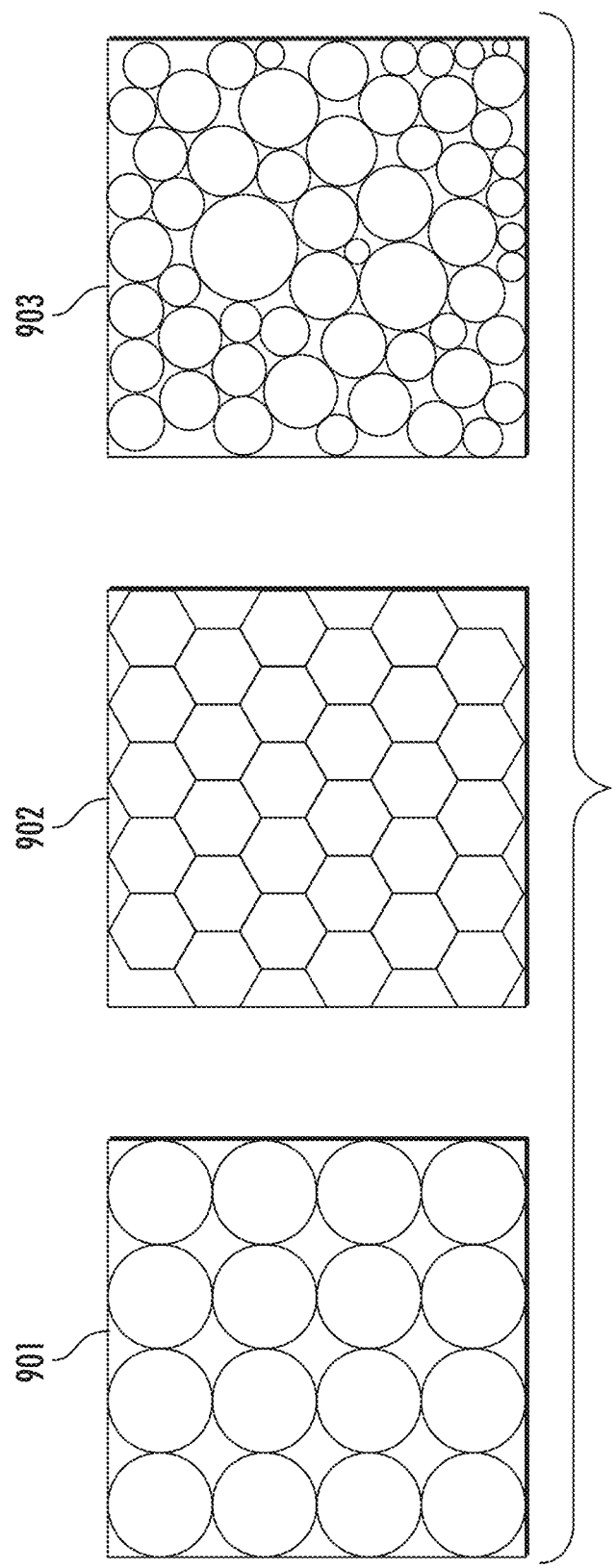
FIG. 12 highlights the differences between square packing, hex packing and irregular packing for energy waveguide design considerations.

In an embodiment, the array of energy waveguide elements may include:
a) A hexagonal packing of the array of energy waveguides;
b) A square packing of the array of energy waveguides;
c) An irregular or semi-regular packing of the array of energy waveguides;
d) Curved or Non-planar array of energy waveguides;
e) Spherical array of energy waveguides;
f) Cylindrical array of energy waveguides;
g) Tilted regular array of energy waveguides;
h) Tilted irregular array of energy waveguides;
i) Spatially varying array of energy waveguides;
j) Multi-layered array of energy waveguides;

FIG. 12 highlights the differences between square packing 901, hex packing 902 and irregular packing 903 of an array of energy waveguide elements.

Energy waveguides may be fabricated on a glass or plastic substrate to specifically include optical relay elements if desirable and may be designed with glass or plastic optical elements to specifically include optical relays as well as desired. Furthermore, the energy waveguide may be faceted for designs that provide multiple propagation paths or other column/row or checkerboard orientations, specifically considering but not limited to multiple propagation paths separated by beam-splitters or prisms, or tiled for waveguide configurations that allow for tiling, or a singular monolithic plate, or tiled in a curved arrangement (e.g. faceted cylinder or spherical with geometry alterations to the tiles to mate accordingly), curved surfaces to include but not limited to spherical and cylindrical or any other arbitrary geometry as required for a specific application.

In an embodiment where the array of energy waveguides comprises a curved configuration, the curved waveguide may be produced via heat treatments or by direct fabrication onto curved surfaces to include optical relay elements.

In an embodiment, the array of energy waveguides may abut other waveguides and may cover entire walls and/or ceilings and or rooms depending on specific application. The waveguides may be designed explicitly for substrate up or substrate down mounting. The waveguide may be designed to mate directly to an energy surface or be offset with an air gap or other offset medium. The waveguide may include an alignment apparatus to provide the ability to focus the plane actively or passively either as a permanent fixture or a tooling element. The purposes of the geometries described are to help optimize the angle of view defined by the normal of the waveguide element and the represented imagery. For a very large energy surface planar surface, the majority of the angular samples at the left and right-most of the surface are mainly outside of the viewing volume for an environment. For that same energy surface, with a curved contour and a curved waveguide, the ability to use more of these propagating rays to form the converging volume is increased significantly. This is however at the expense of usable information when off-axis. The application specific nature of the design generally dictates which of the proposed designs will be implemented. Furthermore, a waveguide may be designed with regular, graduated, or regional element structures that are fabricated with an additional waveguide element to tilt the element towards a predetermined waveguide axis.

In embodiments where the energy waveguides are lenses, the embodiments may include both convex and concave lenslets, and may include the fabrication of the lenses directly onto an optical relay surface. This may involve destructive or additive lenslet fabrication processes to include removal of material to form or stamp and lenslet profile, or the direct replica fabricated directly to this surface.

An embodiment may include a multiple layered waveguide design that provides additional energy propagation optimizations and angular control. All of the above embodiments may be combined together independently or in conjunction with this approach. In an embodiment, a multiple layered design may be envisioned with tilted waveguide structures on a first waveguide element and a regionally varying structure for a second waveguide element.

An embodiment includes the design and fabrication of per element or per region liquid lens waveguide joined together as a single waveguide. An additional design of this approach includes a single birefringent or liquid lens waveguide electrical cell that can modify an entire waveguide array simultaneously. This design provides the ability to dynamically control the effective waveguide parameters of the system without redesigning the waveguide.

In an embodiment configured to direct light, with any combination of the disclosures provided herein, it is possible to generate a wall mounted 2D, light field or holographic display. The wall mounted configuration is designed such that a viewer is looking at an image that may float in front, at or behind the designed display surface. With this approach, the angular distribution of rays may be uniform, or provided with increased density at any particular placement in space depending on specific display requirements.

In this fashion, it is possible to configure the waveguides to alter angular distribution as a function of surface profile. For example, for a given distance perpendicular to the display surface and a planar waveguide array, an optically perfect waveguide would provide increased density at the perpendicular center of the display with a gradual increase in ray separation distance along a given perpendicular distance to the display. Conversely, if viewing the rays radially about the display where a viewer maintains a distance between the eyes and the center point of the display, the viewed rays would maintain consistent density across the entire field of view. Depending on the anticipated viewing conditions, the properties of each element may be optimized by altering the waveguide functions to produce any potential distribution of rays to optimize the viewing experience for any such environment.

Figure 14:
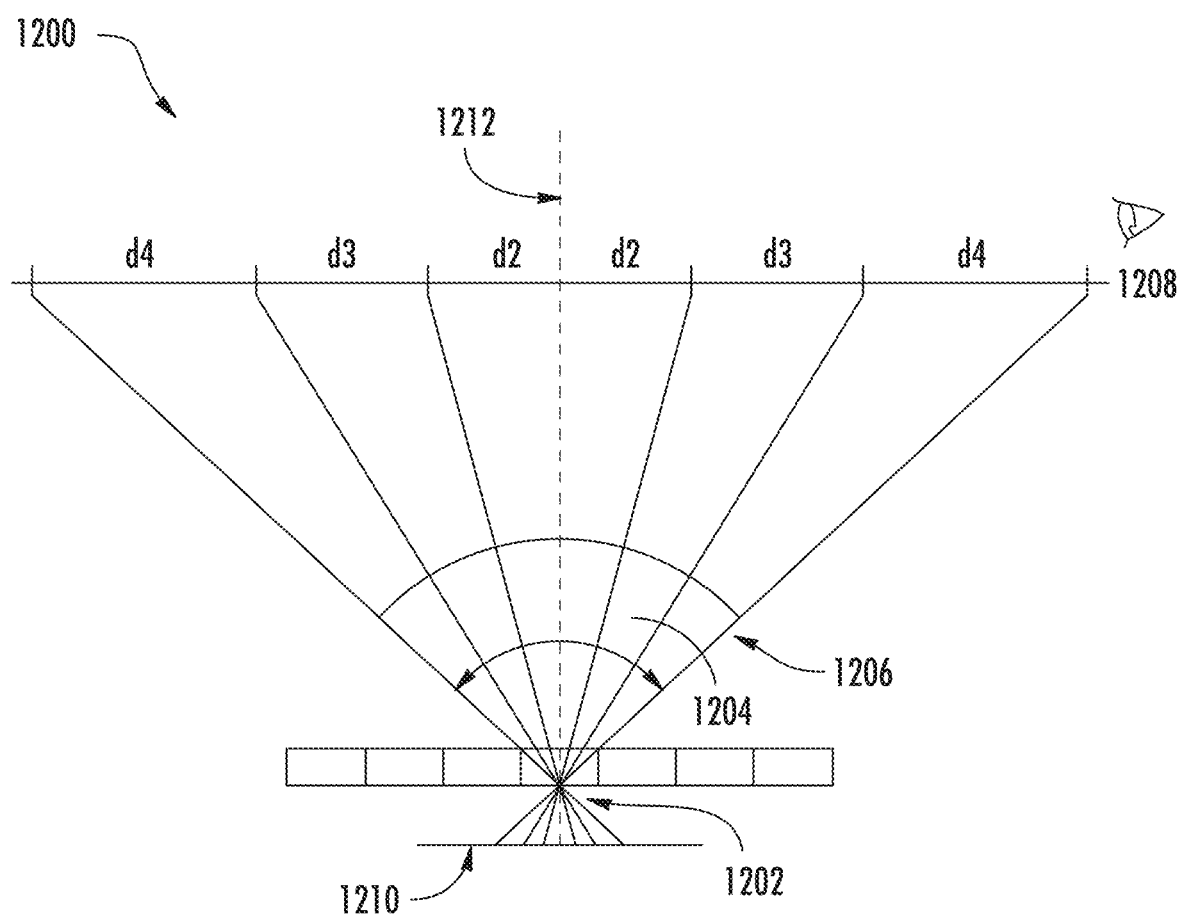
FIG. 14 illustrates an embodiment that highlights how a waveguide element may affect a spatial distribution of energy passing therethrough.

FIG. 14 is an illustration of an embodiment 1200 which highlights how a single waveguide element function 1202 may produce identical distribution of energy 1204 across a radial viewing environment 1206, whereas the same waveguide element function 1202 when propagated at a distance 1208 that is constant and parallel to the waveguide surface 1210 will appear to exhibit increased density at the waveguide element center 1212 of the waveguide surface and decreased density further from the center 1212 of the waveguide surface.

FIG. 15 is an illustration of an embodiment 1300 which illustrates configuring the waveguide element functions 1302 to exhibit uniform density at a constant distance 1304 parallel to the waveguide surface 1306 that simultaneously produces apparent lower density at the center 1310 of the waveguide surface 1306 when measured about a radius 1308 about the center of the waveguide surface 1306.

The ability to generate a waveguide function that varies sampling frequency over field distance is a characteristic of various waveguide distortions and known in the art. Traditionally, the inclusion of distortions are undesirable in a waveguide function, however, for the purposes of waveguide element design, these are all characteristics that are claimed as benefits to the ability to further control and distribute the propagation of energy depending on the specific viewing volume required. It may require the addition of multiple functions or layers or a gradient of functions across the entirety of the waveguide array depending on the viewing volume requirements.

In an embodiment, the functions are further optimized by curved surfaces of the energy surface and/or the waveguide array. The variation of the normal of the chief ray angle in relation to the energy surface itself may further increase efficiency and require a different function than a planar surface, although the gradient, variation and/or optimization of the waveguide function still applies.

Further, leveraging the resultant optimized waveguide array in consideration of waveguide stitching methodologies, it is possible to further increase the effective size of the waveguide by tiling each of the waveguides and systems to produce any size or form-factor desired. It is important to note that the waveguide array may exhibit a seam artifact unlike the energy surface by virtue of reflections produced between any two separate substrates, the apparent contrast differential at the mechanical seam, or due to any form of non-square grid packing schema. To counteract this effect, either a larger singular waveguide may be produced, refractive matching materials may be leveraged between the edges of any two surfaces, or regular waveguide grid structures may be employed to ensure that no elements are split between two waveguide surfaces, and/or precision cutting between energy-inhibiting elements and seaming along a non-square waveguide grid structure may be leveraged.

With this approach, it is possible to produce room scale 2D, light field and/or holographic displays. These displays may be seamless across large planar or curved walls, may be produced to cover all walls in a cubic fashion, or may be produced in a curved configuration where either a cylindrical-type shape or a spherical-type shape is formed to increase view angle efficiency of the overall system.

Alternatively, it is possible to design a waveguide function that warps the propagated energy to virtually eliminate the region that is not desired in the required angle of view resulting in a non-uniform distribution of energy propagation. To accomplish this, one may implement a Taurus shaped optical profile, annular lens, concentric prism array, a Fresnel or diffractive function, binary, refractive, holographic, and/or any other waveguide design may allow for a larger aperture and shorter focal length (herein will be referred to as a "Fresnel lenslet") to provide the ability to practically form a single or multi element (or multiple sheets) Fresnel waveguide array. This may or may not be combined with additional optics, including an additional waveguide array, depending on waveguide configuration.

In order to produce wide energy propagation angles (e.g. 180 degrees) a very low effective f/number (e.g. <f/0.5) is required and in order to ensure that no 4D "Disk Flipping" occurs (the ability for the ray from one waveguide element to see undesired energy locations underneath of any second waveguide element), it is further required that the focal length be appropriately matched closely to the angle of view required. This means that in order to produce a ~160 degree viewing volume, a ~f/0.17 lens and a nearly matched ~0.17 mm focal length is required.

FIG. 16 illustrates an embodiment 1400 wherein the plurality of energy waveguides comprise diffractive waveguide elements 1402, and demonstrates one proposed structure for a modified Fresnel waveguide element structure 1404 that produces an effectively extremely short focal length and low f/number while simultaneously directing rays of energy to explicitly defined locations 1406.

FIG. 17 illustrates an embodiment 1500 wherein the plurality of energy waveguides comprise elements 1502, and demonstrates how such a waveguide configuration 1506 may be used in an array to provide full density of ray propagation for the desired viewing volume 1504.

A further embodiment of the proposed modified waveguide configuration provides for a method to produce radially symmetric or spiraling rings or gradient of two or more materials along either or both of a transverse or longitudinal orientation with a refractive index separated by a predetermined amount with a per ring pitch with a diameter of X, where X may be constant or variable.

In a further embodiment, equal or non-linear distribution of all of the rays are produced with or without the modified waveguide configurations for wall-mounted and/or table-mounted waveguide structures as well as all room or environment based waveguide structures where multiple waveguides are tiled.

With a waveguide array, it is possible to produce planes of projected light that converge in space at a location that is not located at the surface of the display itself. By ray-tracing these rays, one can clearly see the geometry involved and how converging rays may appear both in-screen (away from the viewer) as well as off-screen (towards viewer) or both simultaneously. As planes move away from the viewer on planar displays with traditional waveguide array designs, the planes tend to grow with the frustum of the viewpoint and may become occluded by the physical frame of the display itself depending on the number of contributing illumination sources. By contrast, as planes move toward the viewer on planar displays with traditional waveguide array designs, the planes tend to shrink with the frustum of the viewpoint but are viewable from all angles at the specified location as long as the viewer is at an angle presenting energy to the eye and the virtual plane does not move beyond the angle created between the viewer and the far edge of the active display area.

In one embodiment, the viewed 2D image or images are presented off of the screen. In another embodiment, the viewed 2D image or images are presented in screen. In another embodiment, the viewed 2D image or images are presented simultaneously both in and/or off screen. In another embodiment, the viewed 2D image or images are presented in combination with other volumetric elements or presented as text for other graphic design or interactive reasons. In yet another embodiment, the viewed 2D image or images are presented with higher effective 2D resolution than the physical number of X and Y waveguide elements would otherwise suggest due to the ability for rays to converge with higher density in space than physical elements.

The novelty of this approach is that it is entirely possible to manufacture a holographic display that produces both volumetric imaging capabilities, as well as extremely high resolution 2D imagery such that there is no further mechanical or electronic apparatus or alterations necessary to the waveguides in the display to move seamlessly between flat and volumetric imagery or produce other interesting effects.

With this property, it is possible to programmatically isolate certain illumination sources to present to a viewer that is only visible at explicit angles to the display.

In one embodiment, a single pixel or group of pixels are illuminated under each waveguide element at an angle that triangulates to the viewer's eye and presents an image that is only viewable from that viewer's position in space.

In another embodiment, a second illumination source or group of illumination sources are presented simultaneously to triangulate to a position that is only viewable by a second viewer and contains an image that may be the same or different than the first image presented to the first viewer. For the avoidance of doubt, this may be X addressable viewpoints where X represents the number of individually addressable viewpoints which may be one or more.

In another embodiment, these images are presented with eye, retinal, object or the like tracking leveraging sensors and algorithms known in the art, to dynamically vary the illuminated pixel location to present imagery dynamically to a triangulated location between the viewer and the pixels under each waveguide element. This may be applied to one or more viewers. The tracking may be performed as a 2D process or as a 3D/stereoscopic process, or leveraging other depth sensing technologies known in the art.

In one embodiment, the first region and second region are both parabolic in profile, with the first region focus located at the apex of the second region and the second region focus located at the apex of the first region and the display surface located at an opening located at the apex of the second region and an opening equivalent to the diameter of the display surface presented to the apex of the second region located at the apex of the first region. With this approach, the display surface image will appear to float above a surface without any physical surfaces as the viewed rays that pass through the focus of the second region from an off-axis viewpoint will reflect off of the second region surface and parallel off of the first surface and then at the same angle from the viewed position in the inverse orientation from the first region to the display surface.

In an embodiment, a dual parabolic relay system that includes two reflective regions each with a focus located at the apex of the alternate reflector, the display surface located at the apex of the second region, and an opening equivalent to the diameter of the presented display surface located at the first region producing a virtual image of the display surface. In the event that a waveguide array, holographic or light field display are leveraged, the viewed imagery will retain the nature of the holographic data as well as appearing to float in space without a physical display surface.

In another embodiment, the focus location of region two is differing to produce magnification or minification. In a second embodiment, the regions have matched focal lengths and are offset by a distance greater than the focal length in order to produce a virtual image with increased magnification.

In another embodiment, the parabolic profiles are manufactured to accommodate a specific shape that results in differing viewed positions from the display to accommodate various display surface geometries or other required viewing angle or condition.

In another embodiment, the regions contain multiple facets in order to independently propagate rays of light by facet region rather than as a singular surface.

In another embodiment, the reflective surface are formed of energy relays such that the CRA of the energy surface exceeds the view angle possible from the curve applied to one or more surface(s) wherein the first surface that would have otherwise been a reflective surface has a certain geometric profile and the second surface at the alternate end of the waveguide element has a certain geometric profile, and cumulatively they have a CRA that reflects energy from a viewer's position and the addition of energy surface panels at the second surface may be implemented thereby providing energy information that is not viewable from the viewer's direct position but may provide energy information indirectly through one or more reflective surfaces and the associated calibration process required to compute the reflected imaging data in relation to the ultimately viewed data.

Four Dimensional Energy-Field Package Assembly

Large display surfaces for 4D energy projection systems present a number of challenges, including but not limited to, resolution and seaming. Embodiments of relay elements of this disclosure may allow embodiments that reduce, or eliminate, the perception of seams in a 4D energy projection in accordance with the principles of the present disclosure. The four-dimensional (4D) energy-field package assembly of this disclosure may also allow some embodiments to reduce or eliminate seaming in 4D energy systems and may be used instead of, or in cooperation with, the relay elements of this disclosure. An additional possible benefit allowed by some embodiments of the 4D energy-field package of the present disclosure is that display walls may be constructed and maintained more easily with a modular construction.

Traditional 2D video walls illustrate how seams can negatively impact the experience for viewers. Individual display units are assembled into a larger wall-sized displays. Spaces between the display units in the wall-sized display cause lines or seams to appear in the display which are readily visible at regular viewing distances.

Figure 18A:
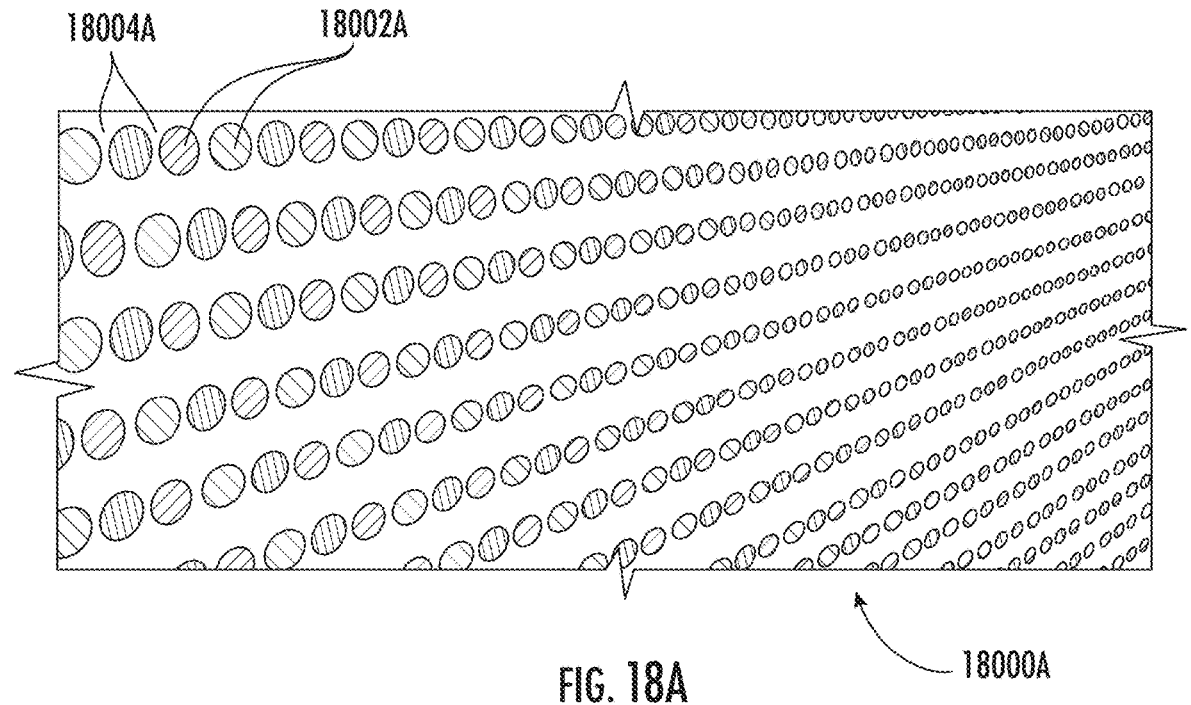
FIG. 18A illustrates a close up of an LED wall.

FIG. 18A depicts one technology that partially mitigates the visibility of seam gaps in LED video walls. In such devices, the LEDs 18002A that produce the source light for the display are reduced and encapsulated within a black enclosure 18004A. The black regions 18004A surrounding the LEDs 18002A may be larger than the seams created by spaces between adjacent display units (not depicted in FIG. 18A). The seams can essentially be hidden in the black regions 18004A between LEDs 18002A thereby creating the appearance of a seamless display surface.

Figure 18B:
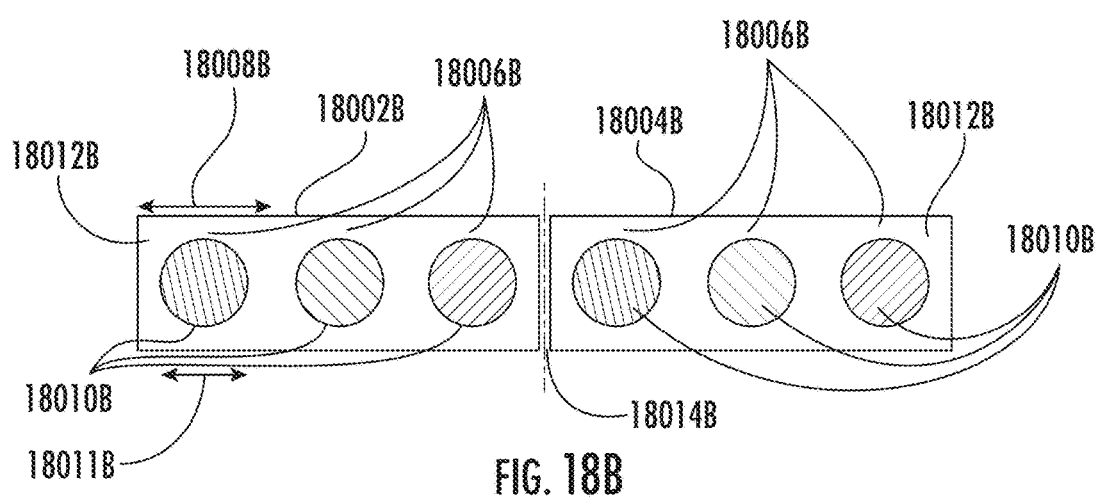
FIG. 18B illustrates how an LED wall can appear seamless.

FIG. 18B further illustrates this technology. FIG. 18B depicts a first LED panel 18002B and a second LED panel 18004B. Each panel comprises three LED packages 18006B that have equal LED package widths 18008B. The LED packages 18006B include diodes 18010B and a black region 18012B. The width of the actual LED diodes 18010B of the LED packages 18006B is shown by 18011B. And, the gap between the LED panels 18002B, 18004B is shown by 180014B. By introducing enough average space between individual lighting elements 18010B, a seam can be introduced without causing a noticeable gap between adjacent LED panels 18002B, 18004B while providing adequate resolution when viewed from a sufficiently far distance.

The effect of the approach shown in FIG. 18B is adequate when viewed from far enough away, but the manufacturing of these video walls is quite labor intensive. The highest density LEDs commercially available today are approximately 0.9 mm, which are multiple orders of magnitude larger than achievable pixels on silicon media.

Figure 19:
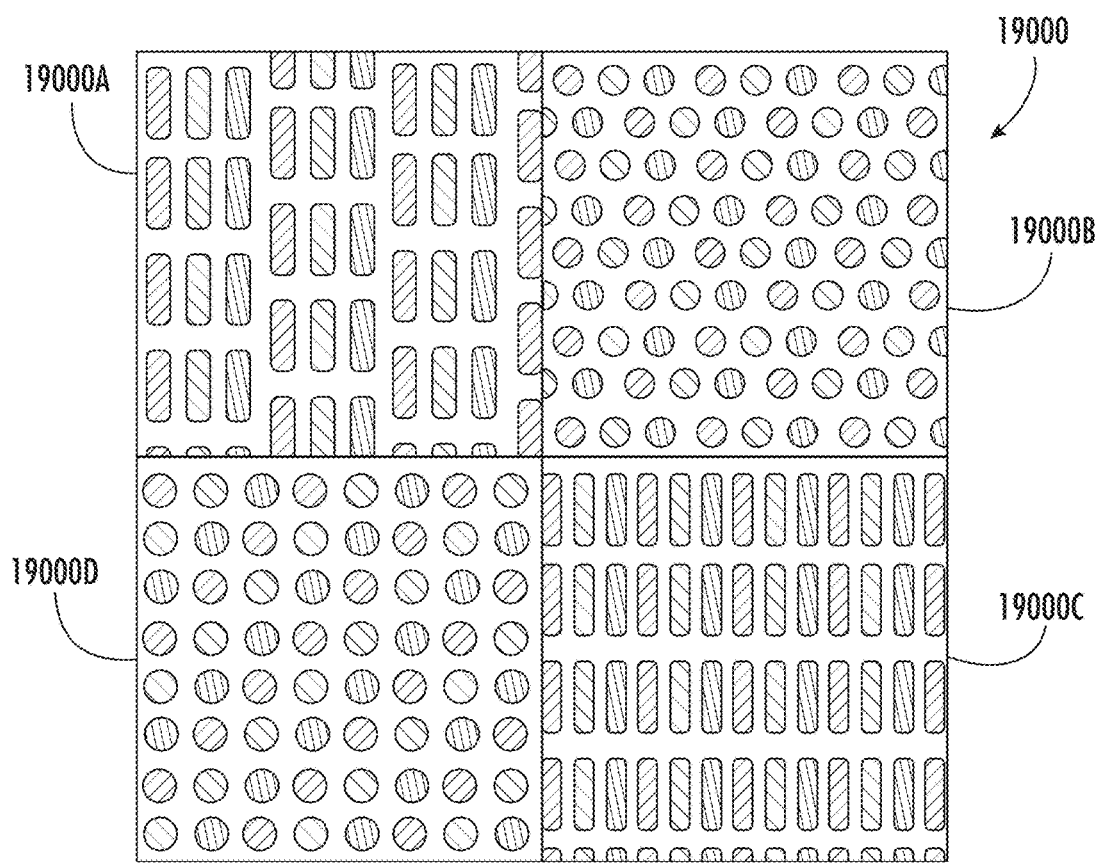
FIG. 19 illustrates various pixel patterns.

FIG. 19 illustrates various pixel patterns created using a silicon media process. The patterns shown cannot be seamless due to their high density. But, embodiments of the device of this disclosure may allow for leveraging lower resolution micro displays (or other energy devices) that are evenly spread about a larger surface. Each individual display in such embodiments, along with one or more waveguides, can be implemented as an independent collection of 4D functions. With this construct, it is possible to accommodate the dark region that surrounds each of the individual energy devices, and allow for the fabrication of dense arrays of lower resolution 4D functions (the "diode" equivalent). This allows seams between adjacent panels to appear no more visible than a traditional video wall, while providing the resolution required, without custom energy relay systems.

Figure 20:
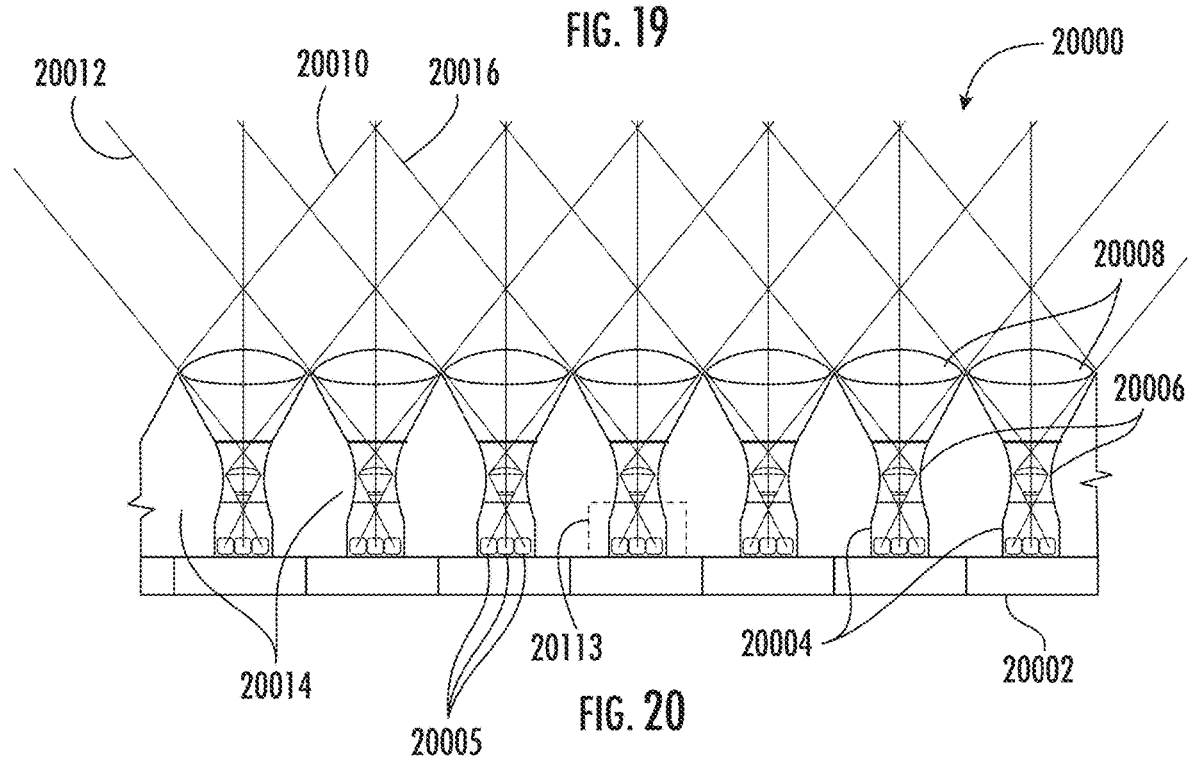
FIG. 20 illustrates embodiment of a 4D energy-field package assembly of this disclosure.

FIG. 20 illustrates an embodiment of a 4D energy-field package assembly 20000 for directing energy provided from a plurality of energy locations according to a 4D function. In FIG. 20, electronics 20002 may operate a series of modular 4D energy-field packages 20014, each containing an energy-source system 20113, one or more waveguides 20006, and optionally an aperture magnifying waveguide 20008. In an embodiment, each energy-source system 20113 is configured to provide energy to one or more energy locations 20005. Energy from each energy location 20005 can be received at waveguides 20006, and projected at an angle that corresponds, at least partially, to the position of the energy location 20005. There are two angular coordinates associated with each energy propagation path 20010, and each waveguide 20006 of each energy-field package may identified by a 2D spatial coordinate, and together these form a 4D coordinate set. The net result is that each energy-field package 20014 contains a 4D energy field coordinate for each waveguide in the package. Many energy-field packages 20014 can be used to form a 4D energy field display according to the present disclosure.

In one embodiment, the 4D energy-field package assembly 20000 includes a magnifying waveguide disposed on one side (e.g., first side) of the energy waveguide of each modular 4D energy-field package. In another embodiment, the 4D energy-field package assembly 20000 includes a magnifying waveguide disposed on the opposite side (e.g., second side) of the energy waveguide of each modular 4D energy-field package.

In some embodiments, the energy-source system 20113 may include a plurality of energy sources 20004, which may be any source known in the art configured to output energy. In some embodiments, the energy locations 20005 are located at the same location as the energy sources 20004 as shown in FIG. 20. In other embodiments, one or more energy locations 20005 may be located at the surface of the energy sources 20004. In some embodiments, the energy-source system 20113 may further include a relay system like that depicted in FIG. 3 that guides energy from an energy source 310 through the relay to the plurality of energy locations on a surface 350 of the relay. As will be appreciated, the energy-source system 20113 may include other types of relays or relay arrangements as discussed elsewhere in this disclosure and known in the art. Unless specifically noted otherwise, all the embodiments of the energy-source system 20113 may be combined with all the embodiment of the 3D printing system of this disclosure. As will be appreciated different embodiments may utilize different types of energy including but not limited electromagnetic, mechanical, or acoustical energy, among others.

Figure 21:
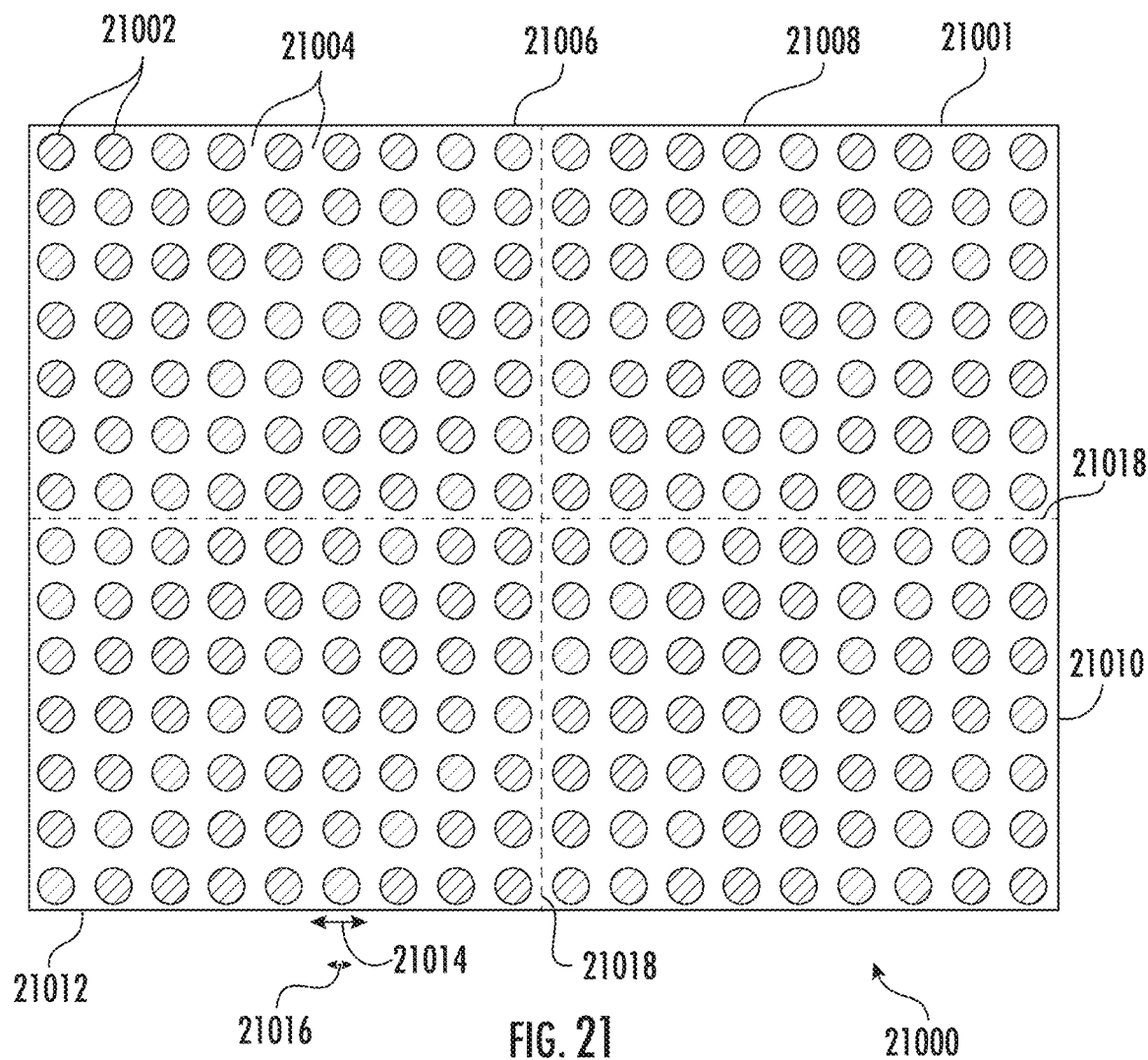
FIG. 21 illustrates embodiment of a 4D energy-field package assembly composed of four smaller adjacent panels.

FIG. 21 illustrates an embodiment of a 4D energy-field package assembly 21000 having four adjacent panels 21006, 21008, 21010, and 21012. The panels 21006, 21008, 21010, and 21012 may include a plurality of modular 4D energy-field packages 21002 with at least one border 21004. In an embodiment, borders 21004 may have black regions 21004 configured to increase separation between mechanical envelopes and reduce seams between adjacent panels 21006, 21008, 21010, and 21012. In FIG. 21, a package width is shown at 21014, while a smaller 4D function width 21016 (essentially the "diode" or energy waveguide but with holographic resolution) is shown. The dotted lines 21018 illustrate the effective exaggerated seam gaps 21018 between panels 21006, 21008, 21010 and 21012.

In some embodiments, the 4D energy-field package assembly 21000 of this disclosure may include a plurality of modular 4D energy-field packages 21002 formed in different shapes and sizes. The plurality of modular 4D energy-field packages 21002 may be configured to allow different arrangements of the 4D energy-field package assembly 21000 for different environments or applications some of which are discussed elsewhere in this application.

In some embodiments, the border 21004 is configured to evenly separate the at least one energy waveguide of the plurality of modular 4D energy-field packages 21002 when attached to a common mount 21001. In other embodiments, the distance between the at least one energy waveguide of the plurality of modular 4D energy-field packages 21002 may prevent seams in the 4D energy field. In yet some other embodiments, the plurality of 4D energy-field packages 21002 may be attached to the mount 21001 to form a grid of modular 4D energy-field packages 21000.

Figure 22:
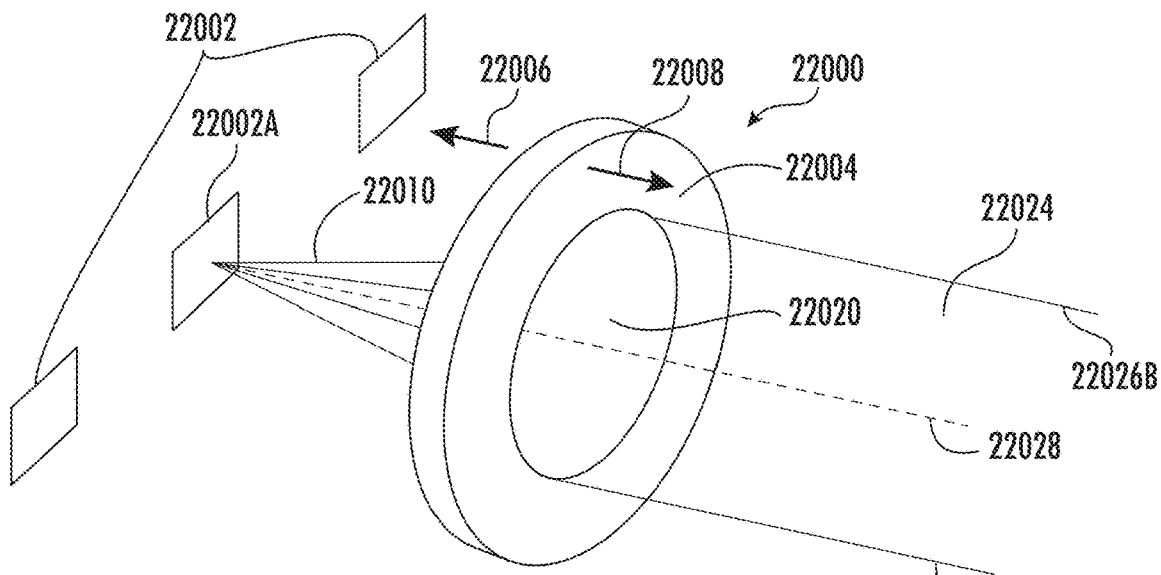
FIG. 22 depicts an embodiment of an energy-emitting component of a modular 4D energy-field package of this disclosure.

FIG. 22 depicts an embodiment of energy-emitting component 22000 of the modular 4D energy-field package. In an embodiment, each modular 4D energy-field package includes a plurality of energy sources that provide energy to energy locations 22002 necessary to generate produce an energy field. The energy sources can include different types of sources in different embodiments. In one embodiment, the energy sources may be LEDs. In other embodiments, the energy sources may be OLEDs, AMOLEDs, TOLEDS, or other sources known in the art. In some embodiments, more than one type of energy source may be used in each modular 4D energy-field package. In an embodiment, the plurality of modular 4D energy-field packages may include modular 4D energy-field packages where each, or some of the packages, may utilize different types of energy sources. For example, energy sources 22002 generating electromagnetic energy may be employed. In other instances, energy sources generating mechanical or acoustical energy may utilized. In yet some other embodiments, there may be a mixture of energy sources 22002 capable of producing electromagnetic, mechanical or acoustical energies, among others. Unless specifically noted otherwise the different embodiments of the energy sources of this disclosure may be combined with all the different embodiments of the 4D energy-field package assembly of this disclosure.

In an embodiment, the modular 4D energy-field packages may include an energy waveguide 22004 to direct energy from a plurality of energy locations 22002 from a first side 22006 of the energy waveguide 22004 to a second side 22008 of the energy waveguide 22004 along a plurality of energy propagation paths extending through a plurality of energy locations 22002 on the first side 22006 of the energy waveguide 22004, and through the waveguide aperture 22020. For example, the energy location 22002A produces energy rays 22010 which are directed to the propagation path 22028 on the other side 22008 of the waveguide 22004. The propagation path 22028 may contain energy across the entire aperture 22020, and has boundaries in one dimension denoted by rays 22026A and 22026B. In one embodiment, the propagation path 22028 may substantially fill the aperture 22020. It will be appreciated that although FIG. 22 only depicts one energy propagation path 20028, the embodiments of this disclosure allow many additional propagation paths to extend through the waveguide 22004 from additional energy locations. In other words, there may be a plurality of energy propagation paths 22028 extending from a plurality of energy locations 22002. In an embodiment, one propagation path 22028 may extend from each source location 22002. In some embodiments, each modular 4D energy-field package may include thousands of energy location 22002 and thousands of corresponding propagation paths 22028 with directions which may be determined at least in part by the locations of the energy locations 22002 relative to the position of the energy waveguides 22004.

In some embodiments, each modular 4D energy-field package may utilize different types of waveguides 22004. Different types of waveguides 22004 may be needed for systems that project different types of energy. For example, embodiments that project electromagnetic energy fields may utilize waveguides 22004 configured to direct electromagnetic energy, such as lenses. Similarly, embodiments that project mechanical energy may utilize waveguides 22004 configured to direct mechanical energy. And embodiments that project both electromagnetic energy and mechanical energy may include waveguides 22004 configured to direct either mechanical energy, electromagnetic energy, or both. Any of the waveguide structures describe elsewhere in this disclosure can be utilized in the embodiments of the 4D energy-field package assembly including but not limited to the waveguide structures discussed in reference to FIGS. 9-11 and 13-16, including waveguides 22004 having lenses and reflector elements, among others. In some embodiments, different waveguides 22004 may be combined with all the different embodiments of the 4D energy-field package assembly.

In an embodiment of the 4D energy-field package assembly, the plurality of energy propagation paths such as 22028 may extend through a plurality of energy locations such as 20002A, extending from the second side 22008 of the energy waveguide 22004 in a unique direction which is determined at least by the energy location 22002A relative to the waveguide 22004.

In another embodiment, the energy waveguide 22004 of the modular 4D energy-field includes an aperture 22020 where each energy propagation path such as 22028, with boundaries in one dimension illustrated by rays 22026A and 22026B, the rays 22026A and 22026B able to substantially fill the aperture 22020 of the energy waveguide 22004. This may also described with reference to aperture 134 of FIG. 7. Energy may propagate in the area 22024 between rays 22026A and 22026 along propagation path 22028 as discussed herein, and similarly with reference to aperture 134 of FIG. 7.

As discussed above and with reference to FIG. 7, energy directed along the first energy propagation path 120 may converge with energy directed along a second energy propagation path 126 through a second energy waveguide 128. The first and second energy propagation paths may converge at a location 130 on the second side 114 of the array 112. In an embodiment, a third and fourth energy propagation paths 140, 141 may also converge at a location 132 on the first side 116 of the array 112. In an embodiment, a fifth and sixth energy propagation paths 142, 143 may also converge at a location 136 between the first and second sides 116, 114 of the array 112.

Similarly, energy on propagation paths from waveguides of embodiments of 4D energy-field packages may converge. In some embodiments, energy directed along a first energy propagation path of the plurality 4D energy-field packages may converge with energy directed along a second energy propagation path of the plurality of 4D energy-field packages. In other embodiments, first and second energy propagation paths converge at a location on the second sides of the energy waveguides. And, in yet some other embodiments, the first and second energy propagation paths converge at a location on the first sides of the energy waveguides.

In one embodiment, at least one energy propagation path 20010 of the plurality of energy propagation paths 20012 of the plurality of modular 4D energy-field packages 20014 may converge with energy directed along at least one other energy propagation path 20016 of the plurality of energy propagation paths 20012 of the plurality modular 4D energy-field packages 20014. In one embodiment, the at least one first energy propagation path and the at least one other first energy propagation path may converge at a location on the first sides of the energy waveguides. In another embodiment, the at least one first energy propagation path and the at least one other first energy propagation path may converge at a location on the second sides of the energy waveguides. In yet another embodiment, the at least one first energy propagation path and the at least one other first energy propagation path may converge at a location between the first and second sides of the energy waveguides. In some other embodiments, the 4D coordinate set uniquely identifies the first energy propagation paths of the plurality of modular 4D energy-field packages. Furthermore, the 4D coordinate sets may also uniquely identify second, third, fourth, or any number of propagation paths extending from the second side of energy waveguides.

In some embodiments, like the one depicted in FIG. 22, the energy waveguide 22004 may be round and the aperture 22020 may be round. In other embodiments, the energy waveguide 22004 may have other shapes and sizes. In one example, the energy waveguide 22004 may be rectangular while the corresponding aperture 22020 may be of another shape. In other words, the energy waveguide 22004 and the corresponding aperture 20020 need not have the same or similar shapes and/or sizes. In some embodiments, the energy waveguide for electromagnetic energy may be a square-cut lens, and the aperture may be square in shape as well, or rounded in shape.

In an embodiment, a modular 4D energy-field package may include multiple energy-field waveguides. As discussed above, the location of each waveguide may include a 2D spatial coordinate of a 4D energy-field coordinate set. Embodiments of the modular 4D energy-field package that include multiple energy waveguides may be combined with any embodiments of the 4D energy-field package assembly of this disclosure. In some embodiments, the modular 4D energy-field package may include 2, 4, 8, 16 or any other number of energy waveguides.

In an embodiment, the energy propagation path 22028 may be defined by a chief ray 22028 formed between an energy location 22002A and a position on the energy waveguide 22004, which may be the middle of the waveguide 22004 having radial symmetry. As depicted in FIG. 22, the chief ray 22028 may occupy the propagation path 22028 so they are referred to with the same numeral. Chief rays 22028 may determine the direction of propagation of energy from a waveguide for a given energy source location, and are discussed elsewhere in this disclosure, at least with reference to FIG. 7. In one embodiment, energy directed along chief ray energy propagation path 22028 may include one or more energy rays 22026A, 22026B directed through the energy waveguide 22004 in a direction that is substantially parallel to the first chief ray 22028 as discussed in this disclosure, including without limitation at least in reference to FIG. 7. It will be appreciated that FIGS. 21-22 do not limit the embodiments of this disclosure and are provided for illustrative purposes.

In an embodiment, the 4D energy-field package assembly may include the energy waveguide having a reflector element with a first reflector located on the first side of the energy waveguide, the first reflector having one or more aperture stops formed therethrough, and a second reflector located on the second side of the energy waveguide, the second reflector having one or more aperture stops formed therethrough, similar to that discussed above and shown in FIG. 22. In another embodiment, the assembly may include a reflector element where a size of the one or more aperture stops of the first and second reflectors may be constant. In yet another, the assembly may include a reflector element where a size of the one or more aperture stops of the first and second reflectors varies.

In an embodiment, the assembly may include a reflector element with first and second reflectors having one or more parabolic surfaces, such that a first parabolic surface of the first reflector and a first parabolic surface of the second reflector are configured to reflect energy along each energy propagation path, the parabolic properties similar to those disclosed above and herein.

In another embodiment, the reflector element includes a focal length of the first parabolic surface of the first reflector being the same as a focal length of the first parabolic surface of the second reflector, the focal length properties similar to those disclosed above and herein. In one other embodiment, the reflector element includes a focal length of the first parabolic surface of the first reflector being different than a focal length of the first parabolic surface of the second reflector. In yet another embodiment, the reflector element includes an additional energy-inhibiting element located between the first and second sides of the reflector element. In operation, the energy-inhibiting element may be positioned to limit propagation of energy along a portion of the plurality of energy propagation paths that do not extend through an aperture of a lenslet. In some instances, the shape of the lenslet may be configured to additionally alter the unique direction of each energy propagation path. In other instances, energy directed along an energy propagation path through the lenslet may substantially fill an aperture of the lens let.

Figure 23:
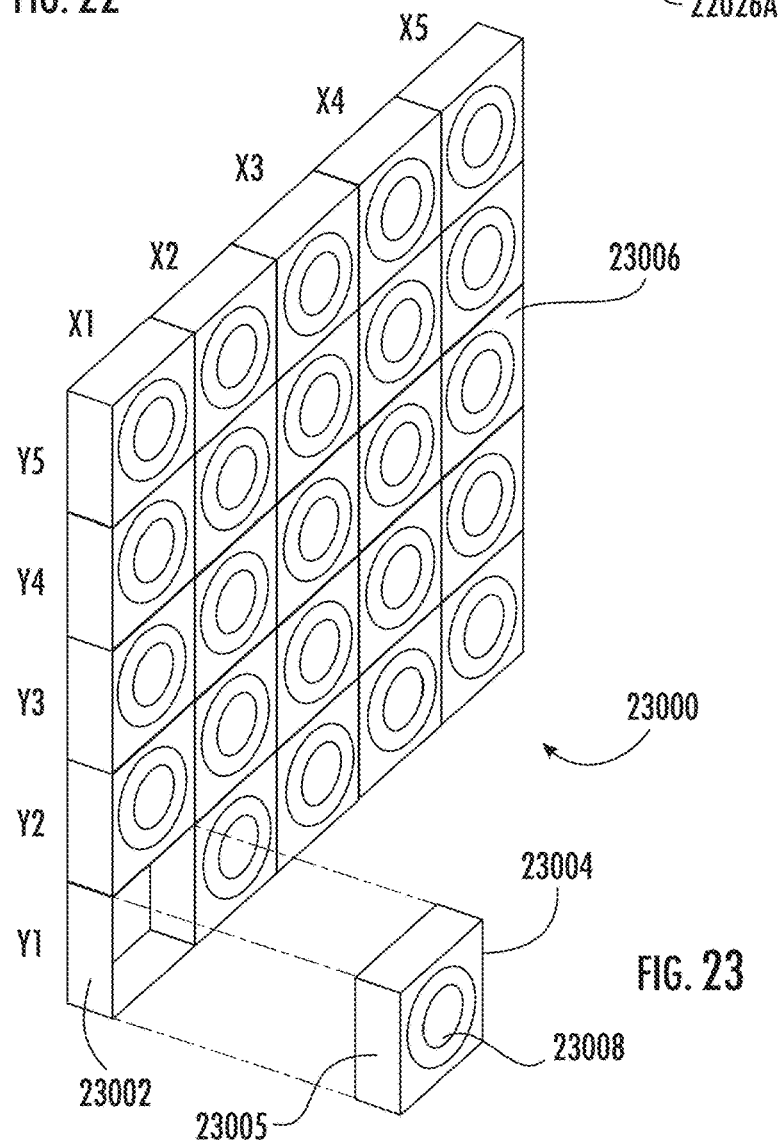
FIG. 23 depicts an embodiment of a 4D energy-field package assembly of this disclosure demonstrating how modular 4D energy-field packages may attach to a mount.

FIG. 23 shows an embodiment of the 4D energy-field package assembly 23000 of this disclosure having a mounting assembly 23002 to which a plurality of modular 4D energy-field packages 23004 may be attached thereto to form an energy-projection surface 23006. In an embodiment, the mounting assembly 23002 may include a printed circuit board (PCB) and associated mechanical structures, among other structures. In other instances, the mounting assembly 23002 may include other structures or forms known in the art. In operation, the mount 23002 may be configured to receive different arrangements of a plurality of modular 4D energy-field packages 23004 in various embodiments. As shown in FIG. 23, the mounting assembly 23002 includes a square-like or rectangular shape, but it will be appreciated that the mounting assembly 23002 may include without limitation a variety of shapes and sizes including irregular or broken shapes.

In some embodiments of the 4D energy-field package assembly 23000, like the one depicted in FIG. 23, the modular 4D energy-field packages may further include a mechanical encasement 23005 that surrounds each energy waveguide 23008. In other embodiments the mechanical encasement 23005 may limit propagation paths that do not extend through the aperture (e.g., 22020 of FIG. 22) of the waveguide 23008. In yet some other embodiments, there may also be a mechanical encasement 23005 surrounding the energy-source system, as described with reference to 20113 of FIG. 20 of the modular 4D energy-field package 23004. It will be appreciated that in instances where the modular 4D energy-field package include a plurality of waveguides, the mechanical encasement may surround each waveguide, the plurality of waveguides, or selective units of waveguides.

In one embodiment, the location of the energy waveguide 23008 of each modular 4D energy-field package 23004 of the plurality of modular 4D energy-field packages may include a two-dimensional (2D) spatial coordinate, and where the unique direction of each of the propagation paths may be determined by at least an energy location such as 22002A for propagation path 22028 of the energy waveguide 23004. The energy propagation path 22028 may further include a two-dimensional (2D) angular coordinate whereby the two-dimensional (2D) spatial coordinate and the two-dimensional (2D) angular coordinate form a four-dimensional (4D) coordinate set. The four-dimensional (4D) coordinate sets and their applications have been described elsewhere in this disclosure without limitation at least in reference to FIG. 6.

In some embodiments, the two-dimensional (2D) spatial coordinate may include X and Y coordinates as shown in FIG. 23. In these embodiments, the 4D energy-field package assembly of the plurality of energy propagation paths, such as 22028, may extend through a plurality of energy locations, such as 22002A, extending from the second side 22008 of the energy waveguide 22004 in a unique direction which is determined at least by the energy location 22002A relative to the waveguide 22004, similar to that as discussed above.

Figure 24:
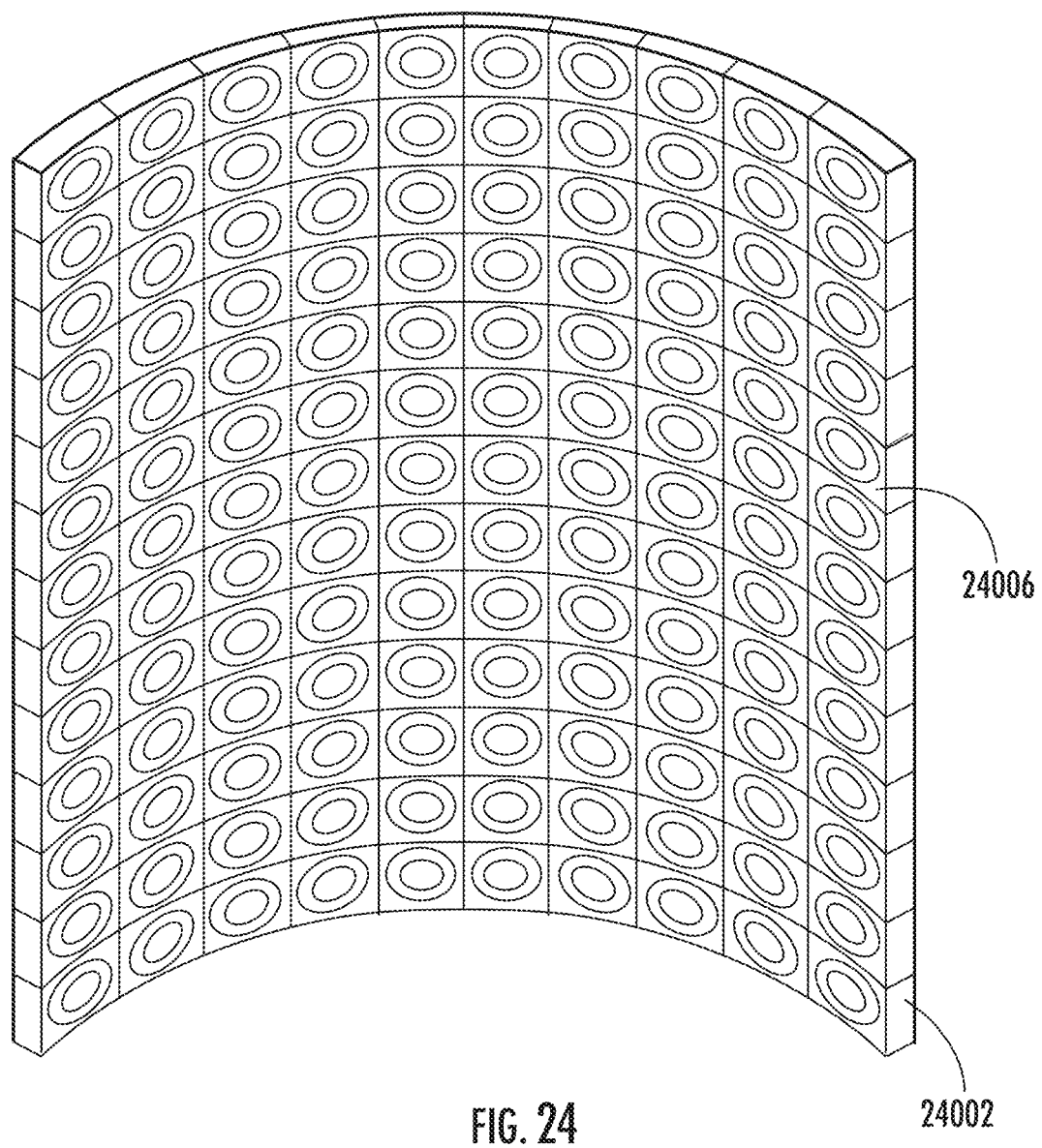
FIG. 24 depicts an embodiment of a 4D energy-field package assembly comprising a curved projection surface.

In some embodiments, the energy-projection surface 23006 may have different shapes and sizes. In other embodiments, like depicted in FIG. 23, the energy-projection surface 23006 may include a planar surface. In yet some other embodiments, like depicted in FIG. 24, the energy-projection surface may include a curved surface 24006. In some embodiments, the mounting assembly 24002 may be configured so that the energy-projection surface 24006 may be flat or curved, among other shapes and sizes and/or curvatures.

Figure 25A:
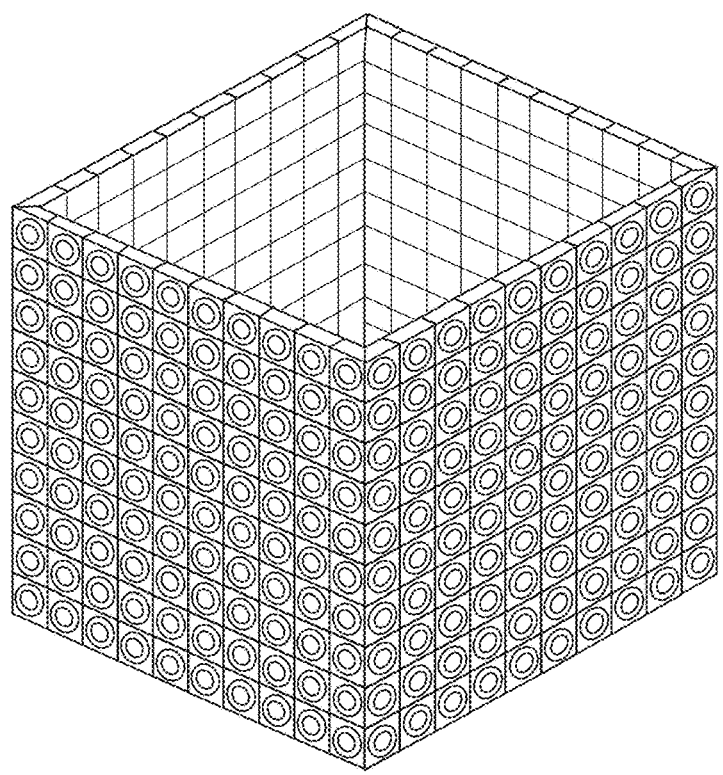
FIG. 25A, FIG. 25B, and FIG. 25C depict embodiments of 4D energy-field package assemblies arranged to comprise additional embodiments of the projection surface.
Figure 25B:
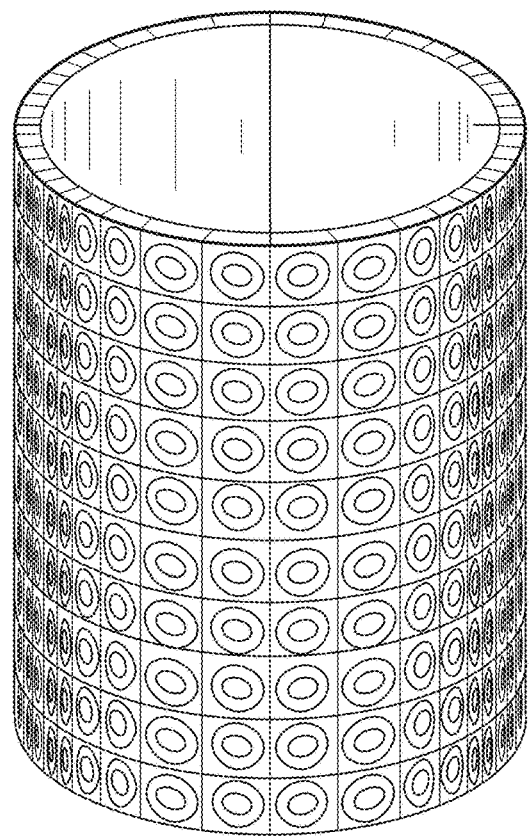
Figure 25C:
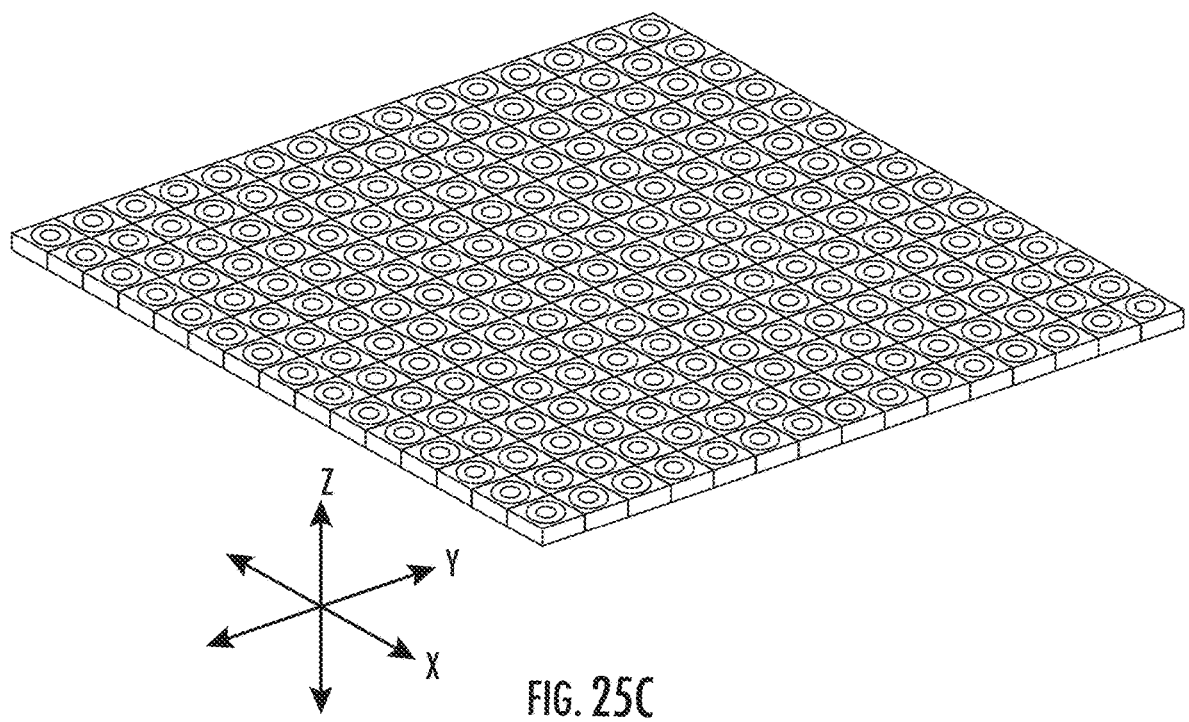

FIGS. 25A-C illustrate different arrangements of mounts and faces. It will be appreciated that FIG. 23, FIG. 24, and FIGS. 25A-C are provided for illustrative purposes only and do not limit the embodiments of this disclosure. Mounting assemblies and projection surfaces may take any variety of shapes and sizes in different embodiments. And, as can be appreciated, unless specifically denoted otherwise, all the different embodiments of the mounting assemblies 23002, 24002 and the projection surfaces 23006, 24006 may be combined with other embodiments of the 4D energy-field package assembly of this disclosure.

In some embodiments, the plurality of 4D energy-field packages may be disposed side-by-side on the mount or a plurality of mounts in an arrangement selected from a group consisting of: a hexagonal packing arrangement, a rectangular packing arrangement, or a non-regular packing arrangement. It will be appreciated that the packages may be mounted in any polygonal packing arrangements.

Figure 26:
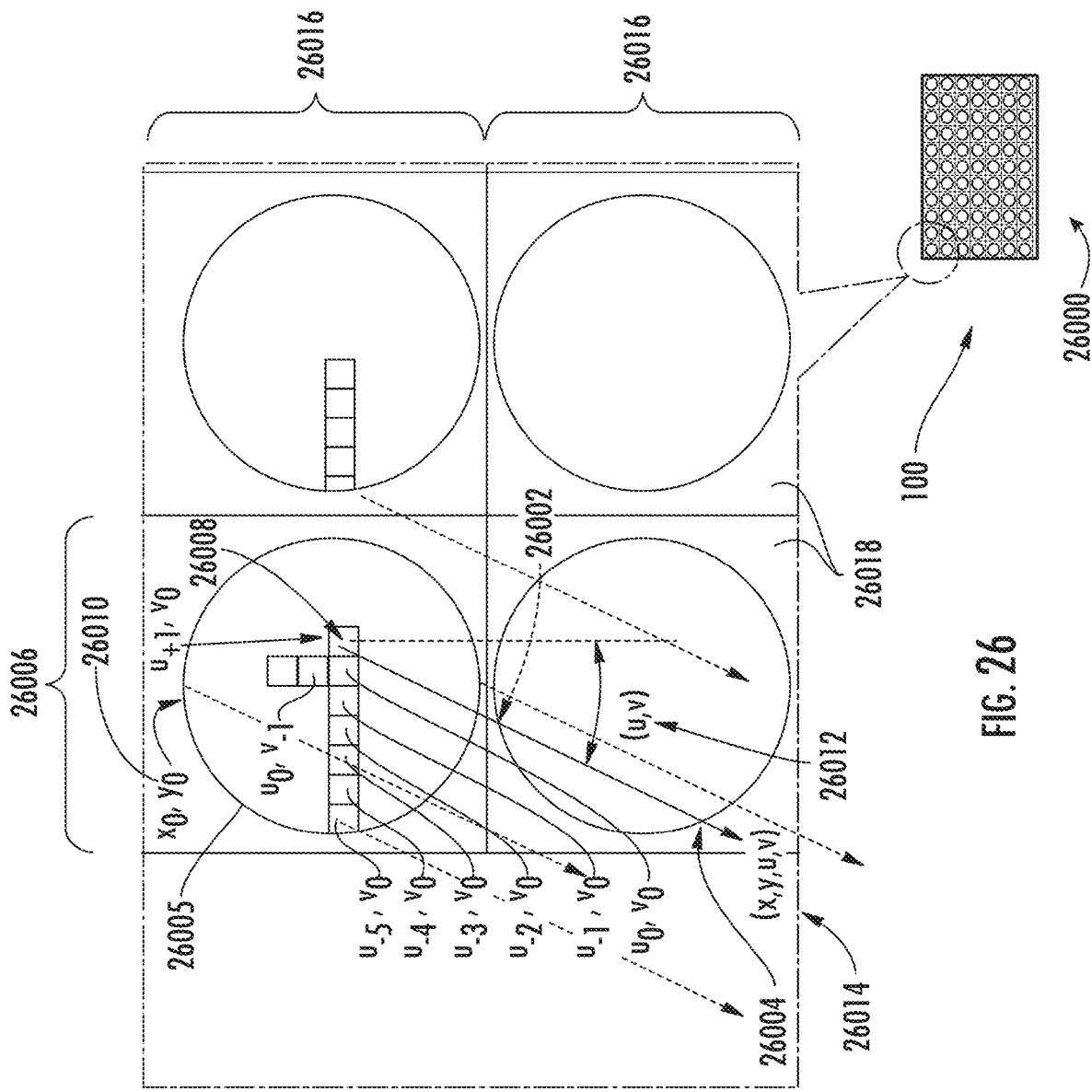
FIG. 26 is a front view illustration of an embodiment of an energy-projection surface of the 4D energy-field package assembly of this disclosure.

FIG. 26 is a front view illustration of an embodiment of an energy-projection surface 26000 of the 4D energy-field package assembly of this disclosure, where only one waveguide exists per energy-field package. It other embodiments, each 4D energy-field package of this assembly may include additional waveguides. An energy propagation path 26002 may extend in a unique direction 26004 from the waveguide 26005 of a modular 4D energy-field package 26006, which may be determined at least by a corresponding energy location 26008 of the modular 4D energy-field package 26006. The first modular 4D energy-field package 26006 may be defined by a spatial coordinate 26010 defining the location (x, y) of the waveguide 26005, and the unique direction 26004 which may be determined at least by first energy location 26008 as defined by an angular coordinate 26012 defining the directions (u, v) of the first energy propagation path 26002. The spatial coordinate 26010 and the angular coordinate 26012 may form a four-dimensional (x, y, u, v) light field coordinate set 26014 which defines the unique direction of the first energy propagation path 26002. Additional modular 4D packages 26016 separated by border 26018 may be defined by a different spatial coordinate. In other embodiments, the 4D energy-field package assemblies may have each package of the plurality of modular 4D energy-field packages defined by one or more spatial coordinates of a 4D coordinate set for each waveguide contained in the package.

Figure 27:
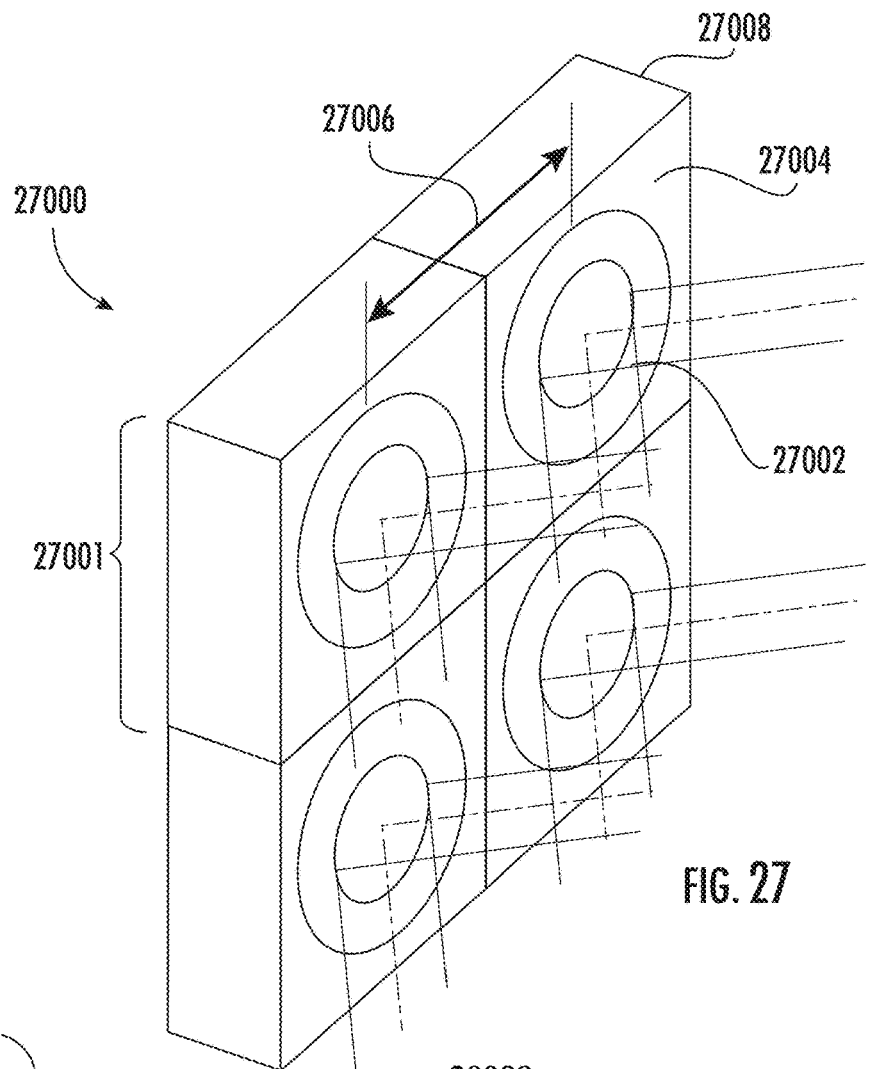
FIG. 27 depicts four modular 4D energy-field packages of an embodiment of this disclosure.

FIG. 27 depicts an assembly 27000 of four modular 4D energy-field packages 27001 placed together, with each module containing a waveguide similar to 22004 as shown in FIG. 22. This embodiment includes a border 27004 surrounding each energy waveguide 27002 of each modular 4D energy-field package 27001 of the plurality of modular 4D energy-field packages. The border 27004 can include a black region for reducing seams. In an embodiment, the border 27004 of the 4D energy-field packages 27001 may separate the waveguides 27002 of the modular 4D energy-field packages 27001 of the plurality of modular 4D energy-field packages by a distance 27006 when the plurality of modular 4D energy-field packages are placed together in the assembly 27000. The distance 27006 between the waveguides 27002 of the modular 4D energy-field packages 27000 of the plurality of modular 4D energy-field packages may prevent seams in a projected 4D energy field. In an embodiment, the distance 27006 may be wider than the gap between panels (not shown) of the 4D energy-field packages that can be assembled to form a large projection surface. FIG. 27 is provided for illustrative purposes and does not limit the embodiments of this disclosure. And, unless explicitly stated otherwise, the embodiments of the modular 4D energy-field package discussed with reference to FIG. 27 can be combined with all the other embodiments of the 4D energy-field package assembly of this disclosure.

In some embodiments, the modular 4D energy-field package may include multiple waveguides with a border separating each waveguide of the modular 4D energy-field package. In other embodiments, the width of the border on the outer edges of the modular 4D energy-field package may be wider than the width of the border between individual waveguides of the modular 4D energy-field package. Embodiments having multiple waveguides may also include an energy-inhibiting structure between each waveguide. Any energy-inhibiting structure of this disclosure may include but not limited to those discussed in reference to FIG. 9A-H, as well other energy-inhibiting structures known in the art.

In some embodiments, the energy-inhibiting structure may include a structure for attenuating or modifying energy propagation paths, the structure selected from a group consisting of: (a) an energy blocking structure; (b) an element configured to alter the at least one energy propagation path of the waveguide of each modular 4D energy-field package to alter a fill factor of the aperture of the energy waveguide of each modular 4D energy-field package; or (c) a structure configured to limit an angular extent of energy proximate an energy location of each modular 4D energy-field package. In operation, the energy-inhibiting structure may be positioned adjacent to the energy locations of each modular 4D energy-field package and generally towards the energy waveguide of each modular 4D energy-field package. In the alternative, the energy-inhibiting structure may be positioned adjacent to the energy waveguides of each modular 4D energy-field package and generally towards the energy locations of each modular 4D energy-field package. In one example, the energy-inhibiting structure may be an energy blocking structure that is positioned adjacent to the energy locations of each modular 4D energy-field package and generally towards the energy waveguide of each modular 4D energy-field package for attenuating or modifying energy propagation paths.

Figure 28:
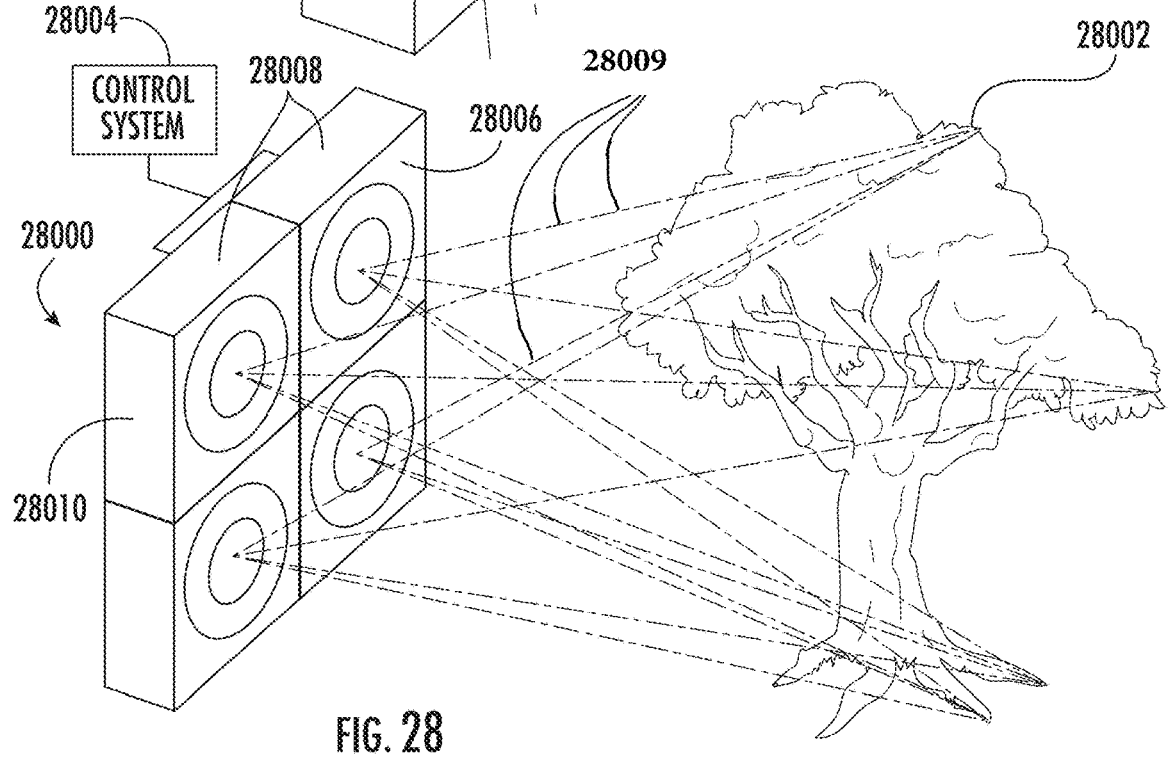
FIG. 28 illustrates an embodiment of the energy-field package assembly of this disclosure projecting an energy field.

FIG. 28 depicts an embodiment of a 4D energy-field assembly 28000 of this disclosure projecting light rays that converge to form points that determine the surface of a projected holographic tree 28002. The 4D energy-field assembly 28000 may include a control system 28004 for directing the plurality of energy locations within plurality of 4D energy-field packages 28008 to form the corresponding propagation paths as shown. In operation, the control system 28004 may be in communication with the plurality of modular 4D energy-field packages 28008 configured to operate the plurality of modular 4D energy-field packages 28008 to direct energy along the plurality of propagation paths 28009 to project a 4D energy field 28002 from the energy-projection surface 28006. In some embodiments, the energy-projection surface 28010 may include a seamless energy-projection surface.

As will be appreciated, the disclosures of this embodiment are not limited to projecting light fields. Other embodiments may project other forms of energy. In some embodiments, spatial coordinates may define a subset of modular 4D energy-field packages of the plurality of modular 4D energy-field packages rather than a single modular 4D energy-field packages.

Figure 29:
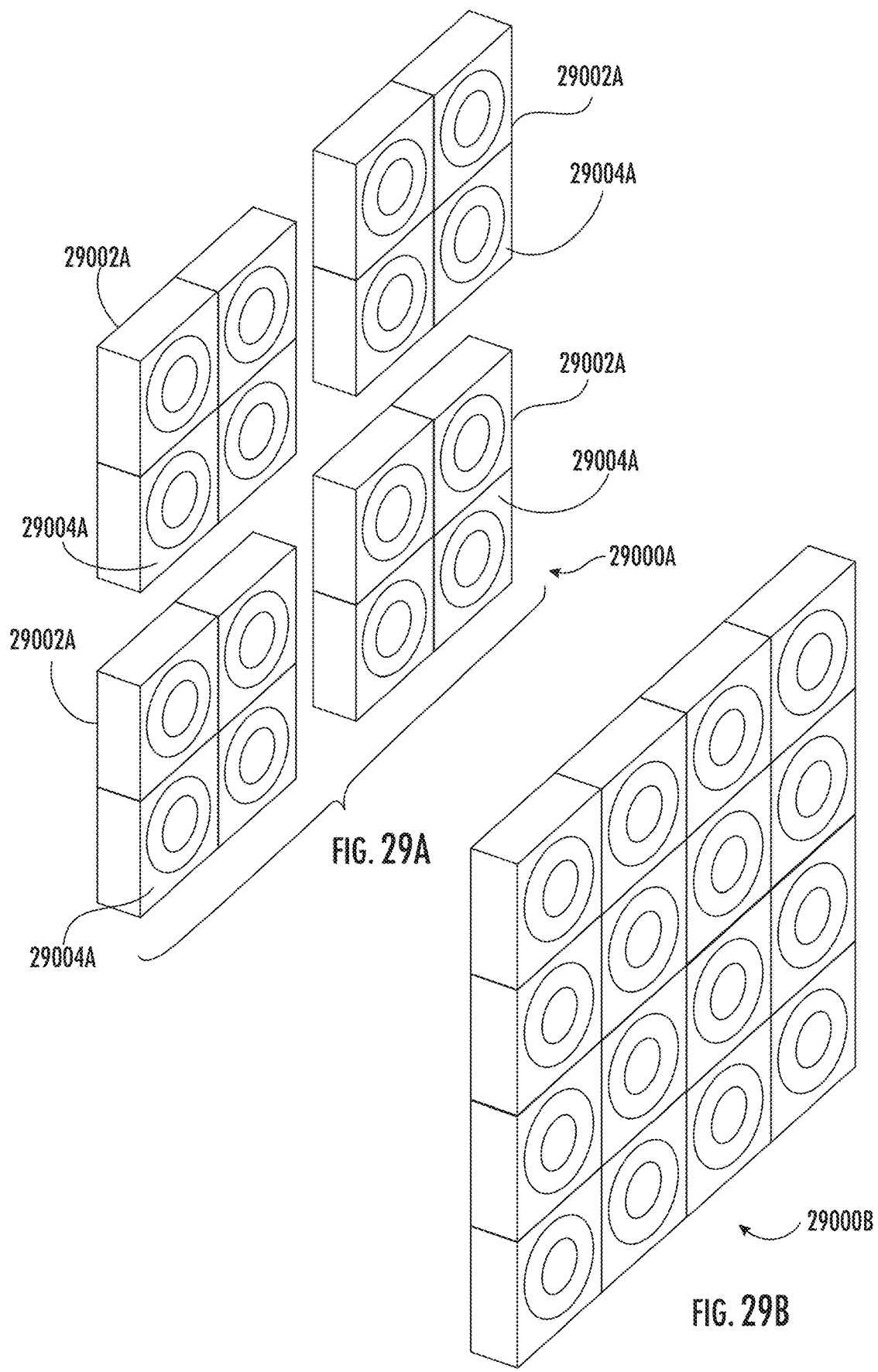
FIG. 29A and FIG. 29B depict an embodiment of a 4D energy-field package of this disclosure that combines a plurality of mounts into an expanded energy-projection surface.

Some embodiments of the 4D energy-field package assembly 29000A, like the one depicted in FIGS. 29A and 29B, may include a plurality of mounts 29002A. In one embodiment, the plurality of mounts 29002A can be arranged to form an expanded energy-projection surface 29000B. In another embodiment, a plurality of mounting assemblies may be separated into different locations to form separate projection surfaces. In other words, the 4D energy-field package assembly may include a second mount to which the plurality of modular 4D energy-field packages may be attached to form a second energy-projection surface. The two mounts may communicate with each other through any means known in the art to cooperatively project an energy field. In some embodiments, a plurality of energy sources may supply energy to the energy locations of the modular 4D package assemblies of the projection surface(s). In other embodiments, there may be a plurality of energy sources to provide energy to the energy sources of a plurality of mounts.

Modular 4D energy-field packages offer many advantages. As discussed elsewhere in this disclosure a modular 4D energy-field package may help reduce or eliminate the appearance of seams in a projected energy field. It also may be helpful to have modular 4D energy-field packages to allow versatile displays that can be arranged in a variety of shapes and sizes. Modular pieces may be added or removed from energy-projecting surfaces and make repairs less costly, quicker and easier. Instead of a having to replace an entire surface, only the damaged or defective modular units need to be replaced.

In some embodiments, the modular 4D energy-field package may be integrated onto a chip (e.g., silicon chip or other suitable semiconductor chip). This can be carried out by attachment to a printed circuit board (PCB) by any means known in the art. This may also allow for smaller modular 4D energy-field packages with more densely packed energy sources for maintaining resolution while reducing seams.

As referenced above, the energy waveguides of the 4D energy-field package assembly may include any of the waveguides referenced throughout this disclosure including without limitation waveguides depicted or discussed with reference to FIGS. 9-11 and FIGS. 13-16, and waveguides having lenses, lenslets, or reflector elements, among others. Different embodiments of 4D energy-field package assemblies of this disclosure may include different energy-inhibiting elements of all the different waveguide embodiments of this disclosure and known in the art, the different embodiments of baffles of all the different waveguide embodiments of this disclosure and known in the art, and the different embodiments of apertures of all the different waveguide elements of this disclosure or known in the art. These embodiments may be combined with each and all embodiments of the 4D energy-field package assembly unless specifically denoted otherwise.

Figure 30:
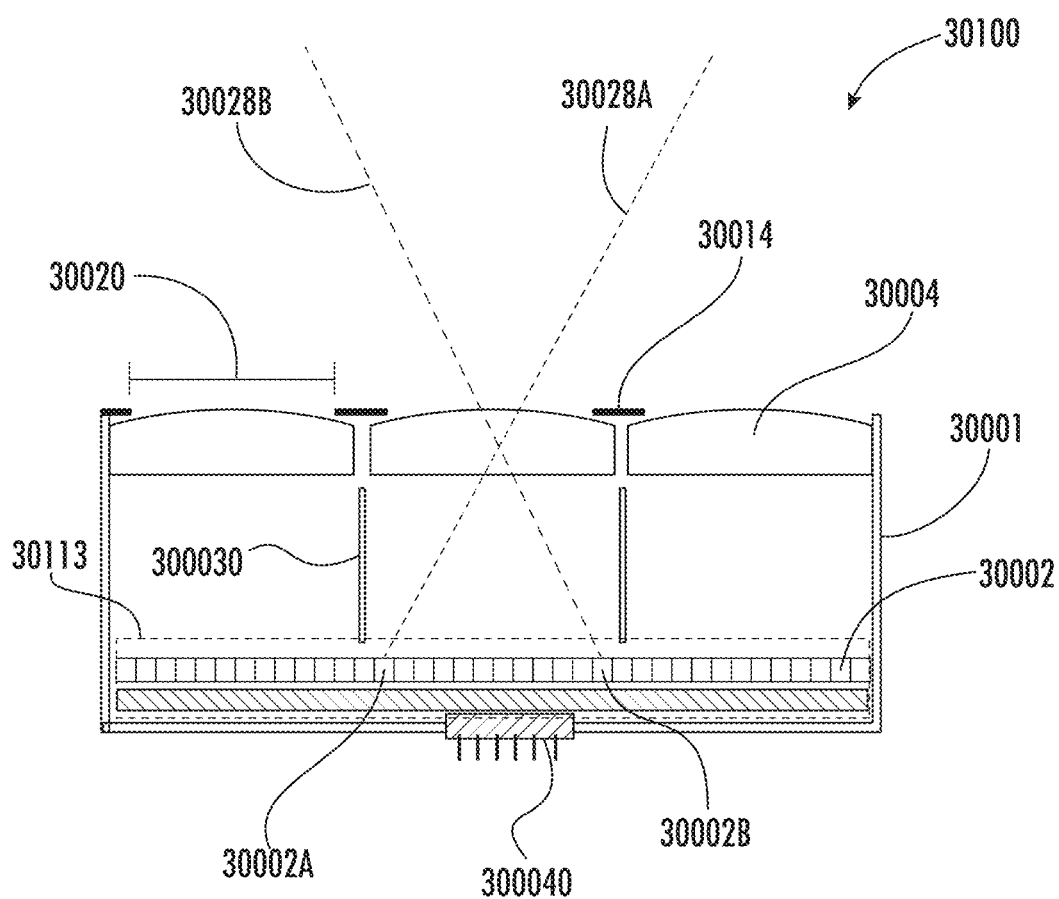
FIG. 30 depicts an embodiment of a modular 4D energy-field package of this disclosure that comprises a plurality of waveguides.

FIG. 30 depicts an embodiment of a modular 4D energy-field package 30100 of this disclosure having a plurality of waveguides 30004 and a plurality of energy locations 30002A as described elsewhere in this disclosure, each waveguide 30004 having a unique 2D spatial coordinate. Similarly, each propagation path 30028A, 30028B extends from a waveguide in a unique direction at least determined by a corresponding energy location 30002A, 30002B, respectively. Propagation paths 30028A, 30028B may substantially fill the aperture 30020 of the waveguide. In an embodiment, the waveguides 30004 may be separated by a border 30014 that may reduce seaming as described elsewhere in this disclosure. In some instances, the border 30014 may also contribute to defining the aperture of the waveguide 30020. The 4D energy-field package may include an energy-inhibiting element 30030, which may take on any form described elsewhere throughout this disclosure, including but not limited to those described with reference to FIGS. 9A-H, including a baffle structure, among others.

In an embodiment, the energy-inhibiting elements 30030 may inhibit or attenuate energy that do not extend through an aperture 30020 or energy from energy source locations 30002 that are not associated with a waveguide. In an embodiment, the energy-inhibiting element 30030 may limit propagation of energy along propagation paths that do not extend through the its own aperture. In an embodiment, the energy-inhibiting element 30030 may be located on the energy source side of the energy waveguide similar to that disclosed herein.

In some embodiments, there may be a plurality of energy-inhibiting elements 30030. In another embodiment, there may be a mechanical casing 30001 similar to that described above with reference to 23005 of FIG. 23. The package 30100 may include an energy-source system 30113 having a plurality of energy sources configured to deliver energy to energy locations 30002. The energy-source system 30113 may be similar to those described elsewhere throughout this disclosure, including without limitation the energy-source systems described with reference to FIG. 20. In some instances the energy-source system may further include a relay, among other structures. In other embodiments, the energy locations 30002 may be pixels associated with an emissive display. As depicted, the modular 4D energy-field package may have square cut waveguides 30004, but this does not limit the embodiments of this disclosure and any type of waveguides as those known in the art may be utilized. The modular 4D energy-field package 30100 may also include an electrical contact 300040 that allows the package to be integrated into an assembly of modular 4D energy-field package 30100. As can be appreciated all embodiments of the modular 4D energy-field package 30100 of this disclosure may be combined with all the other embodiments disclosed herein.

Figure 31A:
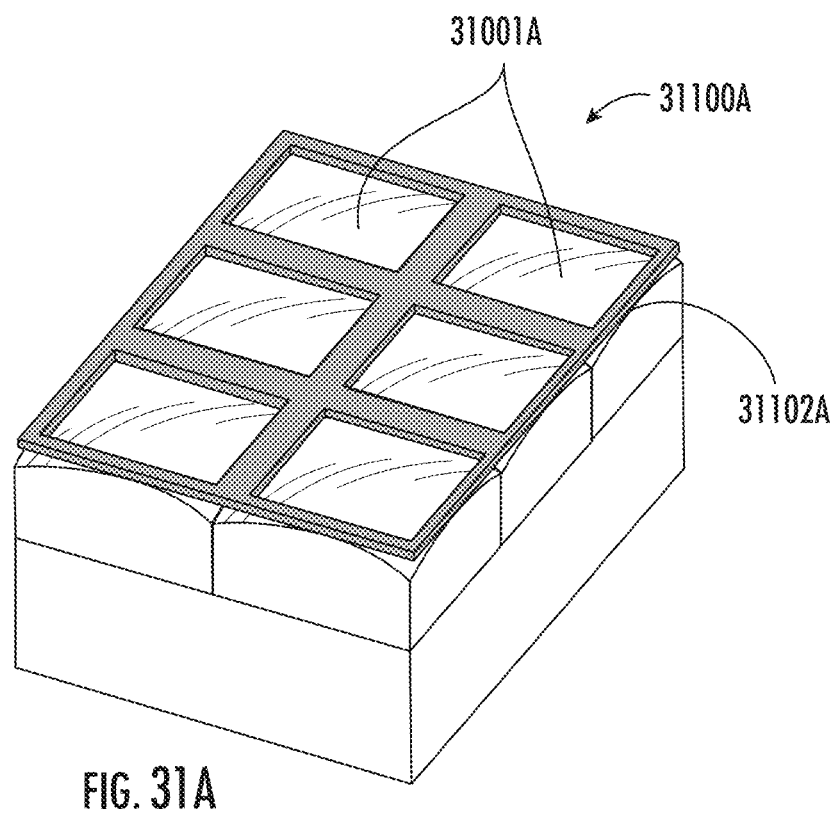
FIGS. 31A and B depict an embodiment of a modular 4D energy-field package of this disclosure that comprises a plurality of waveguides that is arranged into a 4D energy-field package assembly.
Figure 31B:
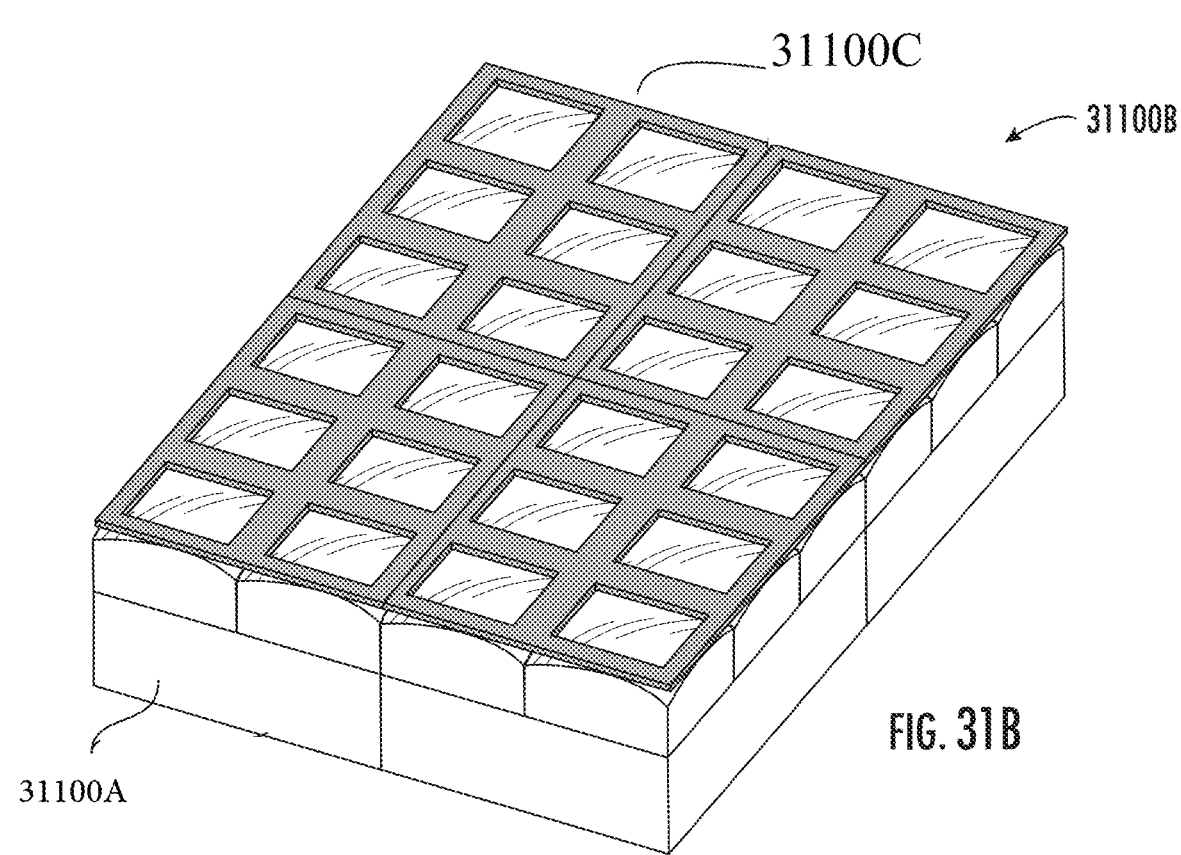

FIGS. 31A-B depict modular 4D energy-field packages with multiple waveguides joined into an assembly of modular 4D energy-field packages. FIG. 31A depicts a modular 4D energy-field package 31100A with six waveguides 31001A separated by a border 31102A. The border 31102A may include a black region configured to separate the waveguides 31001A, and allow multiple modules to be placed together in a larger assembly so that there may be consistent spacing between waveguides of adjacent modules, and thus of the entire assembly, preventing seaming artifacts. Note that the width of the border 31102A at the edges of the module may be close to half of the width of the border 31102A at the interior of the module 31100A. This allows two modules 31100A to be placed next to one another, and all the waveguides 31001A of the combined modules to have consistent spacing, similar to the spacing shown between modules 18002B and 18004B in FIG. 18B.

FIG. 31B depicts four modular 4D energy-field package 31100A in an assembly of 4D modular energy-field packages 31100B. In an embodiment, the assembly 31100B contains uniform spacing of waveguides 31001A in each dimension, due to the way the waveguides 31001A have been spaced together and the border 31100C has been constructed in each separate module 31100A. As be will appreciated the number of waveguides 3100A per modular 4D energy-field package 31100A may vary from embodiment to embodiment. As will be appreciated the number of energy-field packages 31100A joined to form an assembly 31100B may also vary from embodiment to embodiment. And, embodiments of the assembly of 4D modular energy-field packages 31100A that include multiple waveguides 31001A may form any surface or arrangement depicted elsewhere throughout this disclosure including but not limited to those depicted in FIGS. 23, 24 and 25A-C.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically, and by way of example, although the headings refer to a "Field of Invention," such claims should not be limited by the language under this heading to describe the so-called technical field. Further, a description of technology in the "Background of the Invention" section is not to be construed as an admission that technology is prior art to any invention (s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. In general, but subject to the preceding discussion, a numerical value herein that is modified by a word of approximation such as "about" may vary from the stated value by at least ±1, 2, 3, 4, 5, 6, 7, 10, 12 or 15%.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result. Words relating to relative position of elements such as "near," "proximate to," and "adjacent to" shall mean sufficiently close to have a material effect upon the respective system element interactions. Other words of approximation similarly refer to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A four-dimensional (4D) energy-field package assembly comprising:
a plurality of modular 4D energy-field packages wherein each modular 4D energy-field package comprises;
an energy-source system configured to provide energy to a plurality of energy locations and comprising a plurality of energy sources; and
at least one energy waveguide wherein each energy waveguide is configured to direct energy from the plurality of energy locations from a first side of the energy waveguide to a second side of the energy waveguide along a plurality of energy propagation paths extending through the plurality of energy locations, each energy propagation path being defined by a chief ray formed between one energy location of the plurality of energy locations and the energy waveguide wherein each energy propagation path extends from the energy waveguide in a unique direction determined at least by the one energy location; and
wherein the location of each energy waveguide comprises a two-dimensional (2D) spatial coordinate, and wherein the unique direction of each energy propagation path comprises a 2D angular coordinate, whereby the 2D spatial coordinate and the 2D angular coordinate form a four-dimensional (4D) coordinate set;
wherein energy directed along at least one energy propagation path of at least one modular 4D energy-field package converges with energy directed along at least one other energy propagation path of at least one other 4D energy-field package; and
wherein the at least one energy propagation path and the at least one other energy propagation path converge at a location on the first side of the at least one energy waveguide of the at least one modular 4D energy-field package; and
a mount to which the plurality of modular 4D energy-field packages are attached to form an energy-projection surface such that the plurality of modular 4D energy-field packages are operable to direct energy according to respective independent 4D functions that together operate as a collection of 4D functions for the assembled energy projection surface.

2. The 4D energy-field package assembly of claim 1, wherein at least one of the plurality of modular 4D energy-field packages is integrated onto a chip.

3. The 4D energy-field package assembly of claim 2, wherein the chip of the at least one of the plurality of modular 4D energy-field packages comprises a silicon chip.

4. The 4D energy-field package assembly of claim 1, wherein at least one modular 4D energy-field package further comprises a border surrounding the at least one energy waveguide of the at least one modular 4D energy-field package.

5. The 4D energy-field package assembly of claim 4, wherein the border of the at least one modular 4D energy-field package surrounds each energy waveguide of the at least one modular 4D energy-field package.

6. The 4D energy-field package assembly of claim 4, wherein the at least one border comprises a black region.

7. The 4D energy-field package assembly of claim 4, wherein the border is configured to separate the at least one energy waveguide of the plurality of modular 4D energy-field packages when attached to the mount.

8. The 4D energy-field package assembly of claim 7, wherein the distance between the at least one energy waveguide of the plurality of modular 4D energy-field packages prevents seams in the 4D energy field.

9. The 4D energy-field package assembly of claim 1 wherein the plurality of 4D energy-field packages are attached to the mount to form a grid of modular 4D energy field-packages wherein each modular 4D energy-field package attached to the mount further comprises a border that evenly separates all of the at least one energy waveguide of the plurality of 4D energy-field packages attached to the mount.

10. The 4D energy-field package assembly of claim 9, wherein the border of each modular 4D energy-field package attached to the mount evenly separates each energy waveguide of the at least one energy waveguide of each modular 4D energy-field package attached to the mount.

11. The 4D energy-field package assembly of claim 1, wherein each energy waveguide of the at least one energy waveguide of at least one modular 4D energy-field package further comprises an aperture wherein a first energy propagation path of the plurality of energy propagation paths substantially fills the aperture.

12. The 4D energy-field package assembly of claim 11, wherein the at least one modular 4D energy-field package limits propagation of energy along energy propagation paths that do not extend through the aperture of any waveguide.

13. The 4D energy-field package assembly of claim of claim 11, wherein a mechanical encasement limits propagation of energy along energy propagation paths that do not extend through the aperture of any waveguide.

14. The 4D energy-field package assembly of claim 1, further comprising a control system in communication with the plurality of modular 4D energy-field packages and wherein the control system configured to operate the energy-source system of the plurality of modular 4D energy-field packages to project a 4D energy field from the energy-projection surface.

15. The 4D energy-field package assembly of claim 1, wherein at least one additional energy propagation path of the at least one modular 4D energy-field package and at least one other additional energy propagation path of the at least one other 4D energy-field package converge at a location on the second side of the at least one energy waveguide of the at least one modular 4D energy-field package.

16. The 4D energy-field package assembly of claim 1, wherein the at least one energy waveguide of at least one modular 4D energy-field package of the plurality of modular 4D energy-field packages comprises a structure for directing energy, the structure selected from a group consisting of:
   a) a structure configured to alter an angular direction of energy passing therethrough;
   b) a structure comprising at least one numerical aperture;
   c) a structure configured to redirect energy off at least one internal surface; or
   d) an energy relay.

17. The 4D energy-field package assembly of claim 1, wherein the energy-projection surface comprises a planar surface.

18. The 4D energy-field package assembly of claim 1, wherein energy-projection surface comprises a curved surface.

19. The 4D energy-field package assembly of claim 1, wherein at least one modular 4D energy-field package comprises a magnifying waveguide disposed on the second side of each energy waveguide of the at least one energy waveguide.

20. The 4D energy-field package assembly of claim 1, wherein the energy sources of the pluralities of energy sources comprises one or more emissive displays.

21. The 4D energy-field package assembly of claim 20, wherein the one or more emissive displays are one of a LED, OLED, AMOLED, and TOLED.

22. The 4D energy-field package assembly of claim 1, further comprising at least one second mount to which the plurality of modular 4D energy-field packages are attached to form at least one second energy-projection surface.

23. The 4D energy-field package assembly of claim 1, wherein the mount comprises a printed circuit board.

24. The 4D energy-field package assembly of claim 1, wherein energy directed along the pluralities of energy propagation paths of the plurality of modular 4D energy-field packages is electromagnetic energy defined by a wavelength, the wavelength belonging to a regime selected from a group consisting of:
   a) visible light;
   b) ultraviolet;
   c) infrared; or
   d) x-ray.

25. The 4D energy-field package assembly of claim 1, wherein energy directed along the pluralities of energy propagation paths of the plurality of modular 4D energy-field packages is mechanical energy defined by pressure waves, the waves selected from a group consisting of:
   a) tactile pressure waves;
   b) acoustic sound vibrations; or
   c) ultrasound waves.

26. The 4D energy-field package assembly of claim 1, wherein the 4D coordinate set of each energy propagation path uniquely identifies each energy propagation path.

27. The 4D energy-field package assembly of claim 1, wherein the at least one energy waveguide of at least one modular 4D energy-field package comprises a lenslet.

28. The 4D energy-field package assembly of claim 27, wherein the lenslet comprises a Fresnel lens.

29. The 4D energy-field package assembly of claim 27, wherein a shape of the lenslet is configured to additionally alter the unique direction of each energy propagation path.

30. The 4D energy-field package assembly of claim 1, wherein the at least one energy waveguide of each modular 4D energy-field package comprises a plurality of energy waveguides.

31. The 4D energy-field package assembly of claim 30, wherein light directed along a first energy propagation path of the plurality of energy propagation paths through a first energy waveguide of the plurality of energy waveguides of each modular 4D package assembly substantially fills an aperture of the first energy waveguide.

32. The 4D energy-field package assembly of claim 31, wherein each modular 4D energy-field package further comprises an energy-inhibiting element positioned to limit propagation of energy along a portion of energy propagation paths of the plurality of energy propagation paths that do not extend through the aperture of the first energy waveguide.

33. The 4D energy-field package assembly of claim of claim 32, where the energy-inhibiting element comprises a baffle structure.

34. The 4D energy-field package assembly of claim 31, further comprising a mechanical encasement that surrounds each energy waveguide of the plurality of energy waveguides and the energy-source system of each modular 4D energy-field package.

35. The 4D energy-field package assembly of claim of claim 34, wherein the mechanical encasement limits propagation of energy along energy propagation paths that do not extend through the aperture of the first energy waveguide.

36. The 4D energy-field package assembly of claim 1, further comprising a mechanical encasement that surrounds the at least one energy waveguide and the energy-source system of each modular 4D energy-field package.

37. The 4D energy-field package assembly of claim 1, wherein each energy waveguide of the at least one energy waveguide of at least one modular 4D energy-field package comprises a structure for attenuating or modifying at least one energy propagation path of each energy waveguide, the structure selected from a group consisting of:
  (a) an energy blocking structure;
  (b) an element configured to alter the at least one energy propagation path of each energy waveguide to alter a fill factor of an aperture of each energy waveguide; or
  (c) a structure configured to limit an angular extent of energy proximate an energy location of each modular 4D energy-field package.

38. A four-dimensional (4D) energy-field package assembly comprising:
  a plurality of modular 4D energy-field packages wherein each modular 4D energy-field package comprises;
    an energy-source system configured to provide energy to a plurality of energy locations and comprising a plurality of energy sources; and
    at least one energy waveguide wherein each energy waveguide is configured to direct energy from the plurality of energy locations from a first side of the energy waveguide to a second side of the energy waveguide along a plurality of energy propagation paths extending through the plurality of energy locations, each energy propagation path being defined by a chief ray formed between one energy location of the plurality of energy locations and the energy waveguide wherein each energy propagation path extends from the energy waveguide in a unique direction determined at least by the one energy location; and
    wherein the location of each energy waveguide comprises a two-dimensional (2D) spatial coordinate, and wherein the unique direction of each energy propagation path comprises a 2D angular coordinate, whereby the 2D spatial coordinate and the 2D angular coordinate form a four-dimensional (4D) coordinate set;
    wherein the at least one energy waveguide of at least one modular 4D energy-field package comprises a reflector element comprising a first reflector located on the first side of the energy waveguide, the first reflector comprising one or more aperture stops formed therethrough, and a second reflector located on the second side of the energy waveguide, the second reflector comprising one or more aperture stops formed therethrough; and
  a mount to which the plurality of modular 4D energy-field packages are attached to form an energy-projection surface.

39. The 4D energy-field package assembly of claim 38, wherein a size of the one or more aperture stops of the first and second reflectors is constant.

40. The 4D energy-field package assembly of claim 38, wherein a size of the one or more aperture stops of the first and second reflectors varies.

41. The 4D energy-field package assembly of claim 38, wherein the first and second reflectors comprise one or more parabolic surfaces, such that a first parabolic surface of the first reflector and a first parabolic surface of the second reflector are configured to reflect energy along each energy propagation path of the at least one energy waveguide.

42. The 4D energy-field package assembly of claim 41, wherein a focal length of the first parabolic surface of the first reflector is the same as a focal length of the first parabolic surface of the second reflector.

43. The 4D energy-field package assembly of claim 41, wherein a focal length of the first parabolic surface of the first reflector is different than a focal length of the first parabolic surface of the second reflector.

* * * * *